(12) United States Patent
Tadokoro et al.

(10) Patent No.: US 10,539,872 B2
(45) Date of Patent: Jan. 21, 2020

(54) PHOTOSENSITIVE COMPOSITION AND COMPOUND

(71) Applicant: TOKYO OHKA KOGYO CO., LTD., Kawasaki-shi (JP)

(72) Inventors: Yoshinori Tadokoro, Kawasaki (JP); Dai Shiota, Kawasaki (JP)

(73) Assignee: TOKYO OHKA KOGYO CO., LTD., Kawasaki-Shi (JP)

( * ) Notice: Subject to any disclaimer, the term of this patent is extended or adjusted under 35 U.S.C. 154(b) by 0 days.

(21) Appl. No.: 15/323,043

(22) PCT Filed: Jul. 14, 2015

(86) PCT No.: PCT/JP2015/070160
§ 371 (c)(1),
(2) Date: Dec. 29, 2016

(87) PCT Pub. No.: WO2016/010036
PCT Pub. Date: Jan. 21, 2016

(65) Prior Publication Data
US 2017/0160636 A1   Jun. 8, 2017

(30) Foreign Application Priority Data

Jul. 15, 2014 (JP) ................................. 2014-145257
Oct. 10, 2014 (JP) ................................. 2014-209470
Jun. 24, 2015 (JP) ................................. 2015-126581

(51) Int. Cl.
*G03F 7/031* (2006.01)
*G03F 7/004* (2006.01)
(Continued)

(52) U.S. Cl.
CPC .............. *G03F 7/031* (2013.01); *C07C 45/46* (2013.01); *C07C 201/12* (2013.01);
(Continued)

(58) Field of Classification Search
None
See application file for complete search history.

(56) References Cited

U.S. PATENT DOCUMENTS 9,316,906 B2   4/2016   Shin et al.
9,684,238 B2   6/2017   Harihara et al.
(Continued)

FOREIGN PATENT DOCUMENTS

CN         101508744        8/2009
EP         2385072 A1       11/2011
(Continued)

OTHER PUBLICATIONS

Machine translation of JP 2012-113104 (2012).*
(Continued)

*Primary Examiner* — Martin J Angebrannndt
(74) *Attorney, Agent, or Firm* — Knobbe, Martens, Olson & Bear LLP

(57) ABSTRACT

A photosensitive composition having excellent sensitivity, an insulating film formed using the composition, a color filter formed using the composition, a display device provided with the insulating film or color filter, and a compound suitable for incorporation as a photopolymerization initiator into the composition. This photosensitive composition includes a photopolymerizable compound and a photopolymerization initiator. The photopolymerization initiator contains a compound represented by formula (1) below in which $R^1$ is a hydrogen atom, a nitro group, or a monovalent organic group; $R^2$ and $R^3$ are each an optionally substituted linear alkyl group, an optionally substituted cyclic organic group, or a hydrogen atom, and $R^2$ and $R^3$ may be bonded to one another to form a ring; $R^4$ is a monovalent organic group; $R^5$ is a hydrogen atom, an optionally substituted
(Continued)

C1-11 alkyl group, or an optionally substituted aryl group; n is an integer from 0 to 4; and m is 0 or 1.

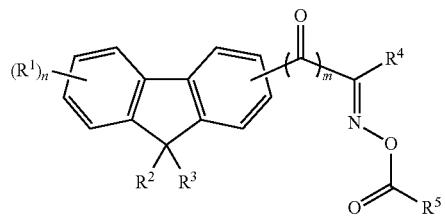

(1)

6 Claims, 1 Drawing Sheet

(51) Int. Cl.
    C07C 251/66     (2006.01)
    C07C 45/46     (2006.01)
    G02B 5/22     (2006.01)
    G02F 1/1335     (2006.01)
    C07C 201/12     (2006.01)
    C07C 249/10     (2006.01)
    C07D 333/22     (2006.01)
    G03F 7/00     (2006.01)
    C07C 333/26     (2006.01)

(52) U.S. Cl.
    CPC .......... C07C 249/10 (2013.01); C07C 251/66 (2013.01); C07D 333/22 (2013.01); G02B 5/223 (2013.01); G02F 1/133514 (2013.01); G03F 7/0007 (2013.01)

(56) References Cited

U.S. PATENT DOCUMENTS

| | | |
|---|---|---|
| 2001/0012596 A1 | 8/2001 | Kunimoto et al. |
| 2008/0085458 A1 | 4/2008 | Yamato et al. |
| 2014/0255845 A1* | 9/2014 | Tsai ...................... G03F 7/0007 430/280.1 |
| 2015/0111152 A1 | 4/2015 | Shin et al. |
| 2015/0259321 A1 | 9/2015 | Harihara et al. |

FOREIGN PATENT DOCUMENTS

| | | | |
|---|---|---|---|
| EP | 2407456 | 1/2012 | |
| JP | 2001-233842 | 8/2001 | |
| JP | 2008-506749 | 3/2008 | |
| JP | 2008-100955 | 5/2008 | |
| JP | 2010-156879 | 7/2010 | |
| JP | 2012-113104 | * 6/2012 | ............. G03F 7/031 |
| JP | 2012-189997 | * 10/2012 | |
| JP | 2013-209623 | 10/2013 | |
| JP | 2014-137466 A | 7/2014 | |
| KR | 10-2012-0096427 A | 8/2012 | |
| KR | 10-2014-0075588 A | 6/2014 | |
| TW | 201425283 A | 7/2014 | |
| WO | WO2013/165207 A1 | 11/2013 | |
| WO | WO 2014/050738 | 4/2014 | |
| WO | 2015/036910 | * 3/2015 | |

OTHER PUBLICATIONS

Extended European search report issued in European Patent Application No. 15822097.0, dated Jul. 4, 2017.
Office Action issued in Taiwanese Patent Application No. 104122958, dated Feb. 21, 2018.
Office Action issued in Taiwanese Patent Application No. 106142231, dated Feb. 21, 2018.
Notification of Reasons for Refusal issued in Japanese Patent Application No. 2017-229068, dated Mar. 26, 2019.

* cited by examiner

PHOTOSENSITIVE COMPOSITION AND COMPOUND

This application is the U.S. National Phase under 35 U.S.C. § 371 of International Application PCT/JP2015/070160, filed Jul. 14, 2015, designating the U.S., and published in Japanese as WO 2016/010036 on Jan. 21, 2016, which claims priority to Japanese Patent Application No. 2014-145257, filed Jul. 15, 2014; to Japanese Patent Application No. 2014-209470, filed Oct. 10, 2014; and Japanese Patent Application No. 2015-126581, filed Jun. 24, 2015, the entire contents of which are incorporated herein by reference.

TECHNICAL FIELD

The present invention relates to a photosensitive composition, an insulating film and a color filter formed by using the photosensitive composition, a display device including the insulating film or the color filter, and a compound to be suitably mixed in the photosensitive composition as a photopolymerization initiator.

BACKGROUND ART

A display device such as a liquid crystal display has a structure in which a liquid crystal layer is interposed between two substrates formed with a pair of electrodes facing each other. A color filter composed of red (R), green (G), and blue (B) pixel regions is formed inside one substrate. In this color filter, a black matrix is usually formed so as to define each of red, green, and blue pixel regions.

In general, the color filter is produced by a lithographic method. First, a black photosensitive composition is applied on a substrate, dried, exposed, and then developed to form a black matrix. Then, coating, drying, exposure, and development are repeated every photosensitive composition of each color of red, green, and blue, and each pixel region is formed at a specific position to produce a color filter.

In recent years, there have been trials made for further improving contrast of an image to be displayed on a liquid crystal display by improving light shielding property due to a black matrix in the production of a liquid crystal display. For this purpose, there is a need for a photosensitive composition for formation of a black matrix to contain a large amount of a light shielding agent. However, if the photosensitive composition contains a large amount of the light shielding agent, it becomes difficult for light for curing the photosensitive composition to reach the bottom of a film of the photosensitive composition applied on a substrate when the film is exposed to light, leading to undercure associated with significant deterioration in sensitivity of a curable composition.

In the photosensitive composition, a photopolymerization initiator contained as a portion of the components generates radicals upon exposure. The radicals cause polymerization of a polymerizable compound contained in the photosensitive composition, leading to curing of the photosensitive composition. Thus, it has been known that sensitivity of photosensitive composition is influenced by types of the photopolymerization initiator contained therein.

With the increase of the production volume of a liquid crystal display, the production output of a color filter also has recently increased. Therefore, from the viewpoint of further improvement in productivity, there is a need for a high sensitivity photosensitive composition capable of forming a pattern at a low light exposure.

Under these circumstances, Patent Document 1 proposes, as a photopolymerization initiator capable of improving sensitivity of the photosensitive composition, an oxime ester compound having a cycloalkyl group. Examples described in Patent Document 1 specifically disclose compounds represented by the following chemical formulas (a) and (b).

[Chem. 1]

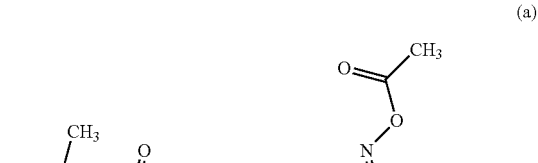

(a)

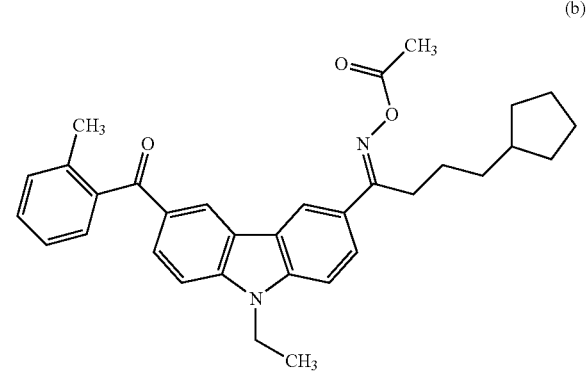

(b)

Patent Document 1: Chinese Unexamined Patent Publication No. 101508744

DISCLOSURE OF THE INVENTION

Problems to be Solved by the Invention

However, there is a need to further reduce a light exposure when a coating film made of a photosensitive composition is subjected to exposure to produce a panel for various display devices using the photosensitive composition from a viewpoint of improving productivity of the panel. It is sometimes impossible for the photosensitive composition containing the compound disclosed in Patent Document 1 to sufficiently meet these demands. Therefore, there is a need for a photosensitive composition having sensitivity which is more excellent than that of the photosensitive composition containing the compound disclosed in Patent Document 1.

In the light of the problems mentioned above, the present invention has been made and an object thereof is to provide a photosensitive composition having excellent sensitivity, an insulating film formed by using the photosensitive composition, a color filter formed by using the photosensitive composition, a display device including the insulating film or the color filter, and a compound to be suitably mixed in the photosensitive composition as a photopolymerization initiator.

Means for Solving the Problems

The present inventors have found that the problems mentioned above can be solved by allowing (B) a photopolymerization initiator, in a photosensitive composition including (A) a photopolymerizable compound and (B) a photopolymerization initiator, to contain an oxime ester compound of a specific structure having a 9,9-disubstituted fluorenyl group, leading to completion of the present invention. Specifically, the present invention provides the following.

A first aspect of the present invention is directed to a photosensitive composition including (A) a photopolymerizable compound and (B) a photopolymerization initiator, in which the photopolymerization initiator (B) contains a compound represented by the following formula (1):

[Chem. 2]

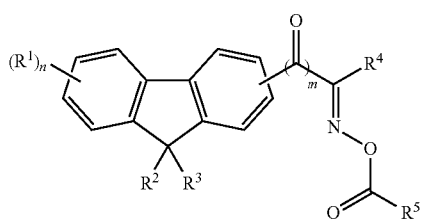

(1)

in which $R^1$ is a hydrogen atom, a nitro group, or a monovalent organic group; $R^2$ and $R^3$ each are a chain alkyl group which may have a substituent, a cyclic organic group which may have a substituent, or a hydrogen atom; $R^2$ and $R^3$ may be bonded to one another to form a ring; $R^4$ is a monovalent organic group; $R^5$ is a hydrogen atom, an alkyl group having 1 to 11 carbon atoms which may have a substituent, or an aryl group which may have a substituent; n is an integer of 0 to 4; and m is 0 or 1.

A second aspect of the present invention is directed to an insulating film formed by using the photosensitive composition according to the first aspect.

A third aspect of the present invention is directed to a color filter formed by using a photosensitive composition containing (C) a coloring agent among the photosensitive composition according to the first aspect.

A fourth aspect of the present invention is directed to a display device including the insulating film according to the second aspect or the color filter according to the third aspect.

A fifth aspect of the present invention is directed to a compound represented by the following formula (1):

[Chem. 3]

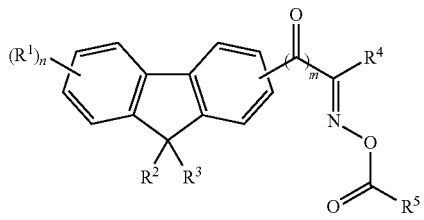

(1)

in which $R^1$ is a hydrogen atom, a nitro group, or a monovalent organic group; $R^2$ and $R^3$ each are a chain alkyl group which may have a substituent, a cyclic organic group which may have a substituent, or a hydrogen atom; $R^2$ and $R^3$ may be bonded to one another to form a ring; $R^4$ is a monovalent organic group; $R^5$ is a hydrogen atom, an alkyl group having 1 to 11 carbon atoms which may have a substituent, or an aryl group which may have a substituent; n is an integer of 0 to 4; and m is 0 or 1.

A sixth aspect of the present invention is directed to a compound represented by the following formula (2):

[Chem. 4]

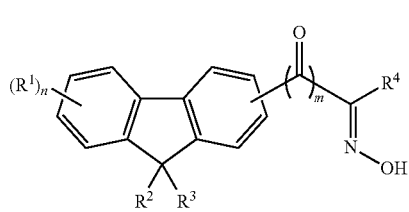

(2)

in which $R^1$ is a hydrogen atom, a nitro group, or a monovalent organic group; $R^2$ and $R^3$ each are a chain alkyl group which may have a substituent, a cyclic organic group which may have a substituent, or a hydrogen atom; $R^2$ and $R^3$ may be bonded to one another to form a ring; $R^4$ is a monovalent organic group; n is an integer of 0 to 4; and m is 0 or 1.

A seventh aspect of the present invention is directed to a method for producing a compound represented by the formula (1-4), in which the method includes the steps of: introducing an acyl group represented by —CO—$R^4$ into a compound represented by the following formula (1-1):

[Chem. 5]

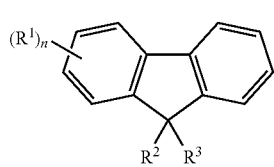

(1-1)

by a Friedel-Crafts acylation reaction to obtain a compound represented by the following formula (1-3):

[Chem. 6]

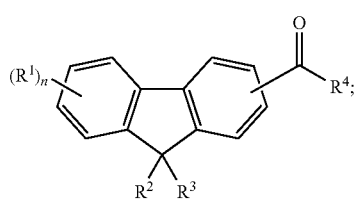

(1-3)

and converting a group represented by —CO—R⁴ in the compound represented by the formula (1-3) into a group represented by —C(=N—OH)—R⁴ to obtain a compound represented by the following formula (1-4):

[Chem. 7]

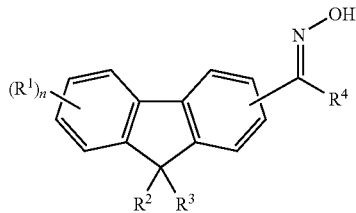

(1-4)

in which, in the formulas (1-1), (1-3), and (1-4), $R^1$ is a hydrogen atom, a nitro group, or a monovalent organic group; $R^2$ and $R^3$ each are a chain alkyl group which may have a substituent, a cyclic organic group which may have a substituent, or a hydrogen atom; $R^2$ and $R^3$ may be bonded to one another to form a ring; Hal is a halogen atom; $R^4$ is a monovalent organic group; n is an integer of 0 to 4; and $R^4$(s) included in the formula (1-3) and the formula (1-4) may be the same as or different from each other.

An eighth aspect of the present invention is directed to a method for producing a compound represented by the formula (2-3), in which the method includes the steps of: introducing an acyl group represented by —CO—CH₂—R⁴ into a compound represented by the following formula (1-1):

[Chem. 8]

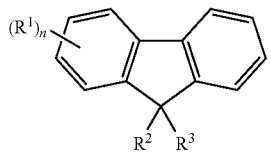

(1-1)

by a Friedel-Crafts acylation reaction to obtain a compound represented by the following formula (2-1):

[Chem. 9]

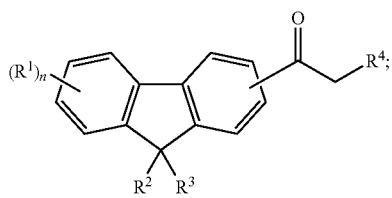

(2-1)

and oximating a methylene group existing between $R^4$ and a carbonyl group in the compound represented by the formula (2-1) to obtain a compound represented by the following formula (2-3):

[Chem. 10]

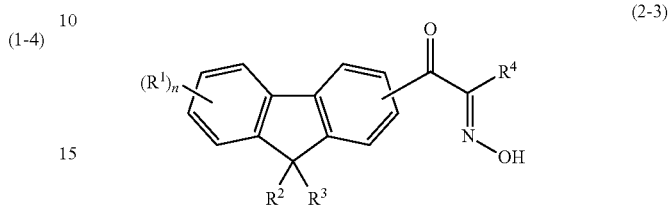

(2-3)

in which, in the formulas (1-1), (2-1), and (2-3), $R^1$ is a hydrogen atom, a nitro group, or a monovalent organic group; $R^2$ and $R^3$ each are a chain alkyl group which may have a substituent, a cyclic organic group which may have a substituent, or a hydrogen atom; $R^2$ and $R^3$ may be bonded to one another to form a ring; Hal is a halogen atom; $R^4$ is a monovalent organic group; n is an integer of 0 to 4; and $R^4$(s) included in the formula (2-1) and the formula (2-3) may be the same as or different from each other.

A ninth aspect of the present invention is directed to a method for producing the compound according to the fifth aspect, in which the method includes the step of converting an oxime group included in the following formula (2) into an oxime ester group represented by =N—O—COR⁵:

[Chem. 11]

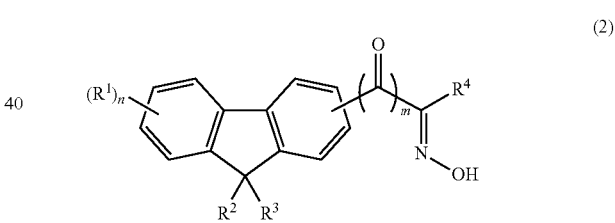

(2)

in which $R^1$ is a hydrogen atom, a nitro group, or a monovalent organic group; $R^2$ and $R^3$ each are a chain alkyl group which may have a substituent, a cyclic organic group which may have a substituent, or a hydrogen atom; $R^2$ and $R^3$ may be bonded to one another to form a ring; $R^4$ is a monovalent organic group; n is an integer of 0 to 4; and m is 0 or 1; and $R^5$ is a hydrogen atom, an alkyl group having 1 to 11 carbon atoms which may have a substituent, or an aryl group which may have a substituent.

Effects of the Invention

According to the present invention, it is possible to provide a photosensitive composition having excellent sensitivity, an insulating film formed by using the photosensitive composition, a color filter formed by using the photosensitive composition, a display device including the insulating film or the color filter, and a compound to be suitably mixed in the photosensitive composition as a photopolymerization initiator.

BRIEF DESCRIPTION OF THE DRAWINGS

FIG. 1 is a schematic diagram showing a cross-sectional shape in a width direction of a pattern formed by using a photosensitive composition, in which

PREFERRED MODE FOR CARRYING OUT THE INVENTION

<<Photosensitive Composition>>

Figure 1A:
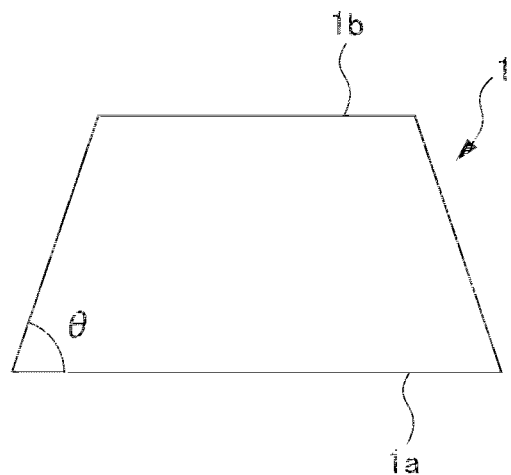
FIG. 1A is a diagram showing a cross-sectional shape of a conventional pattern and FIG. 1B is a diagram showing a cross-sectional shape of a pattern in which an undercut 21 occurred.

The photosensitive composition of the present invention includes (A) a photopolymerizable compound and (B) a photopolymerization initiator. The photopolymerization initiator (B) includes an oxime ester compound of a specific structure having a 9,9-disubstituted fluorenyl group. The photosensitive composition may include (C) a coloring agent, or may include (D) an alkali-soluble resin. Components contained in a photosensitive composition and a method for preparing the photosensitive composition will be sequentially described below.

<(A) Photopolymerizable Compound>

There is no particular limitation on the photopolymerizable compound (A) (hereinafter also referred to as the component (A)) contained in the photosensitive composition according to the present invention, and it is possible to use a conventionally known photopolymerizable compound. Among these, a resin or monomer having an ethylenically unsaturated group is preferable, and it is more preferable to use them in combination. Use of a resin having an ethylenically unsaturated group in combination with a monomer having an ethylenically unsaturated group enables an improvement in curability of the photosensitive composition, thus making it easy to form a pattern.

[Resin Having Ethylenically Unsaturated Group]

Examples of the resin having an ethylenically unsaturated group include oligomers obtained by polymerization of (meth)acrylic acid, fumaric acid, maleic acid, monomethyl fumarate, monoethyl fumarate, 2-hydroxyethyl (meth)acrylate, ethylene glycol monomethyl ether (meth)acrylate, ethylene glycol monoethyl ether (meth)acrylate, glycerol (meth)acrylate, (meth)acrylamide, acrylonitrile, methacrylonitrile, methyl (meth)acrylate, ethyl (meth)acrylate, isobutyl (meth)acrylate, 2-ethylhexyl (meth)acrylate, benzyl (meth)acrylate, ethylene glycol di(meth)acrylate, diethylene glycol di(meth)acrylate, triethylene glycol di(meth)acrylate, tetraethylene glycol di(meth)acrylate, butylene glycol di(meth)acrylate, propylene glycol di(meth)acrylate, trimethylolpropane tri(meth)acrylate, tetramethylolpropane tetra(meth)acrylate, pentaerythritol tri(meth)acrylate, pentaerythritol tetra(meth)acrylate, dipentaerythritol penta(meth)acrylate, dipentaerythritol hexa(meth)acrylate, 1,6-hexanediol di(meth)acrylate, cardoepoxy diacrylate, and the like; polyester (meth)acrylate, which is obtained by reacting a polyester prepolymer obtained by fusing polyhydric alcohols with a monobasic acid or a polybasic acid, with (meth)acrylic acid; polyurethane (meth)acrylate obtained by reacting a polyol with a compound having two isocyanate groups, followed by a reaction with (meth)acrylic acid; and an epoxy (meth)acrylate resin obtained by reacting an epoxy resin such as a bisphenol A type epoxy resin, a bisphenol F type epoxy resin, a bisphenol S type epoxy resin, a phenol or cresol novolac type epoxy resin, a resol type epoxy resin, a triphenolmethane type epoxy resin, a polycarboxylic acid polyglycidyl ester, a polyolpolyglycidyl ester, an aliphatic or alicyclic epoxy resin, an amine epoxy resin, or a dihydroxybenzene type epoxy resin with (meth)acrylic acid. It is also possible to suitably use a resin obtained by reacting an epoxy (meth)acrylate resin with a polybasic anhydride. As used herein, "(meth)acryl" means "acryl or methacryl".

It is possible to suitably use, as the resin having an ethylenically unsaturated group, a resin obtained by reacting a reaction product of an epoxy compound and an unsaturated group-containing carboxylic acid compound with a polybasic anhydride.

Among these, a compound represented by the following formula (a1) is preferable. This compound represented by the formula (a1) is preferable because of its high photocurability.

[Chem. 12]

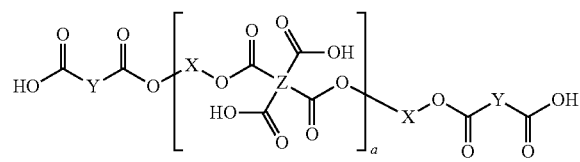

(a1)

In the above formula (a1), X represents a group represented by the following formula (a2).

[Chem. 13]

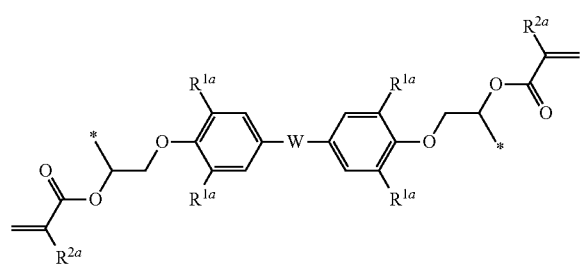

(a2)

In the above formula (a2), $R^{1a}$ each independently represents a hydrogen atom, a hydrocarbon group having 1 to 6 carbon atoms, or a halogen atom, $R^{2a}$ each independently represents a hydrogen atom or methyl group, and W represents a single bond or a group represented by a structural formula (a3) below. In the formula (a2) and the structural formula (a3), "*" means the end of a bond of a divalent group.

[Chem. 14]

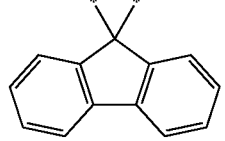

(a3)

In the above formula (a1), Y represents a residue in which an anhydride group (—CO—O—CO—) is removed from dicarboxylic anhydride. Examples of the dicarboxylic anhydride include maleic anhydride, succinic anhydride, itaconic anhydride, phthalic anhydride, tetrahydrophthalic anhydride, hexahydrophthalic anhydride, methyl endo-methylene-tetrahydrophthalic anhydride, chlorendic anhydride, methyltetrahydrophthalic anhydride, glutaric anhydride, and the like.

In the above formula (a1), Z represents a residue in which two anhydride groups are removed from tetracarboxylic dianhydride. Examples of the tetracarboxylic dianhydride include pyromellitic anhydride, benzophenonetetracarboxylic dianhydride, biphenyltetracarboxylic dianhydride, biphenyl ether tetracarboxylic dianhydride, and the like. In the above formula (a1), a represents an integer of 0 to 20.

An acid value of the resin having an ethylenically unsaturated group is preferably 10 to 150 mgKOH/g, and more preferably 70 to 110 mgKOH/g, in terms of the solid content of the resin. It is preferable that sufficient solubility in developing solution can be obtained by adjusting the acid value at 10 mgKOH/g or more. It is preferable that sufficient curability can be obtained and surface property can be improved by adjusting the acid value at 150 mgKOH/g or less.

A mass average molecular weight of the resin having an ethylenically unsaturated group is preferably 1,000 to 40,000, and more preferably 2,000 to 30,000. It is preferable that satisfactory heat resistance and film strength can be obtained by adjusting the mass average molecular weight at 1,000 or more. It is preferable that satisfactory developability can be obtained by adjusting the mass average molecular weight at 40,000 or less.

[Monomer Having Ethylenically Unsaturated Group]

The monomer having an ethylenically unsaturated group includes a monofunctional monomer and a polyfunctional monomer. The monofunctional monomer and the polyfunctional monomer will be sequentially described below.

Examples of the monofunctional monomer include (meth)acrylamide, methylol(meth)acrylamide, methoxymethyl (meth)acrylamide, ethoxymethyl(meth)acrylamide, propoxymethyl(meth)acrylamide, butoxymethoxymethyl (meth)acrylamide, N-methylol(meth)acrylamide, N-hydroxymethyl(meth)acrylamide, (meth)acrylic acid, fumaric acid, maleic acid, maleic anhydride, itaconic acid, itaconic anhydride, citraconic acid, citraconic anhydride, crotonic acid, 2-acrylamide-2-methylpropanesulfonic acid, tert-butylacrylamidesulfonic acid, methyl (meth)acrylate, ethyl (meth)acrylate, butyl (meth)acrylate, 2-ethylhexyl (meth) acrylate, cyclohexyl (meth)acrylate, 2-hydroxyethyl (meth) acrylate, 2-hydroxypropyl (meth)acrylate, 2-hydroxybutyl (meth)acrylate, 2-phenoxy-2-hydroxypropyl (meth)acrylate, 2-(meth)acryloyloxy-2-hydroxypropyl phthalate, glycerin mono(meth)acrylate, tetrahydrofurfuryl (meth)acrylate, dimethylamino (meth)acrylate, glycidyl (meth)acrylate, 2,2, 2-trifluoroethyl (meth)acrylate, 2,2,3,3-tetrafluoropropyl (meth)acrylate, a half (meth)acrylate of a phthalic acid derivative, and the like. These monofunctional monomers may be used alone, or two or more monofunctional monomers may be used in combination.

Examples of the polyfunctional monomer include ethylene glycol di(meth)acrylate, diethylene glycol di(meth)acrylate, tetraethylene glycol di(meth)acrylate, propylene glycol di(meth)acrylate, polypropylene glycol di(meth)acrylate, butylene glycol di(meth)acrylate, neopentyl glycol di(meth) acrylate, 1,6-hexane glycol di(meth)acrylate, trimethylolpropane tri(meth)acrylate, glycerin di(meth)acrylate, pentaerythritol triacrylate, pentaerythritol tetraacrylate, dipentaerythritol pentaacrylate, dipentaerythritol hexaacrylate, pentaerythritol di(meth)acrylate, pentaerythritol tri (meth)acrylate, pentaerythritol tetra(meth)acrylate, dipentaerythritol penta(meth)acrylate, dipentaerythritol hexa (meth)acrylate, 2,2-bis(4-(meth)acryloxydiethoxyphenyl) propane, 2,2-bis(4-(meth)acryloxypolyethoxyphenyl) propane, 2-hydroxy-3-(meth)acryloyloxypropyl (meth) acrylate, ethylene glycol diglycidyl ether di(meth)acrylate, diethylene glycol diglycidyl ether di(meth)acrylate, phthalic acid diglycidyl ester di(meth)acrylate, glycerin triacrylate, glycerin polyglycidyl ether poly (meth)acrylate, urethane (meth)acrylate (i.e., tolylene diisocyanate), a reaction product of trimethylhexamethylene diisocyanate, hexamethylene diisocyanate, and 2-hydroxyethyl (meth)acrylate, methylenebis(meth)acrylamide, (meth)acrylamide methylene ether, a polyfunctional monomer such as a fused product of polyhydric alcohol and N-methylol(meth)acrylamide, triacryl formal, and the like. These polyfunctional monomers may be used alone, or two or more polyfunctional monomers may be used in combination.

The content of the photopolymerizable compound as the component (A) is preferably 10 to 99.9 parts by mass based on 100 parts by mass of the total solid content of the photosensitive composition. It is easy to form a film having excellent heat resistance, chemical resistance, and mechanical strength by adjusting the content of the component (A) at 10 parts by mass or more based on 100 parts by mass of the total solid content using the photosensitive composition.

<(B) Photopolymerization Initiator>

The photosensitive composition according to the present invention includes (B) a photopolymerization initiator (hereinafter also referred to as the component (B)) containing a compound represented by the following formula (1). The photosensitive composition of the present invention is extremely excellent in sensitivity because of containing the compound represented by the following formula (1) as a photopolymerization initiator (B). Therefore, use of the photosensitive composition of the present invention enables formation of a pattern having a desired shape at a low light exposure. Use of the photosensitive composition according to the present invention having excellent sensitivity suppresses pattern detachment during formation of a pattern, thus making it possible to suppress irregularities generated on edges of a pattern when a line pattern is formed.

When a pattern is formed using a photopolymerization initiator containing no coloring agent, transparency of the pattern may deteriorate by subjecting the pattern formed using a photosensitive composition to post-baking, depending on the type of the photopolymerization initiator. However, when using a photosensitive composition containing a compound represented by the following formula (1) as the photopolymerization initiator (B), deterioration of transparency of a pattern due to heating is less likely to occur.

Particularly, when the photosensitive composition contains a light shielding agent as (C) a coloring agent mentioned below, there arises a problem that the bottom of a coating film of the photosensitive composition is not easily cured due to an influence of the light shielding agent, so that undercut is likely to occur in a pattern to be formed.

For example, when a pattern of a line-shaped black matrix is formed by using the photosensitive composition, as shown in FIG. 1A, it is generally desired that a cross-section 1, which is a cross-section in a width direction of the pattern, has a trapezoidal shape in which a width of a top side 1b is slightly narrower than that of a bottom side 1a. At this time, an angle θ between the cross-section 1 of the pattern and a color filter substrate (not shown) becomes an acute angle close to 90°.

Figure 1B:
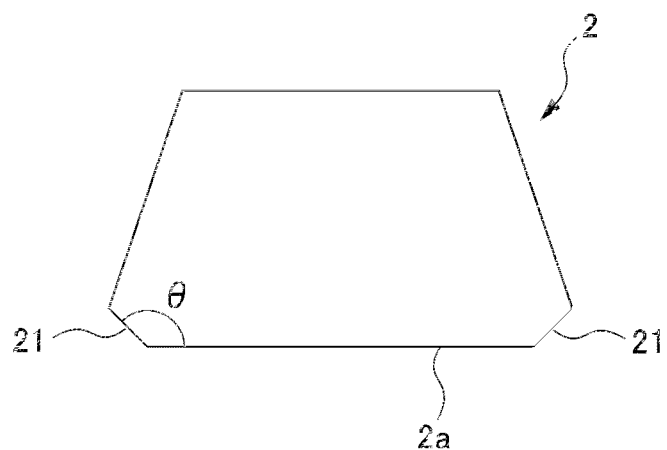

However, when a black matrix is formed by using a conventional photosensitive composition containing a light shielding agent, as shown in FIG. 1B, the bottom portion of the pattern may be sometimes dissolved during development, so that undercut 21 occurs at both ends of the bottom side 2a in a cross-section 2 which is cross-section in a width direction of the pattern. At this time, an angle θ between the cross-section 2 of the pattern and a substrate (not shown) becomes an obtuse angle.

If undercut occurs in the pattern formed by using the photosensitive composition containing a light shielding agent, for example, there arises a problem that in creating a display device, image quality deteriorates due to bubbles remaining in the undercut portion when the display device is produced by using such a pattern as a black matrix. However, when the photosensitive composition includes the photopolymerization initiator (B) containing a compound represented by the following formula (1), together with the coloring agent (C) as the light shielding agent, it is possible to suppress undercut from occurring in the pattern formed by using such a photosensitive composition.

It is desired for various patterns formed by using the photosensitive composition to have excellent water resistance that prevents detachment of the patterns from the substrate due to moisture and the like. When using the photosensitive composition including the photopolymerization initiator (B) containing a compound represented by the following formula (1), it is easy to form a pattern having excellent water resistance, which is scarcely detached from the substrate even if the pattern is contacted with water.

In the pattern formed by using the photosensitive composition, foreign materials produced due to flocculation of the initiator or resin during formation of the pattern may be sometimes included. However, when using the photosensitive composition including the photopolymerization initiator (B) containing a compound represented by the following formula (1), it is easy to form a pattern having small content of foreign materials.

[Chem. 15]

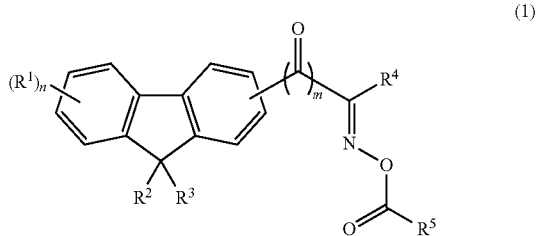

(1)

in which $R^1$ is a hydrogen atom, a nitro group, or a monovalent organic group; $R^2$ and $R^3$ each are a chain alkyl group which may have a substituent, a cyclic organic group which may have a substituent, or a hydrogen atom; $R^2$ and $R^3$ may be bonded to one another to form a ring; $R^4$ is a monovalent organic group; $R^5$ is a hydrogen atom, an alkyl group having 1 to 11 carbon atoms which may have a substituent, or an aryl group which may have a substituent; n is an integer of 0 to 4; and m is 0 or 1.

In the formula (1), $R^1$ is a hydrogen atom, a nitro group, or a monovalent organic group. $R^1$ is bonded to a 6-membered aromatic ring, which is different from a 6-membered aromatic ring to be bonded to a group represented by —(CO)$_m$—, on a fluorene ring in the formula (1). In the formula (1), a binding site for a fluorene ring of $R^1$ is not particularly limited. When the compound represented by the formula (1) has one or more $R^1$(s), one of one or more $R^1$(s) is preferably bonded at the 2-position in the fluorene ring since it is easy to synthesize the compound represented by the formula (1). When plural $R^1$(s) are present, plural $R^1$(s) may be the same as or different from each other.

When $R^1$ is an organic group, $R^1$ is not particularly limited as long as the object of the present invention is not inhibited, and is appropriately selected from various organic groups. When $R^1$ is an organic group, suitable examples include an alkyl group, an alkoxy group, an cycloalkyl group, an cycloalkoxy group, a saturated aliphatic acyl group, an alkoxycarbonyl group, a saturated aliphatic acyloxy group, a phenyl group which may have a substituent, a phenoxy group which may have a substituent, a benzoyl group which may have a substituent, a phenoxycarbonyl group which may have a substituent, a benzoyloxy group which may have a substituent, a phenylalkyl group which may have a substituent, a naphthyl group which may have a substituent, a naphthoxy group which may have a substituent, a naphthoyl group which may have a substituent, a naphthoxycarbonyl group which may have a substituent, a naphthoyloxy group which may have a substituent, a naphthylalkyl group which may have a substituent, a heterocyclylic group which may have a substituent, a heterocyclylcarbonyl group which may have a substituent, an amino group substituted with one or more organic groups, a morpholin-1-yl group, and a piperazin-1-yl group.

When $R^1$ is an alkyl group, the number of carbon atoms of the alkyl group is preferably 1 to 20, and more preferably 1 to 6. When $R^1$ is an alkyl group, the alkyl group may be either one of a straight chain or branched chain alkyl group. When $R^1$ is an alkyl group, specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, and an isodecyl group. When $R^1$ is an alkyl group, the alkyl group may contain an ether bond (—O—) in the carbon chain. Examples of the alkyl group having an ether bond in the carbon chain include a methoxyethyl group, an ethoxyethyl group, a methoxyethoxyethyl group, an ethoxyethoxyethyl group, a propyloxyethoxyethyl group, and a methoxypropyl group.

When $R^1$ is an alkoxy group, the number of carbon atoms of the alkoxy group is preferably 1 to 20, and more preferably 1 to 6. When $R^1$ is an alkoxy group, the alkyl group may be either one of a straight chain or branched chain alkyl group. When $R^1$ is an alkoxy group, specific examples include a methoxy group, an ethoxy group, an n-propyloxy group, an isopropyloxy group, an n-butyloxy group, an isobutyloxy group, a sec-butyloxy group, a tert-butyloxy group, an n-pentyloxy group, an isopentyloxy group, a sec-pentyloxy group, a tert-pentyloxy group, an n-hexyloxy group, an n-heptyloxy group, an n-octyloxy group, an isooctyloxy group, a sec-octyloxy group, a tert-octyloxy group, an n-nonyloxy group, an isononyloxy group, an n-decyloxy group, and an isodecyloxy group. When $R^1$ is an alkoxy group, the alkoxy group may include an ether bond (—O—) in the carbon chain. Examples of the alkoxy group having an ether bond in the carbon chain include a methoxyethoxy group, an ethoxyethoxy group, a methoxyethoxyethoxy group, an ethoxyethoxyethoxy group, a propyloxyethoxyethoxy group, and a methoxypropyloxy group.

When $R^1$ is a cycloalkyl group or a cycloalkoxy group, the number of carbon atoms of the cycloalkyl group or cycloalkoxy group is preferably 3 to 10, and more preferably 3 to 6. When $R^1$ is a cycloalkyl group, specific examples include a cyclopropyl group, a cyclobutyl group, a cyclopentyl group, a cyclohexyl group, a cycloheptyl group, and a cyclooctyl group. When $R^1$ is a cycloalkoxy group, specific examples include a cyclopropyloxy group, a cyclobutyloxy group, a cyclopentyloxy group, a cyclohexyloxy group, a cycloheptyloxy group, and a cyclooctyloxy group.

When $R^1$ is a saturated aliphatic acyl group or a saturated aliphatic acyloxy group, the number of carbon atoms of the saturated aliphatic acyl group or saturated aliphatic acyloxy group is preferably 2 to 21, and more preferably 2 to 7. When $R^1$ is a saturated aliphatic acyl group, specific examples include an acetyl group, a propanoyl group, an n-butanoyl group, a 2-methylpropanoyl group, an n-pentanoyl group, a 2,2-dimethylpropanoyl group, an n-hexanoyl group, an n-heptanoyl group, an n-octanoyl group, an n-nonanoyl group, an n-decanoyl group, an n-undecanoyl group, an n-dodecanoyl group, an n-tridecanoyl group, an n-tetradecanoyl group, an n-pentadecanoyl group, and an and n-hexadecanoyl group. When $R^1$ is a saturated aliphatic acyloxy group, specific examples include an acetyloxy group, a propanoyloxy group, an n-butanoyloxy group, a 2-methylpropanoyloxy group, an n-pentanoyloxy group, a 2,2-dimethylpropanoyloxy group, an n-hexanoyloxy group, an n-heptanoyloxy group, an n-octanoyloxy group, an n-nonanoyloxy group, an n-decanoyloxy group, an n-undecanoyloxy group, an n-dodecanoyloxy group, an n-tridecanoyloxy group, an n-tetradecanoyloxy group, an n-pentadecanoyloxy group, and an n-hexadecanoyloxy group.

When $R^1$ is an alkoxycarbonyl group, the number of carbon atoms of the alkoxycarbonyl group is preferably 2 to 20, and more preferably 2 to 7. When $R^1$ is an alkoxycarbonyl group, specific examples include a methoxycarbonyl group, an ethoxycarbonyl group, an n-propyloxycarbonyl group, an isopropyloxycarbonyl group, an n-butyloxycarbonyl group, an isobutyloxycarbonyl group, a sec-butyloxycarbonyl group, a tert-butyloxycarbonyl group, an n-pentyloxycarbonyl group, an isopentyloxycarbonyl group, a sec-pentyloxycarbonyl group, a tert-pentyloxycarbonyl group, an n-hexyloxycarbonyl group, an n-heptyloxycarbonyl group, an n-octyloxycarbonyl group, an isooctyloxycarbonyl group, a sec-octyloxycarbonyl group, a tert-octyloxycarbonyl group, an n-nonyloxycarbonyl group, an isononyloxycarbonyl group, an n-decyloxycarbonyl group, and an isodecyloxycarbonyl group.

When $R^1$ is a phenylalkyl group, the number of carbon atoms of the phenylalkyl group is preferably 7 to 20, and more preferably 7 to 10. When $R^1$ is a naphthylalkyl group, the number of carbon atoms of the naphthylalkyl group is preferably 11 to 20, and more preferably 11 to 14. When $R^1$ is a phenylalkyl group, specific examples include a benzyl group, a 2-phenylethyl group, a 3-phenylpropyl group, and a 4-phenylbutyl group. When $R^1$ is a naphthylalkyl group, specific examples include an α-naphthylmethyl group, a β-naphthylmethyl group, a 2-(α-naphthyl)ethyl group, and a 2-(β-naphthyl)ethyl group. When $R^1$ is a phenylalkyl group or naphthylalkyl group, $R^1$ may further have a substituent on a phenyl group or a naphthyl group.

When $R^1$ is a heterocyclylic group, the heterocyclic group is a 5- or 6-membered single ring containing one or more N, S, and O, or a heterocyclylic group in which single rings are fused each other, or a single ring is fused with a benzene ring. When the heterocyclylic group is a fused ring, the number of fused ring is 3 or less. The heterocyclylic group may be any one of an aromatic group (heteroaryl group) and a non-aromatic group. Examples of the heterocycle constituting the heterocyclylic group include furan, thiophene, pyrrole, oxazole, isoxazole, thiazole, thiadiazole, isothiazole, imidazole, pyrazole, triazole, pyridine, pyrazine, pyrimidine, pyridazine, benzofuran, benzothiophene, indole, isoindole, indolizine, benzoimidazole, benzotriazole, benzoxazole, benzothiazole, carbazole, purine, quinoline, isoquinoline, quinazoline, phthalazine, cinnoline, quinoxaline, piperidine, piperazine, morpholine, piperidine, tetrahydropyran, and tetrahydrofuran. When $R^1$ is a heterocyclylic group, the heterocyclylic group may have a substituent.

When $R^1$ is a heterocyclylcarbonyl group, the heterocyclylic group included in the heterocyclylcarbonyl group is the same as that in a case where $R^1$ is a heterocyclylic group.

When $R^1$ is an amino group substituted with one or two organic groups, suitable examples of the organic group include an alkyl group having 1 to 20 carbon atoms, a cycloalkyl group having 3 to 10 carbon atoms, a saturated aliphatic acyl group having 2 to 21 carbon atoms, a phenyl group which may have a substituent, a benzoyl group which may have a substituent, a phenylalkyl group having 7 to 20 carbon atoms which may have a substituent, a naphthyl group which may have a substituent, a naphthoyl group which may have a substituent, a naphthylalkyl group having 11 to 20 carbon atoms which may have a substituent, and a heterocyclylic group. Specific examples of suitable organic group are the same as those in $R^1$. Specific examples of the amino group substituted with one or two organic group include a methylamino group, an ethylamino group, a diethylamino group, an n-propylamino group, a di-n-propylamino group, an isopropylamino group, an n-butylamino group, a di-n-butylamino group, an n-pentylamino group, an n-hexylamino group, an n-heptylamino group, an n-octylamino group, an n-nonylamino group, an n-decylamino group, a phenylamino group, a naphthylamino group, an acetylamino group, an propanoylamino group, an n-butanoylamino group, an n-pentanoylamino group, an n-hexanoylamino group, an n-heptanoylamino group, an n-octanoylamino group, an n-decanoylamino group, a benzoylamino group, an α-naphthoylamino group, and a β-naphthoylamino group.

When a phenyl group, an naphthyl group, and a heterocyclylic group included in $R^1$ further have a substituent, examples of the substituent include an alkyl group having 1 to 6 carbon atoms, an alkoxy group having 1 to 6 carbon atoms, a saturated aliphatic acyl group having 2 to 7 carbon atoms, an alkoxycarbonyl group having 2 to 7 carbon atoms, a saturated aliphatic acyloxy group having 2 to 7 carbon atoms, a monoalkylamino group which has an alkyl group having 1 to 6 carbon atoms, a dialkylamino group which has an alkyl group having 1 to 6 carbon atoms, a morpholin-1-yl group, an piperazin-1-yl group, halogen, a nitro group, and a cyano group. When a phenyl group, a naphthyl group, and a heterocyclylic group included in $R^1$ further have a substituent, the number of substituents is not particularly limited as long as the object of the present invention is not inhibited, and is preferably 1 to 4. When a phenyl group, a naphthyl group, and a heterocyclylic group included in $R^1$ have plural substituents, plural substituents may be the same as or different each other.

Among the groups described above, $R^1$ is preferably a nitro group or a group represented by $R^6$—CO— since sensitivity tends to be improved. $R^6$ is not particularly limited as long as the object of the present invention is not inhibited, and can be selected from various organic groups. Examples of the group suitable as $R^6$ include an alkyl group having 1 to 20 carbon atoms which may have a substituent, a phenyl group which may have a substituent, a naphthyl group which may have a substituent, and a heterocyclyl group which may have a substituent. Among these groups, $R^6$ is particularly preferably a 2-methylphenyl group, a thiophen-2-yl group, or an α-naphthyl group.

Since transparency tends to be improved, $R^1$ is preferably a hydrogen atom. When $R^1$ is a hydrogen atom, and $R^4$ is a group represented by the formula (R4-2) mentioned below, transparency tends to be further improved.

In the formula (1), $R^2$ and $R^3$ each are a chain alkyl group which may have a substituent, a cyclic organic group which may have a substituent, or a hydrogen atom. $R^2$ and $R^3$ may be bonded to one another to form a ring. Among these groups, $R^2$ and $R^3$ are preferably chain alkyl groups which may have a substituent. When $R^2$ and $R^3$ are chain alkyl groups which may have a substituent, chain alkyl group may be any one of straight chain and branched chain alkyl groups.

When $R^2$ and $R^3$ are chain alkyl group having no substituent, the number of carbon atoms of the chain alkyl group is preferably 1 to 20, more preferably 1 to 10, and particularly preferably 1 to 6. When $R^2$ and $R^3$ are chain alkyl groups, specific examples include a methyl group, an ethyl group, an n-propyl group, an isopropyl group, an n-butyl group, an isobutyl group, a sec-butyl group, a tert-butyl group, an n-pentyl group, an isopentyl group, a sec-pentyl group, a tert-pentyl group, an n-hexyl group, an n-heptyl group, an n-octyl group, an isooctyl group, a sec-octyl group, a tert-octyl group, an n-nonyl group, an isononyl group, an n-decyl group, and an isodecyl group. When $R^2$ and $R^3$ are alkyl groups, the alkyl group may include an ether bond (—O—) in the carbon chain. Examples of the alkyl group having an ether bond in the carbon chain include a methoxyethyl group, an ethoxyethyl group, a methoxyethoxyethyl group, an ethoxyethoxyethyl group, a propyloxyethoxyethyl group, and a methoxypropyl group.

When $R^2$ and $R^3$ are chain alkyl groups having a substituent, the number of carbon atoms of the chain alkyl group is preferably 1 to 20, more preferably 1 to 10, and particularly preferably 1 to 6. In this case, the number of carbon atoms of the substituent is not included in the number of carbon atoms of the chain alkyl group. The chain alkyl group having a substituent is preferably a straight chain alkyl group.

There is no particular limitation on the substituent which may be possessed by the alkyl group as long as the object of the present invention is not inhibited. Suitable examples of the substituent include a cyano group, a halogen atom, a cyclic organic group, and an alkoxycarbonyl group. Examples of the halogen atom include a fluorine atom, a chlorine atom, a bromine atom, and an iodine atom. Among these, a fluorine atom, a chlorine atom, and a bromine atom are preferable. Examples of the cyclic organic group include a cycloalkyl group, an aromatic hydrocarbon group, and a heterocyclyl group. Specific examples of the cycloalkyl group are the same as suitable examples in the case where $R^1$ is a cycloalkyl group. Specific examples of the aromatic hydrocarbon group include a phenyl group, a naphthyl group, a biphenylyl group, an anthryl group, and a phenanthryl group. Specific examples of the heterocyclylic group are the same as suitable examples in the case where $R^1$ is a heterocyclyl group. When $R^1$ is an alkoxycarbonyl group, an alkoxy group contained in the alkoxycarbonyl group may be either one of straight chain or branched chain alkoxy group, and preferably a straight chain alkoxy group. The number of carbon atoms of the alkoxy group included in the alkoxycarbonyl group is preferably 1 to 10, and more preferably 1 to 6.

When the chain alkyl group has a substituent, the number of substituents is not particularly limited. The preferable number of substituents varies depending on the number of carbon atoms of the chain alkyl group. The number of substituents is typically 1 to 20, preferably 1 to 10, and more preferably 1 to 6.

When $R^2$ and $R^3$ are cyclic organic groups, the cyclic organic group may be any one of an alicyclic group and an aromatic group. Examples of the cyclic organic group include an aliphatic cyclic hydrocarbon group, an aromatic hydrocarbon group, and a heterocyclylic group. When $R^2$ and $R^3$ are cyclic organic groups, the substituent which may be possessed by the cyclic organic group is the same as that in the case where $R^2$ and $R^3$ are chain alkyl groups.

When $R^2$ and $R^3$ are aromatic hydrocarbon groups, the aromatic hydrocarbon group is preferably a phenyl group formed by bonding of plural benzene rings via a carbon-carbon bond, or a group formed by fusion of plural benzene rings. When the aromatic hydrocarbon group is a phenyl group, or a group formed by bonding or fusion of plural benzene rings, the number of benzene rings included in the aromatic hydrocarbon group is not particularly limited, and is preferably 3 or less, more preferably 2 or less, and particularly preferably 1. Suitable specific examples of the aromatic hydrocarbon group include a phenyl group, a naphthyl group, a biphenylyl group, an anthryl group, and a phenanthryl group.

When $R^2$ and $R^3$ are aliphatic cyclic hydrocarbon groups, the aliphatic cyclic hydrocarbon group may be any one of monocyclic and polycyclic hydrocarbon groups. The number of carbon atoms of the aliphatic cyclic hydrocarbon group is not particularly limited, and is preferably 3 to 20, and more preferably 3 to 10. Examples of the monocyclic cyclic hydrocarbon group include a cyclopropyl group, a cyclobutyl group, a cyclopentyl group, a cyclohexyl group, a cycloheptyl group, a cyclooctyl group, a norbornyl group, an isobornyl group, a tricyclononyl group, a tricyclodecyl group, a tetracyclododecyl group, and an adamantyl group.

When $R^2$ and $R^3$ are the heterocyclylic group, the heterocyclylic group is a 5- or 6-membered single ring including one or more N, S, and O, or a heterocyclyl group obtained by fusion of single rings, or fusion of a single ring with a benzene ring. When the heterocyclyl group is a fused ring, the number of rings to be fused is 3 or less. The heterocyclyl group may be any one of an aromatic group (heteroaryl group) and a non-aromatic group. Examples of the heterocycle constituting the heterocyclyl group include furan, thiophene, pyrrole, oxazole, isoxazole, thiazole, thiadiazole, isothiazole, imidazole, pyrazole, triazole, pyridine, pyrazine, pyrimidine, pyridazine, benzofuran, benzothiophene, indole, isoindole, indolizine, benzoimidazole, benzotriazole, benzoxazole, benzothiazole, carbazole, purine, quinoline, isoquinoline, quinazoline, phthalazine, cinnoline, quinoxaline, piperidine, piperazine, morpholine, piperidine, tetrahydropyran, and tetrahydrofuran.

$R^2$ and $R^3$ may be bonded to one another to form a ring. The group composed of the ring formed by $R^2$ and $R^3$ is preferably a cycloalkylidene group. When $R^2$ and $R^3$ are bonded to form a cycloalkylidene group, the ring constituting the cycloalkylidene group is preferably a 5- to 6-membered ring, and more preferably a 5-membered ring.

When the group formed by bonding $R^2$ and $R^3$ is a cycloalkylidene group, the cycloalkylidene group may be fused with one or more other rings. Examples of the ring which may be fused with the cycloalkylidene group include a benzene ring, a naphthalene ring, a cyclobutane ring, a cyclopentane ring, a cyclohexane ring, a cycloheptane ring, a cyclooctane ring, a furan ring, a thiophene ring, a pyrrole ring, a pyridine ring, a pyrazine ring, and a pyrimidine ring.

Examples of suitable group among $R^2$ and $R^3$ descried above include a group represented by the formula: $-A^1-A^2$. In the formula, $A^1$ is a straight chain alkylene group, and $A^2$ is an alkoxy group, a cyano group, a halogen atom, a halogenated alkyl group, a cyclic organic group, or an alkoxycarbonyl group.

The number of carbon atoms of the straight chain alkylene group for $A^1$ is preferably 1 to 10, and more preferably 1 to 6. When $A^2$ is an alkoxy group, the alkoxy group may be any one of straight chain and branched chain alkoxy groups, and preferably a straight chain alkoxy group. The number of carbon atoms of the alkoxy group is preferably 1 to 10, and more preferably 1 to 6. When $A^2$ is a halogen atom, a fluorine atom, a chlorine atom, a bromine atom, or an iodine atom is preferable, and a fluorine atom, a chlorine atom, or a bromine atom is more preferable. When $A^2$ is a halogenated alkyl group, the halogen atom included in the halogenated alkyl group is preferably a fluorine atom, a chlorine atom, a bromine atom, or an iodine atom, and more preferably a fluorine atom, a chlorine atom, or a bromine atom. The halogenated alkyl group may be any one of straight chain and branched chain halogenated alkyl groups, and preferably a straight chain halogenated alkyl group. When $A^2$ is a cyclic organic group, examples of the cyclic organic group are the same as the cyclic organic group possessed by $R^2$ and $R^3$ as the substituent. When $A^2$ is an alkoxycarbonyl group, examples of the alkoxycarbonyl group are the same as the alkoxycarbonyl group possessed by $R^2$ and $R^3$ as the substituent.

Suitable specific examples of $R^2$ and $R^3$ include alkyl groups such as an ethyl group, an n-propyl group, an n-butyl group, an n-hexyl group, an n-heptyl group, and an n-octyl group; alkoxyalkyl groups such as a 2-methoxyethyl group, a 3-methoxy-n-propyl group, a 4-methoxy-n-butyl group, a 5-methoxy-n-pentyl group, a 6-methoxy-n-hexyl group, a 7-methoxy-n-heptyl group, a 8-methoxy-n-octyl group, a 2-ethoxyethyl group, a 3-ethoxy-n-propyl group, a 4-ethoxy-n-butyl group, a 5-ethoxy-n-pentyl group, a 6-ethoxy-n-hexyl group, a 7-ethoxy-n-heptyl group, and a 8-ethoxy-n-octyl group; cyanoalkyl groups such as a 2-cyanoethyl group, a 3-cyano-n-propyl group, a 4-cyano-n-butyl group, a 5-cyano-n-pentyl group, a 6-cyano-n-hexyl group, a 7-cyano-n-heptyl group, and a 8-cyano-n-octyl group; phenylalkyl groups such as a 2-phenylethyl group, a 3-phenyl-n-propyl group, a 4-phenyl-n-butyl group, a 5-phenyl-n-pentyl group, a 6-phenyl-n-hexyl group, a 7-phenyl-n-heptyl group, and a 8-phenyl-n-octyl group; cycloalkylalkyl groups such as a 2-cyclohexylethyl group, a 3-cyclohexyl-n-propyl group, a 4-cyclohexyl-n-butyl group, a 5-cyclohexyl-n-pentyl group, a 6-cyclohexyl-n-hexyl group, a 7-cyclohexyl-n-heptyl group, a 8-cyclohexyl-n-octyl group, a 2-cyclopentylethyl group, a 3-cyclopentyl-n-propyl group, a 4-cyclopentyl-n-butyl group, a 5-cyclopentyl-n-pentyl group, a 6-cyclopentyl-n-hexyl group, a 7-cyclopentyl-n-heptyl group, and a 8-cyclopentyl-n-octyl group; alkoxycarbonylalkyl groups such as a 2-methoxycarbonylethyl group, a 3-methoxycarbonyl-n-propyl group, a 4-methoxycarbonyl-n-butyl group, a 5-methoxycarbonyl-n-pentyl group, a 6-methoxycarbonyl-n-hexyl group, a 7-methoxycarbonyl-n-heptyl group, a 8-methoxycarbonyl-n-octyl group, a 2-ethoxycarbonylethyl group, a 3-ethoxycarbonyl-n-propyl group, a 4-ethoxycarbonyl-n-butyl group, a 5-ethoxycarbonyl-n-pentyl group, a 6-ethoxycarbonyl-n-hexyl group, a 7-ethoxycarbonyl-n-heptyl group, and a 8-ethoxycarbonyl-n-octyl group; and halogenated alkyl groups such as a 2-chloroethyl group, a 3-chloro-n-propyl group, a 4-chloro-n-butyl group, a 5-chloro-n-pentyl group, a 6-chloro-n-hexyl group, a 7-chloro-n-heptyl group, a 8-chloro-n-octyl group, a 2-bromoethyl group, a 3-bromo-n-propyl group, a 4-bromo-n-butyl group, a 5-bromo-n-pentyl group, a 6-bromo-n-hexyl group, a 7-bromo-n-heptyl group, a 8-bromo-n-octyl group, a 3,3,3-trifluoropropyl group, and a 3,3,4,4,5,5,5-heptafluoro-n-pentyl group.

Among groups mentioned above, groups suitable as $R^2$ and $R^3$ are an ethyl group, an n-propyl group, an n-butyl group, an n-pentyl group, a 2-methoxyethyl group, a 2-cyanoethyl group, a 2-phenylethyl group, a 2-cyclohexylethyl group, a 2-methoxycarbonylethyl group, a 2-chloroethyl group, a 2-bromoethyl group, a 3,3,3-trifluoropropyl group, and a 3,3,4,4,5,5,5-heptafluoro-n-pentyl group.

In the same manner as $R^1$, examples of suitable organic group for $R^4$ include an alkyl group, an alkoxy group, a cycloalkyl group, a cycloalkoxy group, a saturated aliphatic acyl group, an alkoxycarbonyl group, a saturated aliphatic acyloxy group, a phenyl group which may have a substituent, a phenoxy group which may have a substituent, a benzoyl group which may have a substituent, a phenoxycarbonyl group which may have a substituent, a benzoyloxy group which may have a substituent, a phenylalkyl group which may have a substituent, a naphthyl group which may have a substituent, a naphthoxy group which may have a substituent, a naphthoyl group which may have a substituent, a naphthoxycarbonyl group which may have a substituent, a naphthoyloxy group which may have a substituent, a naphthylalkyl group which may have a substituent, a heterocyclylic group which may have a substituent, a heterocyclylcarbonyl group which may have a substituent, an amino group substituted with one or more organic groups, a morpholin-1-yl group, and a piperazin-1-yl group. Specific examples of these groups are the same as those described for $R^1$. $R^4$ is also preferably a cycloalkylalkyl group, a phenoxyalkyl group which may have a substituent on an aromatic ring, and a phenylthioalkyl group which may have a substituent on an aromatic ring. The substituent which may be possessed by a phenoxyalkyl group and phenylthioalkyl group is the same as the substituent which may be possessed by a phenyl group included in $R^1$.

Among organic groups, $R^4$ is preferably an alkyl group, a cycloalkyl group, a phenyl group which may have a substituent or cycloalkylalkyl group, or a phenylthioalkyl group which may have a substituent on an aromatic ring. The alkyl group is preferably an alkyl group having 1 to 20 carbon atoms, more preferably, an alkyl group having 1 to 8 carbon atoms, particularly preferably, an alkyl group having 1 to 4 carbon atoms, and most preferably a methyl group. Among phenyl groups which may have a substituent, a methylphenyl group is preferable and a 2-methylphenyl group is more preferable. The number of carbon atoms of the cycloalkyl group included in the cycloalkylalkyl group is preferably 5 to 10, more preferably 5 to 8, and particularly preferably 5 or 6. The number of carbon atoms of the alkylene group included in the cycloalkylalkyl group is preferably 1 to 8, more preferably 1 to 4, and particularly preferably 2. Among cycloalkylalkyl groups, a cyclopentylethyl group is preferable. The number of carbon atoms of the alkylene group which may have a substituent on an aromatic ring included in the phenylthioalkyl group, is preferably 1 to 8, more preferably 1 to 4, and particularly preferably 2. Among the phenylthioalkyl group which may have a substituent on an aromatic ring, a 2-(4-chlorophenylthio)ethyl group is preferable.

$R^4$ is also preferably a group represented by $-A^3-CO-O-A^4$. $A^3$ is a divalent organic group, preferably a divalent hydrocarbon group, and more preferably an alkylene group. $A^4$ is a monovalent organic group, and preferably a monovalent hydrocarbon group.

When $A^3$ is an alkylene group, alkylene group may be any one of straight chain and branched chain alkylene groups, and preferably a straight chain alkylene group. When $A^3$ is an alkylene group, the number of carbon atoms of the alkylene group is preferably 1 to 10, more preferably 1 to 6, and particularly preferably 1 to 4.

Suitable examples of $A^4$ include an alkyl group having 1 to 10 carbon atoms, an aralkyl group having 7 to 20 carbon atoms, and an aromatic hydrocarbon group having 6 to 20 carbon atoms. Suitable specific examples of $A^4$ include a methyl group, an ethyl group, an n-propyl group, an isopropyl group, an n-butyl group, an isobutyl group, a sec-butyl group, an tert-butyl group, an n-pentyl group, an n-hexyl group, a phenyl group, a naphthyl group, a benzyl group, a phenethyl group, an α-naphthylmethyl group, and a β-naphthylmethyl group.

Suitable specific examples of the group represented by $-A^3-CO-O-A4$ include a 2-methoxycarbonylethyl group, a 2-ethoxycarbonylethyl group, a 2-n-propyloxycarbonylethyl group, a 2-n-butyloxycarbonylethyl group, a 2-n-pentyloxycarbonylethyl group, a 2-n-hexyloxycarbonylethyl group, a 2-benzyloxycarbonylethyl group, a 2-phenoxycarbonylethyl group, a 3-methoxycarbonyl-n-propyl group, a 3-ethoxycarbonyl-n-propyl group, a 3-n-propyloxycarbonyl-n-propyl group, a 3-n-butyloxycarbonyl-n-propyl group, a 3-n-pentyloxycarbonyl-n-propyl group, a 3-n-hexyloxycarbonyl-n-propyl group, a 3-benzyloxycarbonyl-n-propyl group, and a 3-phenoxycarbonyl-n-propyl group.

While $R^4$ has been described above, $R^4$ is preferably a group represented by the following formula (R4-1) or (R4-2):

[Chem. 16]

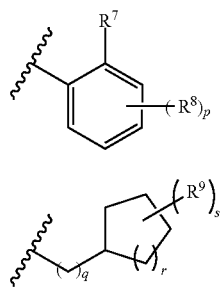

(R4-1)

(R4-2)

in which, in the formulas (R4-1) and (R4-2), $R^7$ and $R^8$ each are an organic group, p is an integer of 0 to 4; when $R^7$ and $R^8$ exist at adjacent positions on a benzene ring, $R^7$ and $R^8$ may be bonded to one another to form a ring; q is an integer of 1 to 8; r is an integer of 1 to 5; s is an integer of 0 to (r+3); and $R^9$ is an organic group.

Examples of the organic group for $R^7$ and $R^8$ in the formula (R4-1) are the same as those in $R^1$. $R^7$ is preferably an alkyl group or a phenyl group. When $R^7$ is an alkyl group, the number of carbon atoms thereof is preferably 1 to 10, more preferably 1 to 5, preferably 1 to 3, and most preferably 1. Namely, $R^7$ is most preferably a methyl group. When $R^7$ and $R^8$ are bonded to form a ring, the ring may be either one of an aromatic ring or an aliphatic ring. Suitable examples of the group represented by the formula (R4-1) in which $R^7$ and $R^8$ form a ring include a naphthalen-1-yl group, a 1,2,3,4-tetrahydronaphthalen-5-yl group, and the like. In the above formula (R4-1), p is an integer of 0 to 4, preferably 0 or 1, and more preferably 0.

In the above formula (R4-2), $R^9$ is an organic group. Examples of the organic group include the same group as the organic group described for $R^1$. Among the organic groups, an alkyl group is preferable. The alkyl group may be any one of straight chain and branched chain alkyl groups. The number of carbon atoms of the alkyl group is preferably 1 to 10, more preferably, 1 to 5, and particularly preferably 1 to 3. Preferable examples of $R^9$ include a methyl group, an ethyl group, a propyl group, an isopropyl group, a butyl group, and the like. Among these, a methyl group is more preferable.

In the above formula (R4-2), r is an integer of 1 to 5, preferably an integer of 1 to 3, and more preferably 1 or 2. In the above formula (R4-2), s is 0 to (r+3), preferably an integer of 0 to 3, more preferably an integer of 0 to 2, and particularly preferably 0. In the above formula (R4-2), q is an integer of 1 to 8, preferably an integer of 1 to 5 more preferably an integer of 1 to 3, and particularly preferably 1 or 2.

In the formula (1), $R^5$ is a hydrogen atom, an alkyl group having 1 to 11 carbon atoms which may have a substituent, or an aryl group which may have a substituent. When $R^5$ is an alkyl group, preferable examples of the substituent which may be possessed include a phenyl group, a naphthyl group, or the like. When $R^1$ is an aryl group, preferable examples of the substituent which may be possessed include an alkyl group having 1 to 5 carbon atoms, an alkoxy group, a halogen atom, or the like.

In the formula (1), preferable examples of $R^5$ include a hydrogen atom, a methyl group, an ethyl group, an n-propyl group, an isopropyl group, an n-butyl group, a phenyl group, a benzyl group, a methylphenyl group, or a naphthyl group. Among these, a methyl group or a phenyl group is more preferable.

The content of the photopolymerization initiator as the component (B) is preferably 0.001 to 30 parts by mass, more preferably 0.1 to 20 parts by mass, and further preferably 0.5 to 10 parts by mass, based on 100 parts by mass of the total solid content of the photosensitive composition.

The content of the photopolymerization initiator as the component (B) is preferably 0.1 to 50% by mass, more preferably 0.5 to 30% by mass, and further preferably 1 to 20 parts by mass, based on the sum total of the component (A) and the component (B).

The content of the compound represented by the following formula (1) may be, for example, within a range of 1 to 100% by mass, and is preferably 50% by mass or more, and more preferably 70 to 100% by mass, based on the entire component (B).

The compound represented by the formula (1) in the component (B) may be used alone, or two or more compounds may be used in combination. When using two or more compounds, the following (i) to (iii) are preferable.

(i) combination of a compound in which $R^1$ is a hydrogen atom with a compound in which $R^1$ is a nitro group (ii) combination of a compound in which $R^4$ is the formula (R4-1) with a compound in which $R^4$ is the formula (R4-2)

(iii) combination in which $R^4$ is the formula (R4-1) or the formula (R4-2) with a compound in which $R^4$ is an alkyl group having 1 to 4 carbon atoms Among these, the above combination (i) is preferable in view of an improvement in properties such as sensitivity and transmittance of a cured product, and a combination satisfying (i) and (ii) or (iii) is more preferable.

A mixing ratio (mass ratio) of the respective compounds according to the above combinations (i) to (iii) may be appropriately adjusted according to properties such as objective sensitivity. For example, the mixing ratio is preferably 1:99 to 99:1, more preferably 10:90 to 90:10, and further preferably 30:70 to 70:30.

There is no particular limitation on the method for producing a compound represented by the formula (1). The compound represented by the formula (1) is preferably produced by a method including the step of converting an oxime group (=N—OH) included in the compound represented by the following formula (2) into an oxime ester group represented by =N—O—COR$^5$. $R^5$ is the same as $R^5$ in the formula (1):

[Chem. 17]

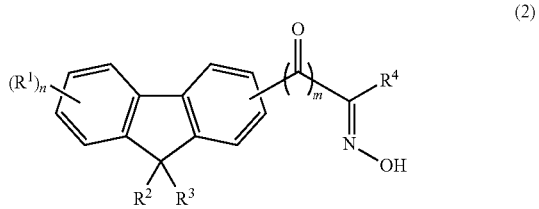

(2)

in which $R^1$, $R^2$, $R^3$, $R^4$, m, and n are the same as those in the formula (1). n is an integer of 0 to 4, and m is 0 or 1.

Therefore, a compound represented by the above formula (2) is useful as an intermediate for the synthesis of a compound represented by the formula (1).

There is no particular limitation on the method in which an oxime group (=N—OH) is converted into an oxime ester group represented by =N—O—COR$^5$. Typically, there is a method exemplified in which a hydroxyl group in an oxime group is reacted with an acylating agent capable of giving an acyl group represented by —COR$^5$. Examples of the acylating agent include an anhydride represented by $(R^5CO)_2O$, and an acid halide represented by $R^5COHal$ (Hal is a halogen atom).

The compound represented by the formula (1) can be synthesized in accordance with, for example, the scheme 1 mentioned below when m is 0. In the scheme 1, a fluorene derivative represented by the formula (1-1) mentioned below is used as a raw material. When $R^1$ is a nitro group or a monovalent organic group, a fluorene derivative represented by the formula (1-1) can be obtained by introducing a substituent $R^1$ into a fluorene derivative in which $R^2$ and $R^3$ are substituted at the 9-position according to a well-known method. When for example, $R^2$ and $R^3$ are alkyl groups, as disclosed in Japanese Unexamined Patent Application, Publication No. H06-234668, a fluorene derivative in which $R^2$ and $R^3$ are substitution at the 9-position can be obtained by reacting fluorine with an alkylating agent in an aprotic polar organic solvent in the presence of an alkali metal hydroxide. It is also possible to obtain 9,9-alkyl-substituted fluorine by adding an alkylating agent such as an alkyl halide, an aqueous solution of an alkali metal hydroxide, and a phase transfer catalyst such as tetrabutylammonium iodide or potassium tert-butoxide in an organic solvent solution of fluorine to thereby perform an alkylation reaction.

An an acyl group represented by —CO—R$^4$ is introduced into a fluorene derivative represented by the formula (1-1) by a Friedel-Crafts acylation reaction to obtain a fluorene derivative represented by the formula (1-3). An acylating agent for introducing an acyl group represented by —CO—R$^4$ may be either a halocarbonyl compound or an anhydride. The acylating agent is preferably a halocarbonyl compound represented by the formula (1-2). In the formula (1-2), Hal is a halogen atom. The position at which an acyl group is introduced on a fluorene ring can be selected by a method in which the conditions of a Friedel-Crafts reaction are appropriately changed, or the position other than the position to be acylated is protected or deprotected.

Then, a group represented by —CO—R$^4$ in the thus obtained fluorene derivative represented by the formula (1-3) is converted into a group represented by —C(=N—OH)—R$^4$ to obtain an oxime compound represented by the formula (1-4). There is no limitation in the method in which a group represented by —CO—R$^4$ is converted into a group represented by —C(=N—OH)—R$^4$, and oximation with hydroxylamine is preferable. It is possible to obtain a compound represented by the formula (1-7) shown below by reacting an oxime compound represented by the formula (1-4) with an anhydride ($(R^5CO)_2O$) represented by the following formula (1-5), or acid halide ($R^5COHal$, Hal is a halogen atom) represented by the formula (1-6) shown below.

In the formulas (1-1), (1-2), (1-3), (1-4), (1-5), (1-6), and (1-7), $R^1$, $R^2$, $R^3$, $R^4$, and $R^5$ are the same as in the formula (1).

In the scheme 1, $R^4$(s) included in the formula (1-2), the formula (1-3), and the formula (1-4) may be the same as or different from each other. Namely, $R^4$ in the formula (1-2), the formula (1-3), and the formula (1-4) may be subjected to chemical modification in the synthesis process shown as the scheme 1. Examples of the chemical modification include esterification, etherification, acylation, amidation, halogenation, substitution of a hydrogen atom in an amino group with an organic group, and the like. The chemical modification which may be applied to $R^4$ is not limited thereto.

<Scheme 1>

[Chem. 18]

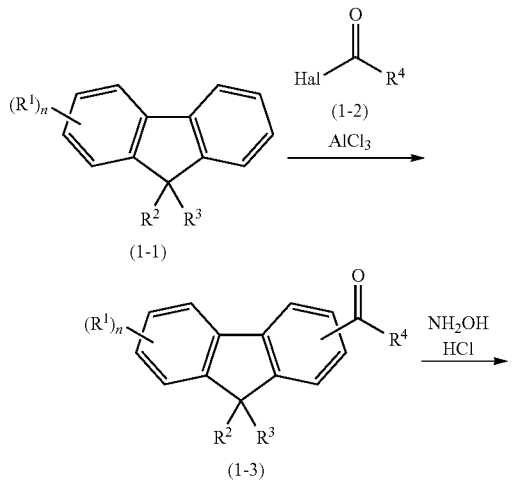

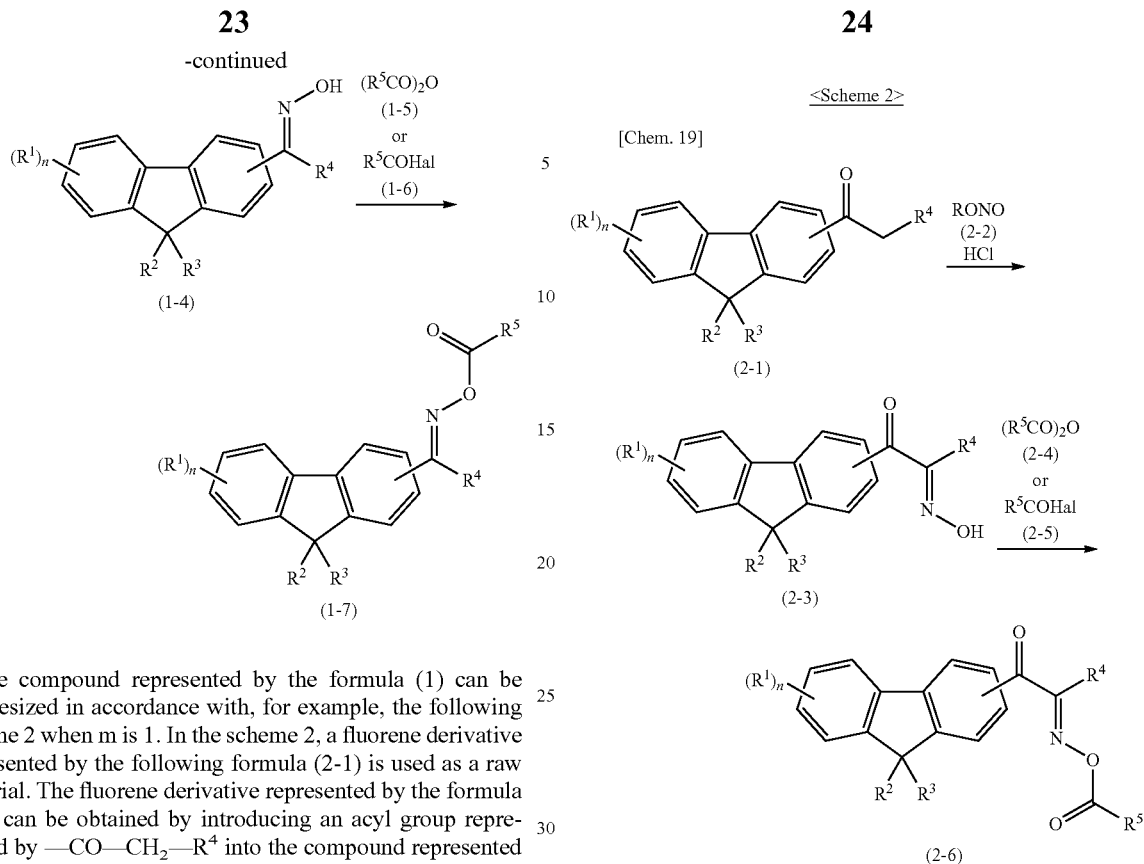

The compound represented by the formula (1) can be synthesized in accordance with, for example, the following scheme 2 when m is 1. In the scheme 2, a fluorene derivative represented by the following formula (2-1) is used as a raw material. The fluorene derivative represented by the formula (2-1) can be obtained by introducing an acyl group represented by —CO—CH$_2$—R$^4$ into the compound represented by the formula (1) by a Friedel-Crafts reaction using the same method as in the scheme 1. An acylating agent is preferably a carboxylic acid halide represented by the formula (1-8): Hal-CO—CH$_2$—R$^4$. Then, a methylene group existing between R$^4$ and a carbonyl group in the compound represented by the formula (2-1) is oximated to obtain a ketooxime compound represented by the following formula (2-3). The method of oximating a methylene group is not particularly limited, and is preferably a method in which a nitrous acid ester (RONO, R is an alkyl group having 1 to 6 carbon atoms) represented by the following formula (2-2) is reacted in the presence of hydrochloric acid. Then, a ketooxime compound represented by the following formula (2-3) is reacted with an anhydride ((R$^5$CO)$_2$O) represented by the following formula (2-4) or an acid halide (R$^5$COHal, Hal is a halogen atom) represented by the following formula (2-5), thus making it possible to obtain a compound represented by the following formula (2-6). In the following formulas (2-1), (2-3), (2-4), (2-5), and (2-6), R$^1$, R$^2$, R$^3$, R$^4$, and R$^5$ are the same as those in the formula (1).

When m is 1, there is a tendency allowing for further reducing generation of foreign materials in a pattern formed by using the photosensitive composition containing a compound represented by the formula (1).

In the scheme 2, R$^4$ (s) included in the formula (1-8), the formula (2-1), and the formula (2-3) may be the same as or different from each other. Namely, R$^4$ (s) in the formula (1-8), the formula (2-1), and the formula (2-3) may be subjected to chemical modification in the synthesis process shown as the scheme 2. Examples of the chemical modification include esterification, etherification, acylation, amidation, halogenation, substitution of a hydrogen atom in an amino group with an organic group, and the like. The chemical modification which may be applied to R$^4$ is not limited thereto.

Suitable specific examples of the compound represented by the formula (1) include the following compounds 1 to 41.

[Chem. 20]

Compound 1

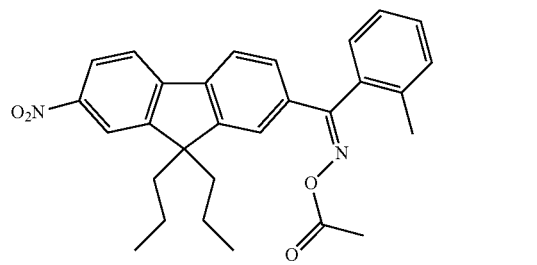

Compound 2

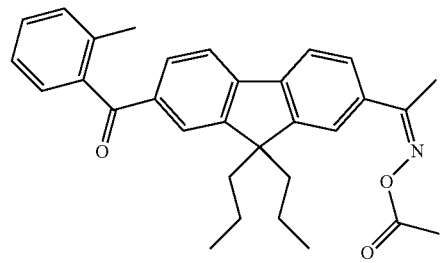

Compound 3
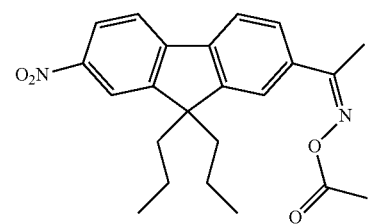
Compound 4
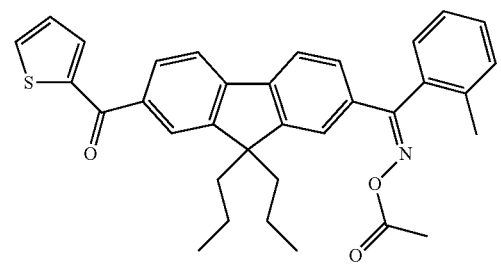
Compound 5
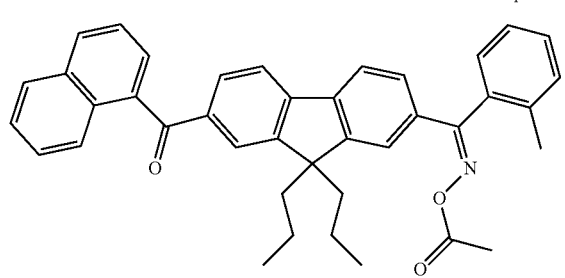
Compound 6
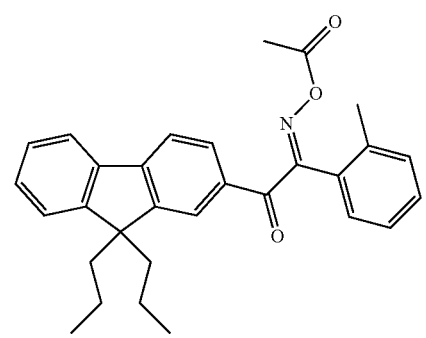
Compound 7
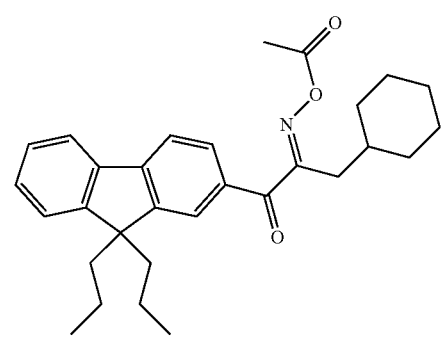
Compound 8
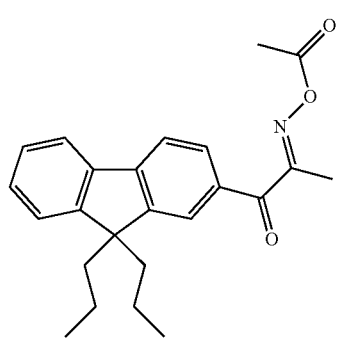
Compound 9
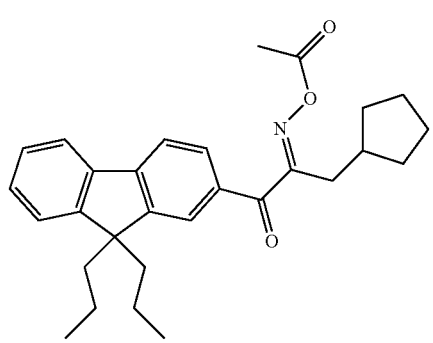
Compound 10
Compound 11
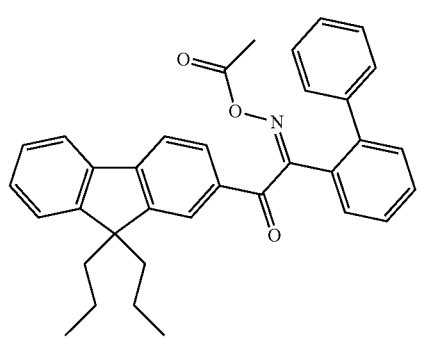

Compound 12
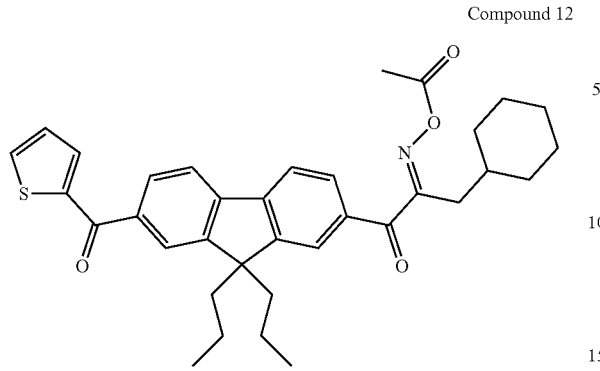
Compound 13
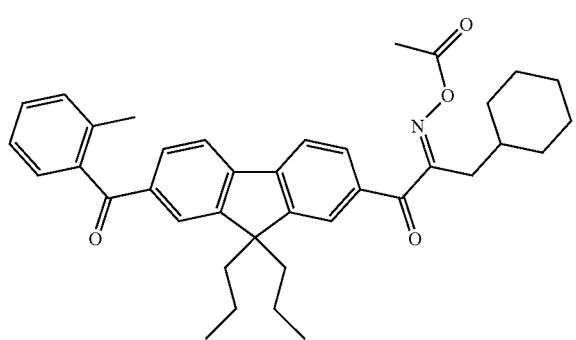
Compound 14
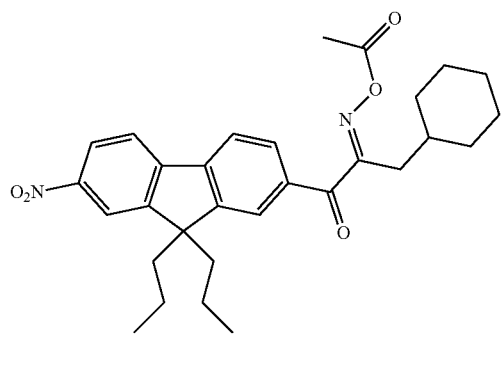
Compound 15
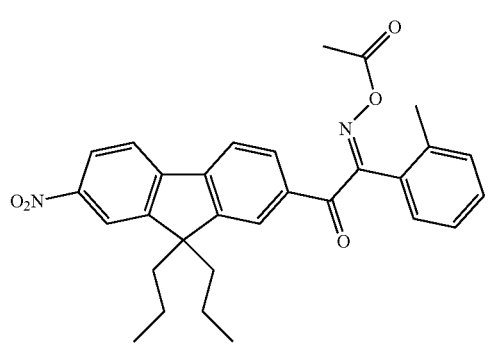
Compound 16
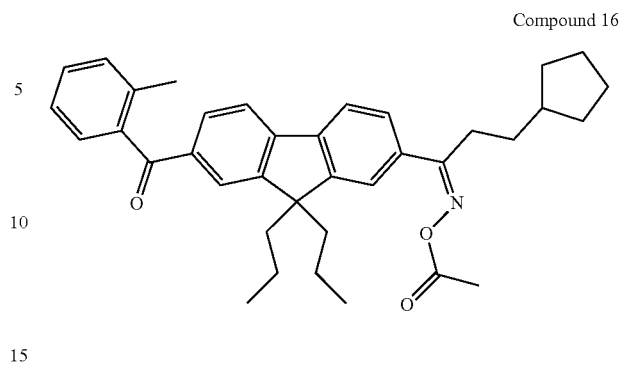
Compound 17
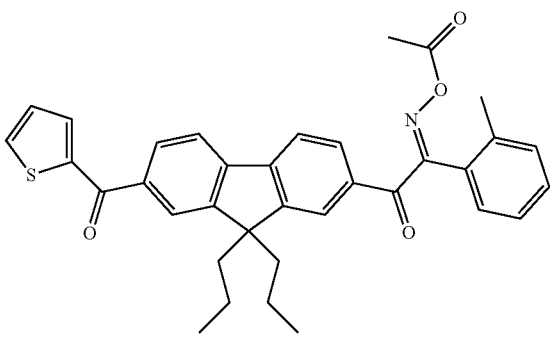
Compound 18
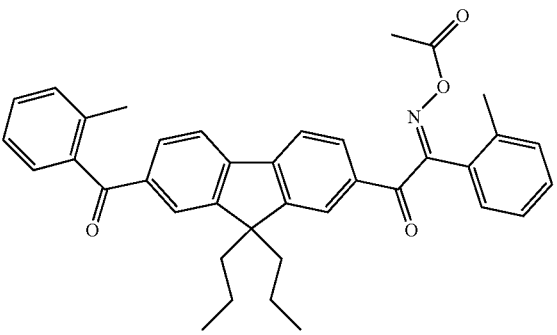
Compound 19
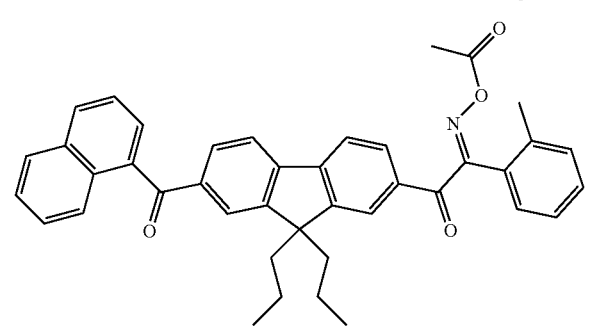

Compound 20
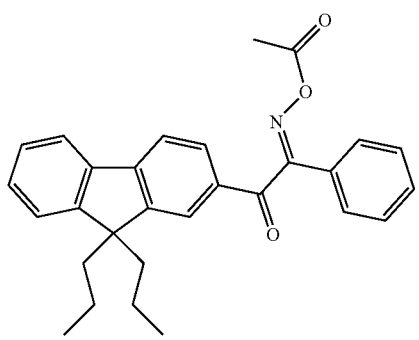
Compound 21
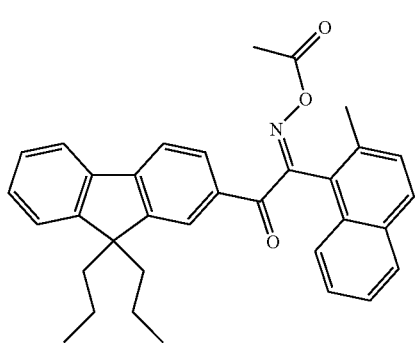
Compound 22
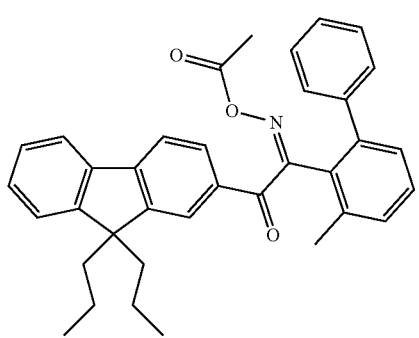
[Chem. 21]
Compound 23
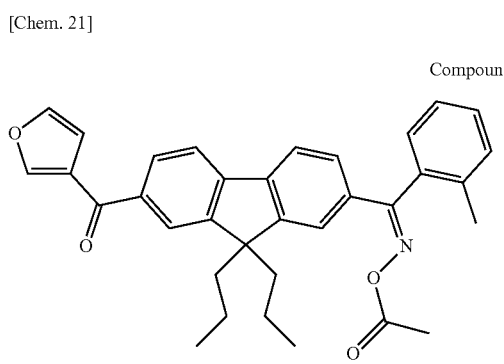
Compound 24
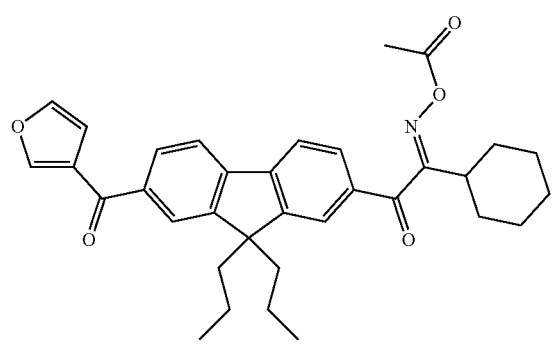
Compound 25
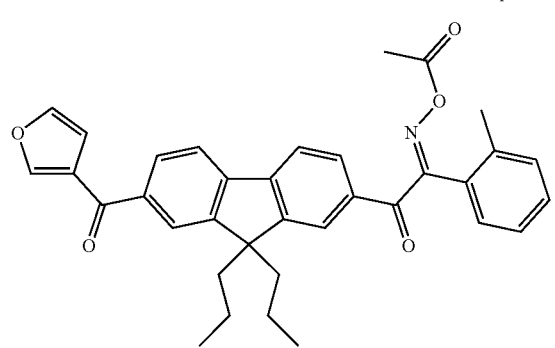
Compound 26
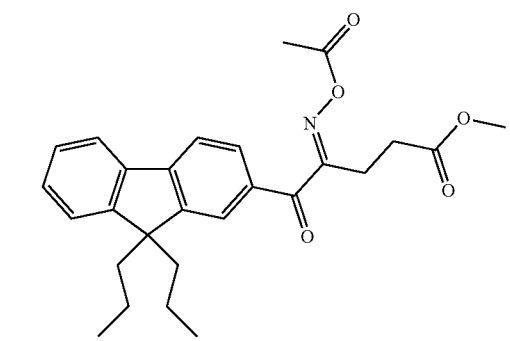
Compound 27
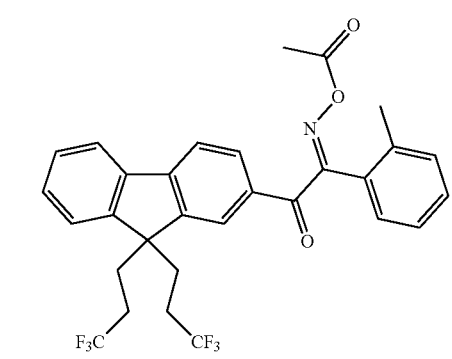

Compound 28
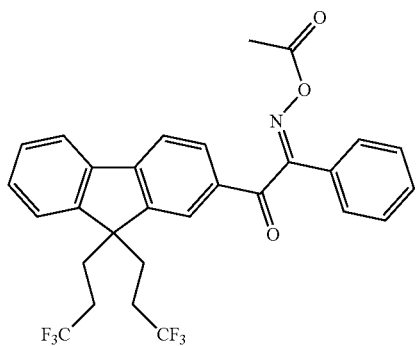
Compound 29
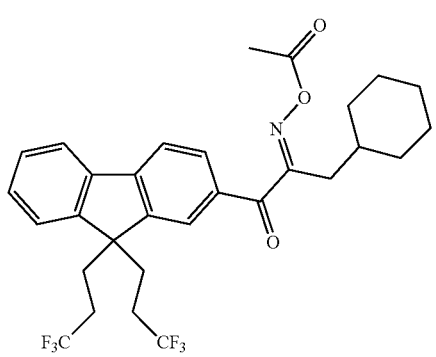
Compound 30
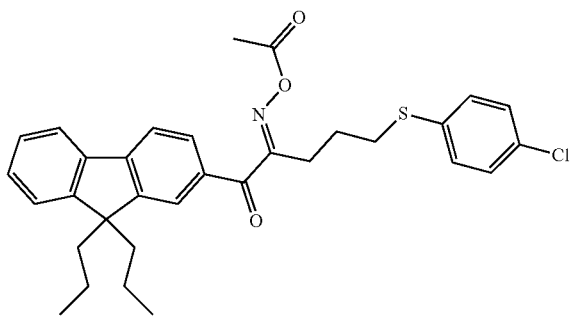
Compound 31
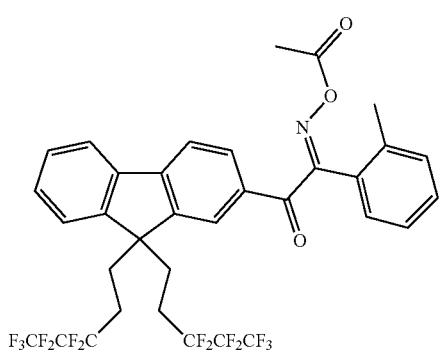
Compound 32
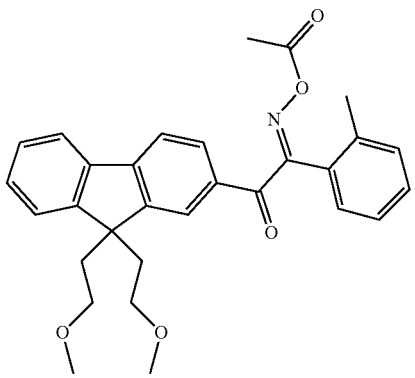
Compound 33
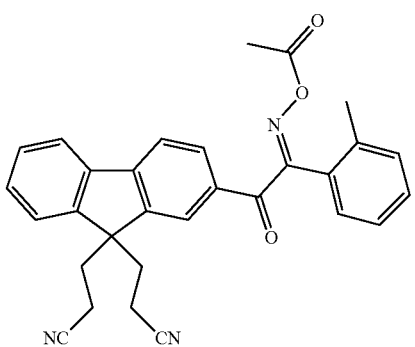
Compound 34
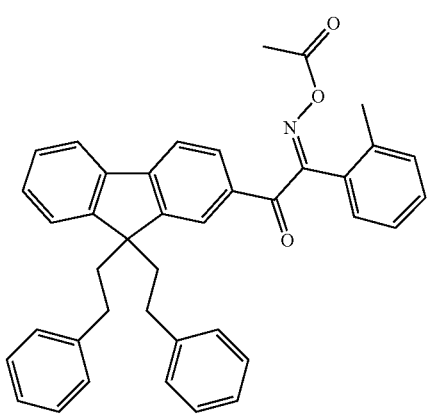
Compound 35
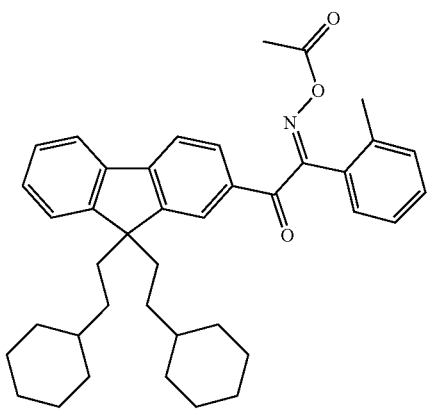

Compound 36

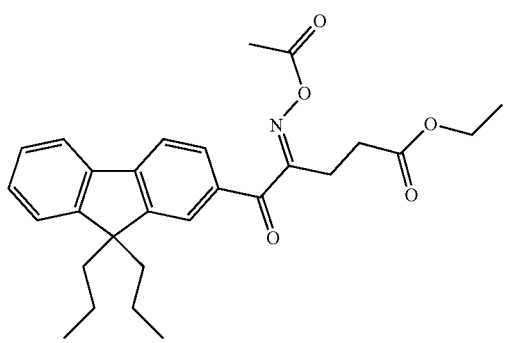

Compound 37

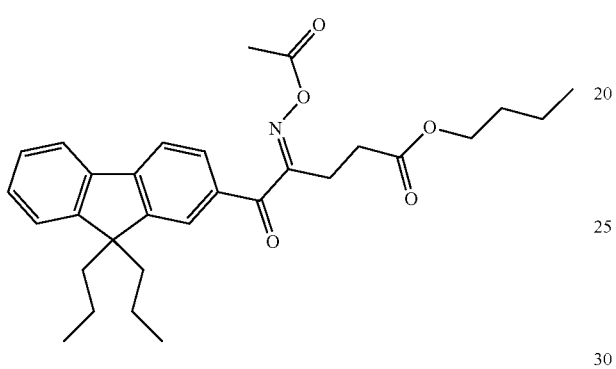

Compound 38

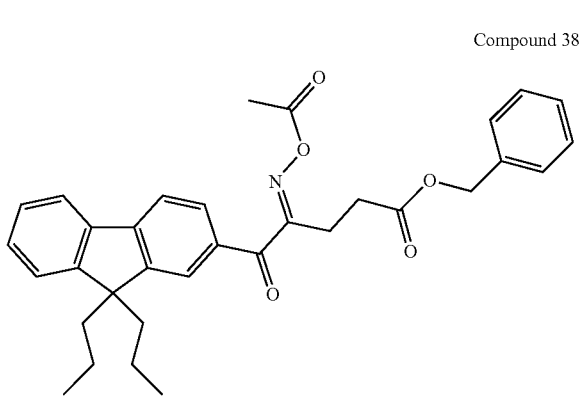

Compound 39

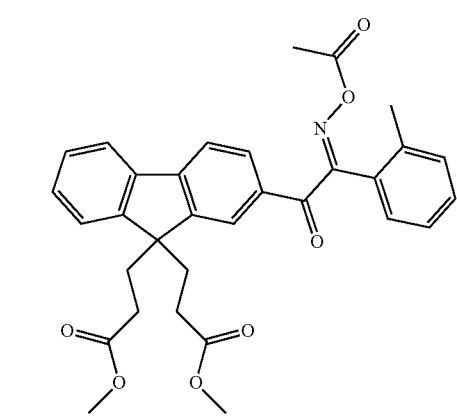

Compound 40

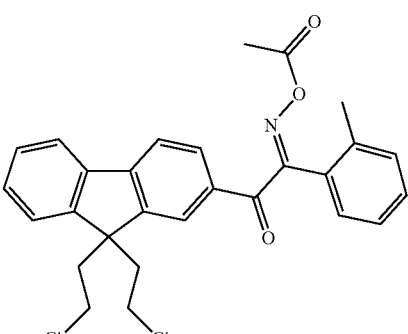

Compound 41

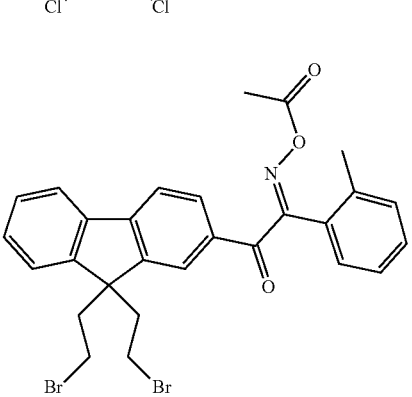

<(C) Coloring Agent>

The photosensitive composition according to the present invention may further include (C) a coloring agent. When the photosensitive composition includes the coloring agent as the component (C) for example, it can be preferably used in applications for formation of a color filter of a liquid crystal display. When the photosensitive composition according to the present invention includes a light shielding agent as the coloring agent for example, it can be preferably used in applications for formation of a black matrix in a color filter of a display device.

The coloring agent (C) contained in the photosensitive composition according to the present invention is not particularly limited, but it is preferable to use, for example, compounds which are classified into Pigment in Color Index (C.I.; published by The Society of Dyers and Colorist), and specifically those having the following color index (C.I.) numbers.

Suitable examples of the yellow pigment, which can be suitably used, include C.I. pigment yellow 1 (hereinafter, "C.I. pigment yellow" is the same, and only the numbers are listed), 3, 11, 12, 13, 14, 15, 16, 17, 20, 24, 31, 53, 55, 60, 61, 65, 71, 73, 74, 81, 83, 86, 93, 95, 97, 98, 99, 100, 101, 104, 106, 108, 109, 110, 113, 114, 116, 117, 119, 120, 125, 126, 127, 128, 129, 137, 138, 139, 147, 148, 150, 151, 152, 153, 154, 155, 156, 166, 167, 168, 175, 180, and 185.

Examples of the orange pigment, which can be suitably used, include C.I. pigment orange 1 (hereinafter, "C.I. pigment orange" is the same, and only the numbers are listed), 5, 13, 14, 16, 17, 24, 34, 36, 38, 40, 43, 46, 49, 51, 55, 59, 61, 63, 64, 71, and 73.

Examples of the violet pigment, which can be suitably used, include C.I. pigment violet 1 (hereinafter, "C.I. pigment violet" is the same, and only the numbers are listed), 19, 23, 29, 30, 32, 36, 37, 38, 39, 40, and 50.

Examples of the red pigment, which can be suitably used, include C.I. pigment red 1 (hereinafter, "C.I. pigment red" is the same, and only the numbers are listed), 2, 3, 4, 5, 6, 7, 8, 9, 10, 11, 12, 14, 15, 16, 17, 18, 19, 21, 22, 23, 30, 31, 32, 37, 38, 40, 41, 42, 48:1, 48:2, 48:3, 48:4, 49:1, 49:2, 50:1, 52:1, 53:1, 57, 57:1, 57:2, 58:2, 58:4, 60:1, 63:1, 63:2, 64:1, 81:1, 83, 88, 90:1, 97, 101, 102, 104, 105, 106, 108, 112, 113, 114, 122, 123, 144, 146, 149, 150, 151, 155, 166, 168, 170, 171, 172, 174, 175, 176, 177, 178, 179, 180, 185, 187, 188, 190, 192, 193, 194, 202, 206, 207, 208, 209, 215, 216, 217, 220, 223, 224, 226, 227, 228, 240, 242, 243, 245, 254, 255, 264, and 265.

Examples of the blue pigment, which can be suitably used, include C.I. pigment blue 1 (hereinafter, "C.I. pigment blue" is the same, and only the numbers are listed), 2, 15, 15:3, 15:4, 15:6, 16, 22, 60, 64, and 66.

Examples of the pigment with the other hue, which can be suitably used, include green pigments such as C.I. pigment green 7, C.I. pigment green 36, and C.I. pigment green 37; brown pigments such as C.I. pigment brown 23, C.I. pigment brown 25, C.I. pigment brown 26, and C.I. pigment brown 28; and black pigments such as C.I. pigment black 1 and C.I. pigment black 7.

In the case where the light shielding agent is used as the coloring agent, it is preferable to use a black pigment as the light shielding agent. Examples of the black pigment include various types of pigments irrespective of whether it is an organic substance or an inorganic substance, such as carbon black, titanium black, and a metal oxide, a composite oxide, a metal sulfide, a metal sulfate, and a metal carbonate of copper, iron, manganese, cobalt, chromium, nickel, zinc, calcium, silver, or the like. Among these, it is preferable to use the carbon black, which has a high light shielding property.

As the carbon black, known carbon black such as channel black, furnace black, thermal black, and lamp black are usable, and it is preferable to use the channel black, which is excellent in light shielding property. Also, a resin-coated carbon black may be used.

The resin coated carbon black has lower conductivity than the carbon black without resin coating resin. Therefore, when the black matrix is formed by using a photosensitive composition containing a resin-coated carbon black, it is possible to produce a low power consumption display which causes less leakage of current in a liquid crystal display device such as a liquid crystal display, and has high reliability.

Each of the above organic pigments may be appropriately added as an auxiliary pigment as required in order to adjust a color tone of the carbon black.

Further, a dispersant may be used for uniformly dispersing the coloring agent in the photosensitive resin composition. As the dispersant, polyethylene imine-based, urethane resin-based, or acryl resin-based polymer dispersants is preferably used. Particularly, in the case where the carbon black is used as the coloring agent, it is preferable to use the acryl resin-based dispersant as the dispersant.

Also, the inorganic pigments and the organic pigments may be used alone, or two or more of them may be used in combination. In the case of combined use, the organic pigment may be used within the range of 10 to 80 parts by mass, more preferably within the range of 20 to 40 parts by mass, relative to 100 parts by mass in total of the inorganic pigment and the organic pigment.

The amount of the coloring agent in the photosensitive composition may be appropriately determined according to applications of the photosensitive composition. As an example, the amount of the coloring agent is preferably 5 to 70 parts by mass, and more preferably 25 to 60 parts by mass, based on 100 parts by mass of the total solid content of the photosensitive composition. It is preferable that a black matrix and respective colored layers can be formed with the objective pattern by adjusting the amount of the coloring agent within the above range.

Particularly, in the case of forming a black matrix by using the photosensitive composition, it is preferable to adjust the amount of the light shielding agent in the photosensitive composition so that an OD value per 1 μm of film thickness of the black matrix is 4 or more. With the OD value of 4 or more per 1 μm of film thickness in the black matrix, it is possible to attain satisfactory display contrast when the photosensitive composition is used for black matrixes of liquid crystal displays.

It is preferable to add to the photosensitive composition the coloring agent as a dispersion which is obtained by dispersing the coloring agent at an appropriate concentration by using the dispersant.

<(D) Alkali-Soluble Resin>

The photosensitive composition according to the present invention may include, as a resin other than resins used as the photopolymerizable compound (A) resin, (D) an alkali-soluble resin. Alkali developability can be imparted to the photosensitive composition by mixing the alkali-soluble resin (D) in the photosensitive composition.

As used in the present specification, the alkali-soluble resin refers to a resin which forms a resin film having a film thickness of 1 μm on a substrate by a resin solution having a resin concentration of 20% by mass (solvent: propylene glycol monomethyl ether acetate), and which dissolves in a film thickness of 0.01 μm or more when immersed in an aqueous KOH solution having a concentration of 0.05% by mass for one minute.

Among alkali-soluble resins (D), a polymer of a monomer having an ethylenically unsaturated double bond is preferable since the polymer has excellent film formation properties and it is easy to adjust the properties of the resin by selection of the monomer. Examples of the monomer having an ethylenically unsaturated double bond include (meth)acrylic acid; (meth)acrylic acid ester; (meth)acrylic acid amide; crotonic acid; maleic acid, fumaric acid, citraconic acid, mesaconic acid, itaconic acid, and anhydrides of these dicarboxylic acids; allyl compounds such as allyl acetate, allyl caproate, allyl caprylate, allyl laurate, allyl palmitate, allyl stearate, allyl benzoate, allyl acetoacetate, allyl lactate, and allyloxyethanol; vinyl ethers such as hexyl vinyl ether, octyl vinyl ether, decyl vinyl ether, ethylhexyl vinyl ether, methoxyethyl vinyl ether, ethoxyethyl vinyl ether, chloroethyl vinyl ether, 1-methyl-2,2-dimethylpropyl vinyl ether, 2-ethylbutyl vinyl ether, hydroxyethyl vinyl ether, diethylene glycol vinyl ether, dimethylaminoethyl vinyl ether, diethylaminoethyl vinyl ether, butylaminoethyl vinyl ether, benzyl vinyl ether, tetrahydrofurfuryl vinyl ether, vinyl phenyl ether, vinyl tolyl ether, vinyl chlorophenyl ether, vinyl-2,4-dichlorophenyl ether, vinyl naphthyl ether, and vinyl anthranyl ether; vinyl esters such as vinyl butyrate, vinyl isobutyrate, vinyltrimethyl acetate, vinyl diethyl acetate, vinyl valerate, vinyl caproate, vinyl chloroacetate, vinyl dichloroacetate, vinyl methoxyacetate, vinyl butoxyacetate, vinyl phenyl acetate, vinyl acetoacetate, vinyl lactate, vinyl-β-phenyl butyrate, vinyl benzoate, vinyl salicylate, vinyl chlorobenzoate, vinyl tetrachlorobenzoate, and vinyl naphthoate; styrenes such as styrene, methylstyrene, dimethylstyrene, trimethylstyrene, ethylstyrene, diethylstyrene, isopropylstyrene, butylstyrene, hexylstyrene, cyclohexylstyrene, decylstyrene, benzylstyrene, chloromethylstyrene, trifluoromethylstyrene, ethoxymethylstyrene, acetoxymethylstyrene, methoxystyrene, 4-methoxy-3-methylstyrene, dimethoxystyrene, chlorostyrene, dichlorostyrene, trichlorostyrene, tetrachlorostyrene, pentachlorostyrene, bromostyrene, dibromostyrene, iodostyrene, fluorostyrene, trifluorostyrene, 2-bromo-4-trifluoromethylstyrene, and 4-fluoro-3-trifluoromethylstyrene, or styrene derivatives; and olefins such as ethylene, propylene, 1-butene, 1-pentene, 1-hexene, 3-methyl-1-butene, 3-methyl-1-pentene, 3-ethyl-1-pentene, 4-methyl-1-pentene, 4-methyl-1-hexene, 4,4-dimethyl-1-hexene, 4,4-dimethyl-1-pentene, 4-ethyl-1-hexene, 3-ethyl-1-hexene, 1-octene, 1-decene, 1-dodecene, 1-tetradecene, 1-hexadecene, 1-octadecene, and 1-eicosene.

The alkali-soluble resin (D), which is a polymer of a monomer having an ethylenically unsaturated double bond, usually includes a unit derived from an unsaturated carboxylic acid. Examples of the unsaturated carboxylic acid include (meth)acrylic acid; (meth)acrylic acid amide; crotonic acid; and maleic acid, fumaric acid, citraconic acid, mesaconic acid, itaconic acid, and anhydrides of these dicarboxylic acids. There is no particular limitation on the amount of the unit derived from an unsaturated carboxylic acid included in the polymer of a monomer having an ethylenically unsaturated double bond to be used as the alkali-soluble resin, as long as the resin has desired alkali solubility. The amount of the unit deriaved from the unsaturated carboxylic acid in the resin used as the alkali-soluble resin is preferably 5 to 25% by mass, and more preferably 8 to 16% by mass, based on the mass of the resin.

Among the polymer of a monomer having an ethylenically unsaturated double bond, which is a polymer of one or more monomers selected from monomers exemplified above, a polymer of one or more monomers selected from (meth)acrylic acids and (meth)acrylic acid esters. A description will be made below on the polymer of one or more monomers selected from (meth)acrylic acids and (meth)acrylic acid esters.

There is no particular limitation on the (meth)acrylic acid ester to be used for preparation of the polymer of one or more monomers selected from (meth)acrylic acids and (meth)acrylic acid esters, as long as the object of the present invention is not inhibited, and the (meth)acrylic acid ester is appropriately selected from known (meth)acrylic acid esters.

Preferable examples of the (meth)acrylic acid ester include straight chain or branched chain alkyl (meth)acrylates such as methyl (meth)acrylate, ethyl (meth)acrylate, propyl (meth)acrylate, amyl (meth)acrylate, and t-octyl (meth)acrylate; chloroethyl (meth)acrylate, 2,2-dimethylhydroxypropyl (meth)acrylate, 2-hydroxyethyl (meth)acrylate, trimethylolpropane mono(meth)acrylate, benzyl (meth)acrylate, and furfuryl (meth)acrylate; (meth)acrylic acid ester which has a group having an epoxy group; and (meth)acrylic acid ester which has a group having an alicyclic skeleton. A detailed description will be later made on the (meth)acrylic acid ester which has a group having an epoxy group, and a (meth)acrylic acid ester which has a group having an alicyclic skeleton.

Among the polymer of one or more monomers selected from (meth)acrylic acids and (meth)acrylic acid esters, a resin including a unit derived from a (meth)acrylic acid ester which has a group having an epoxy group is preferable, since a transparent insulating film formed by using the photosensitive composition is excellent in adhesion to a base material, and mechanical strength.

The (meth)acrylic acid ester which has a group having an epoxy group may be any one of a (meth)acrylic acid ester which has a group having a chain aliphatic epoxy group, and a (meth)acrylic acid ester which has a group having an alicyclic epoxy group, as mentioned below.

The (meth)acrylic acid ester, which has a group having an epoxy group, may have an aromatic group. Examples of the aromatic ring constituting the aromatic group include a benzene ring and a naphthalene ring. Examples of the (meth)acrylic acid ester, which has an aromatic group and also has a group having an epoxy group, include 4-glycidyloxyphenyl (meth)acrylate, 3-glycidyloxyphenyl (meth)acrylate, 2-glycidyloxyphenyl (meth)acrylate, 4-glycidyloxyphenyl methyl(meth)acrylate, 3-glycidyloxyphenylmethyl (meth)acrylate, and 2-glycidyloxyphenylmethyl (meth)acrylate.

When the film formed by using the photosensitive composition is required to have transparency, the (meth)acrylic acid which has a group having an epoxy group preferably has no aromatic group.

Examples of the (meth)acrylic acid ester which has a group having a chain aliphatic epoxy group include a (meth)acrylic acid ester in which a chain aliphatic epoxy group is bonded to an oxy group (—O—) in an ester group (—O—CO—), such as epoxyalkyl (meth)acrylate or epoxyalkyloxyalkyl (meth)acrylate. The chain aliphatic epoxy group possessed by the (meth)acrylic acid ester may include one or plural oxy groups (—O—) in the chain. The number of carbon atoms of the chain aliphatic epoxy group is not particularly limited, and is preferably 3 to 20, more preferably 3 to 15, and particularly preferably 3 to 10.

Specific examples of the (meth)acrylic acid ester, which has a group having a chain aliphatic epoxy group include, epoxyalkyl (meth)acrylates such as glycidyl (meth)acrylate, 2-methylglycidyl (meth)acrylate, 3,4-epoxybutyl (meth)acrylate, and 6,7-epoxyheptyl (meth)acrylate; and epoxyalkyloxyalkyl (meth)acrylates such as 2-glycidyloxyethyl (meth)acrylate, 3-glycidyloxy-n-propyl (meth)acrylate, 4-glycidyloxy-n-butyl (meth)acrylate, 5-glycidyloxy-n-hexyl (meth)acrylate, and 6-glycidyloxy-n-hexyl (meth)acrylate.

The content of the unit derived from the (meth)acrylic acid ester which has a group having an epoxy group in the polymer of one or more monomers selected from (meth)acrylic acids and (meth)acrylic acid esters, including the unit derived from the (meth)acrylic acid ester which has a group having an epoxy group is preferably 1 to 95% by mass, and more preferably 40 to 80% by mass, based on the weight of the resin.

Among the polymer of one or more monomers selected from (meth)acrylic acids and (meth)acrylic acid esters, a resin including a unit derived from a (meth)acrylic acid ester which has a group having an alicyclic skeleton is also preferable, since it is easy to form a transparent insulating film having excellent transparency by using the photosensitive composition.

In the (meth)acrylic acid ester which has a group having an alicyclic skeleton, a group having an alicyclic skeleton may be any one of a group having an alicyclic hydrocarbon group, and a group having an alicyclic epoxy group. The alicyclic group constituting the alicyclic skeleton may be any one of a single ring and a polycyclic ring. Examples of the monocyclic alicyclic group include a cyclopentyl group, a cyclohexyl group, and the like. Examples of the polycyclic alicyclic group include a norbornyl group, an isobornyl group, a tricyclononyl group, a tricyclodecyl group, a tetracyclododecyl group, and the like.

Among the (meth)acrylic acid ester having an alicyclic skeleton, (meth)acrylic acid ester which has a group having an alicyclic hydrocarbon group includes compounds represented by the following formulas (d1-1) to (d1-8). Among these, compound represented by the following formulas (d1-3) to (d1-8) are preferable, and a compound represented by the following formula (d1-3) or (d1-4) is more preferable.

[Chem. 22]

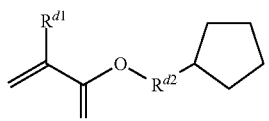 (d1-1)

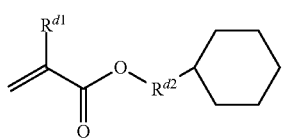 (d1-2)

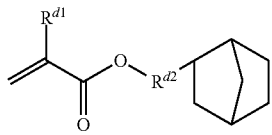 (d1-3)

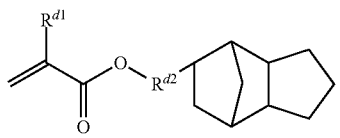 (d1-4)

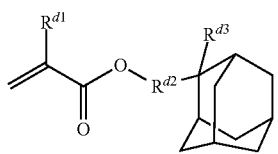 (d1-5)

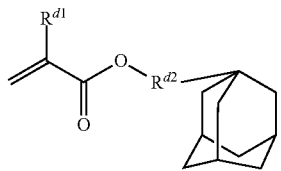 (d1-6)

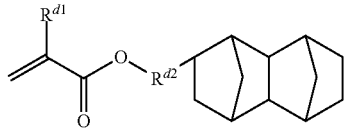 (d1-7)

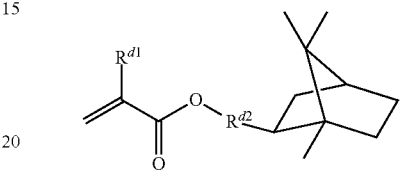 (d1-8)

In the above formula, $R^{d1}$ represents a hydrogen atom or a methyl group, $R^{d2}$ represents a single bond or a divalent aliphatic saturated hydrocarbon group having 1 to 6 carbon atoms, and $R^{d3}$ represents a hydrogen atom or an alkyl group having 1 to 5 carbon atoms. $R^{d2}$ is preferably a single bond, or a straight chain or branched chain alkylene group, for example, a methylene group, an ethylene group, a propylene group, a tetramethylene group, an ethylethylene group, a pentamethylene group, or a hexamethylene group. $R^{d3}$ is preferably a methyl group or an ethyl group.

Specific examples of (meth)acrylic acid ester which has a group having an alicyclic epoxy group, among the (meth)acrylic acid ester which has a group having an alicyclic skeleton, include compounds represented by the following formulas (d2-1) to (d2-16). Among these, compounds represented by the formulas (d2-1) to (d2-6) mentioned below are preferable and compounds represented by the formulas (d2-1) to (d2-4) mentioned below are more preferable, in order to impart a moderate level of developability to the photosensitive composition.

[Chem. 23]

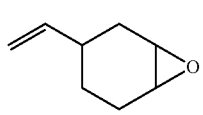 (d2-1)

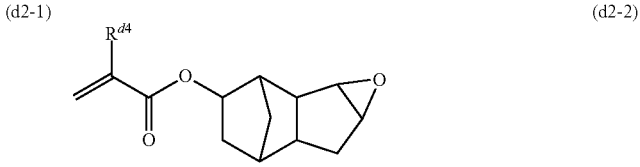 (d2-2)

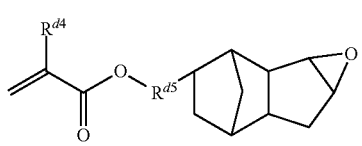 (d2-3)

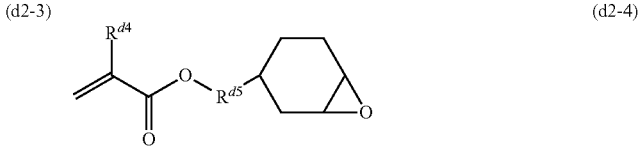 (d2-4)

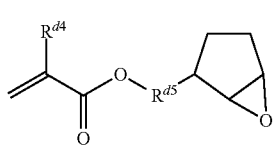 (d2-5)

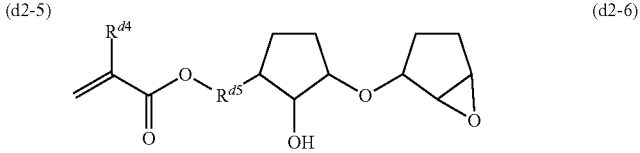 (d2-6)

-continued

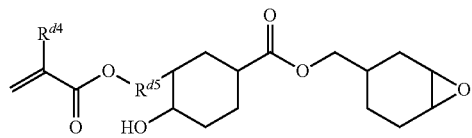
(d2-7)

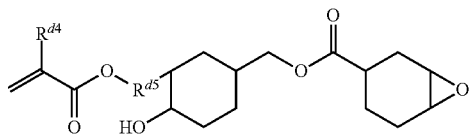
(d2-8)

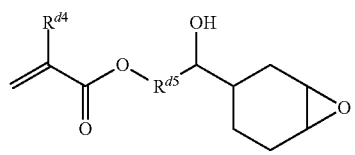
(d2-9)

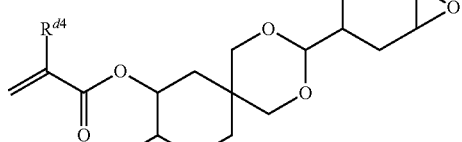
(d2-10)

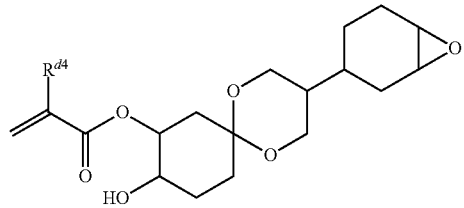
(d2-11)

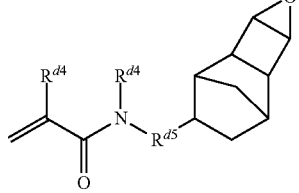
(d2-12)

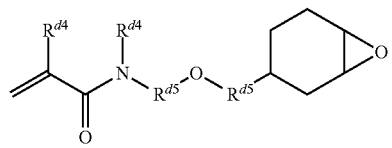
(d2-13)

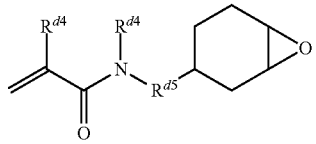
(d2-14)

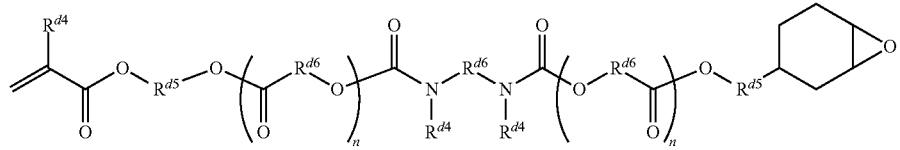
(d2-15)

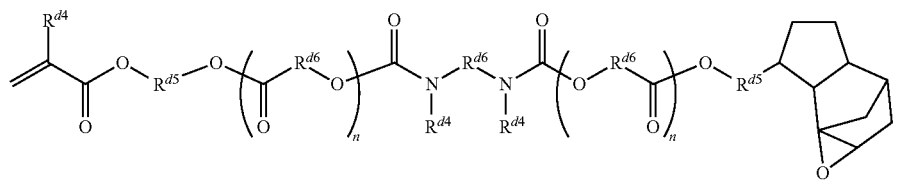
(d2-16)

In the above formula, $R^{d4}$ represents a hydrogen atom or a methyl group, $R^{d5}$ represents a divalent aliphatic saturated hydrocarbon group having 1 to 6 carbon atoms, $R^{d6}$ represents a divalent hydrocarbon group having 1 to 10 carbon atoms, and n represents an integer of 0 to 10. $R^{d5}$ is preferably a straight chain or branched chain alkylene group, for example, a methylene group, an ethylene group, a propylene group, a tetramethylene group, an ethylethylene group, a pentamethylene group, or a hexamethylene group. $R^{d6}$ is preferably, for example, a methylene group, an ethylene group, a propylene group, a tetramethylene group, an ethylethylene group, a pentamethylene group, a hexamethylene group, a phenylene group, a cyclohexylene group, or —$CH_2$-Ph-$CH_2$— (Ph represents a phenylene group).

When the polymer of one or more monomers selected from (meth)acrylic acids and (meth)acrylic acid esters is a resin including a unit derived from a (meth)acrylic acid ester which has a group having an alicyclic skeleton, the amount of the unit derived from the a (meth)acrylic acid ester which has a group having an alicyclic skeleton in the resin is preferably 5 to 95% by mass, more preferably 10 to 90% by mass, and further preferably 30 to 70% by mass.

Among the polymer of one or more monomers selected from (meth)acrylic acids and (meth)acrylic acid esters in the polymer including the unit derived from a (meth)acrylic acid ester which has a group having an alicyclic skeleton, a resin including a unit derived from (meth)acrylic acid, and a unit derived from a (meth)acrylic acid ester which has a group having an alicyclic epoxy group. The film formed by using the photosensitive composition containing (D) an alkali-soluble resin is excellent in adhesion to a base material. When using such a resin, it is possible to cause a self-reaction between a carboxyl group included in the resin, and an alicyclic epoxy group. Therefore, when using the photosensitive composition containing such a resin, it is possible to improve mechanical properties such as hardness of a film formed by causing the self-reaction between a carboxyl group and an alicyclic epoxy group by using a method of heating the film.

In the resin including a unit derived from (meth)acrylic acid, and a unit derived from a (meth)acrylic acid ester which has a group having an alicyclic epoxy group, the amount of the unit derived from (meth)acrylic acid in the resin is preferably 1 to 95% by mass, and more preferably 10 to 50% by mass. In the resin including a unit derived from (meth)acrylic acid, and a unit derived from a (meth)acrylic acid ester which has a group having an alicyclic epoxy group, the amount of the unit derived from a (meth)acrylic acid ester which has a group having an alicyclic epoxy group in the resin is preferably 1 to 95% by mass, and more preferably 30 to 70% by mass.

In the polymer of one or more monomers selected from (meth)acrylic acids and (meth)acrylic acid esters, including a unit derived from (meth)acrylic acid, and a unit derived from a (meth)acrylic acid ester which has a group having an alicyclic epoxy group, a resin including a unit derived from (meth)acrylic acid, a unit derived from a (meth)acrylic acid ester having an alicyclic hydrocarbon group, and a unit derived from a (meth)acrylic acid ester which has a group having an alicyclic epoxy group is preferable.

In the resin including a unit derived from (meth)acrylic acid, a unit derived from a (meth)acrylic acid ester having an alicyclic hydrocarbon group, and a unit derived from a (meth)acrylic acid ester which has a group having an alicyclic epoxy group, the amount of the unit derived from (meth)acrylic acid in the resin is preferably 1 to 95% by mass, and more preferably 10 to 50% by mass. In the resin including a unit derived from (meth)acrylic acid, a unit derived from a (meth)acrylic acid ester having an alicyclic hydrocarbon group, and a unit derived from a (meth)acrylic acid ester which has a group having an alicyclic epoxy group, the amount of the unit derived from a (meth)acrylic acid ester having an alicyclic hydrocarbon group is preferably 1 to 95% by mass, and more preferably 10 to 70% by mass. In the resin including a unit derived from (meth)acrylic acid, a unit derived from a (meth)acrylic acid ester having an alicyclic hydrocarbon group, and a unit derived from a (meth)acrylic acid ester which has a group having an alicyclic epoxy group, the amount of the unit derived from a (meth)acrylic acid ester which has a group having an alicyclic epoxy group is preferably 1 to 95% by mass, and more preferably 30 to 80% by mass.

A mass average molecular weight (Mw: value in terms of polystyrene measured by gel permeation chromatography (GPC), the same shall apply in the present description) of the alkali-soluble resin (D) is preferably 2,000 to 20,000, and more preferably 2,000 to 18,000. With the above-specified range, film formability of the photosensitive composition and developability after the exposure tends to be well-balanced.

When the photosensitive composition includes the alkali-soluble resin (D), the content of the alkali-soluble resin (D) in the photosensitive composition is preferably 15 to 95% by mass, more preferably 35 to 85% by mass, and particularly preferably 50 to 70% by mass, in the solid content of the photosensitive composition.

<Other Components>

The photosensitive composition according to the present invention may contain various additives where necessary. Specific examples thereof include a solvent, a sensitizer, a curing accelerator, a filler, an adhesion accelerator, an antioxidant, an ultraviolet absorber, a flocculation inhibitor, thermopolymerization inhibitor, a defoaming agent, a surfactant, and the like.

Examples of the solvent used in the photosensitive composition according to the present invention include (poly) alkylene glycol monoalkyl ethers such as ethylene glycol monomethyl ether, ethylene glycol monoethyl ether, ethylene glycol-n-propyl ether, ethylene glycol mono-n-butyl ether, diethylene glycol monomethyl ether, diethylene glycol monoethyl ether, diethylene glycol mono-n-propyl ether, diethylene glycol mono-n-butyl ether, triethylene glycol monomethyl ether, triethylene glycol monoethyl ether, propylene glycol monomethyl ether, propylene glycol monoethyl ether, propylene glycol mono-n-propyl ether, propylene glycol mono-n-butyl ether, dipropylene glycol monomethyl ether, dipropylene glycol monoethyl ether, dipropylene glycol mono-n-propyl ether, dipropylene glycol mono-n-butyl ether, tripropylene glycol monomethyl ether, and tripropylene glycol monoethyl ether; (poly)alkylene glycol monoalkyl ether acetates such as ethylene glycol monomethyl ether acetate, ethylene glycol monoethyl ether acetate, diethylene glycol monomethyl ether acetate, diethylene glycol monoethyl ether acetate, propylene glycol monomethyl ether acetate, and propylene glycol monoethyl ether acetate; other ethers such as diethylene glycol dimethyl ether, diethylene glycol methyl ethyl ether, diethylene glycol diethyl ether, and tetrahydrofuran; ketones such as methyl ethyl ketone, cyclohexanone, 2-heptanone, and 3-heptanone; lactic acid alkyl esters such as methyl 2-hydroxypropionate and ethyl 2-hydroxypropionate; other esters such as ethyl 2-hydroxy-2-methylpropionate, methyl 3-methoxypropionate, ethyl 3-methoxypropionate, methyl 3-ethoxypropionate, ethyl 3-ethoxypropionate, ethoxyethyl acetate, hydroxyethyl acetate, methyl 2-hydroxy-3-methylbutanoic acid methyl, 3-methyl-3-methoxybutyl acetate, 3-methyl-3-methoxybutyl propionate, ethyl acetate, n-propyl acetate, isopropyl acetate, n-butyl acetate, isobutyl acetate, n-pentyl formate, isopentyl acetate, n-butyl propionate, ethyl butyrate, n-propyl butyrate, isopropyl butyrate, n-butyl butyrate, methyl pyruvate, ethyl pyruvate, n-propyl pyruvate, methyl acetoacetate, ethyl acetoacetate, and ethyl 2-oxobutanoate; aromatic hydrocarbons such as toluene and xylene; and amides such as N-methylpyrrolidone, N,N-dimethylformamide, and N,N-dimethylacetamide. These solvents may be used alone, or two or more solvents may be used in combination.

Among these solvents, propylene glycol monomethyl ether, ethylene glycol monomethyl ether acetate, propylene glycol monomethyl ether acetate, propylene glycol monoethyl ether acetate, diethylene glycol dimethyl ether, diethylene glycol methyl ethyl ether, cyclohexanone, and 3-methoxybutyl acetate are preferable since they exhibit excellent solubility in the component (A) and component (B) mentioned above and can improve dispersibility of the component (C) mentioned above. It is particularly preferable to use propylene glycol monomethyl ether acetate and 3-methoxybutyl acetate. The solvent may be appropriately determined according to applications of the photosensitive composition. As an example, the amount of the solvent is about 50 to 900 parts by mass based on 100 parts by mass of the total solid content of the photosensitive composition.

Examples of the thermopolymerization inhibitor used in the photosensitive composition according to the present invention include hydroquinone, hydroquinone monoethyl ether, and the like. Examples of the defoaming agent include a silicone-based and a fluorine-based compound, and examples of the surfactant include anionic, cationic, and nonionic compounds, respectively.

[Method for Preparing Photosensitive Composition]

The photosensitive composition according to the present invention is prepared by mixing all components mentioned above using a stirrer. When the photosensitive composition thus prepared does not contain an insoluble component such as pigment, the photosensitive composition may be filtered with a filter so as to make the composition uniform.

<<Film Formation Method>>

A description will be made on a method in which a film to be used as an insulating film and a color filter is formed by using the photosensitive composition described above. The film formed by using the photosensitive composition may be patterned where necessary.

To form a film by using the photosensitive composition of the present invention, first, photosensitive composition is applied on a substrate using a contact transfer type applicator such as a roll coater, a reverse coater, or a bar coater, or a non-contact type applicator such as a spinner (rotary applicator) or a curtain flow coater.

Then, the photosensitive composition applied is dried to form a coating film. There is no particular limitation on a drying method, and examples thereof include (1) a method in which the coated substrate is dried at a temperature of 80 to 120° C., and preferably 90 to 100° C., for 60 to 120 seconds drying using a hot plate, (2) a method in which the coated substrate is left to stand at room temperature for several hours to several days, and (3) a method in which the solvent is removed by placing the coated substrate in a warm air heater or an infrared heater for several tens of minutes to several hours.

Then, this coating film is exposed by irradiation with active energy rays such as ultraviolet rays and excimer laser light. Light exposure for example may be position-selectively performed by a method in which exposure is performed via a negative mask. The dose of energy rays varies depending of the composition of the photosensitive composition, and is preferably about 40 to 200 mJ/cm$^2$. As described previously, the photosensitive composition according to the present invention is excellent in sensitivity, so that use of the photosensitive composition of the present invention enables an improvement of productivity of a display device such as a liquid crystal display panel.

When the coating film is position-selectively exposed, the exposed film is patterned to form a desired shape by developing with a developing solution. There is no particular limitation on the development method and, for example, it is possible to use a dipping method, a spraying method, and the like. The developing solution is appropriately selected according to the composition of the photosensitive composition. When the photosensitive composition contains an alkali-soluble component such as an alkali-soluble resin, it is possible to use, as the developing solution, an organic developing solution such as monoethanolamine, diethanolamine, or triethanolamine, or an aqueous solution of sodium hydroxide, potassium hydroxide, sodium carbonate, ammonia, or a quaternary ammonium salt.

Then, the pattern after the development is preferably post-baked at about 200 to 250° C.

The pattern thus formed can be suitably used in applications, for example, an insulating film, pixels and a black matrix that constitute a color filter, and the like, which are used in a display device such as a liquid crystal display. Such an insulating film, a color filter, or a display device using the color filter is one of the present invention.

EXAMPLES

The present invention will be more specifically descried below by way of Examples, but the scope of the present invention is not limited to these Examples.

In Synthesis Examples mentioned below, compounds 1 to 15, a compound 20, and compounds 26 to 29 mentioned below, which are compounds represented by the formula (1), were synthesized.

[Chem. 24]

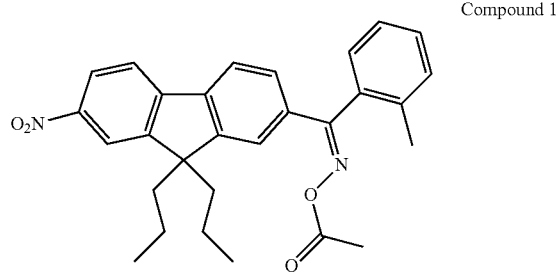

Compound 1

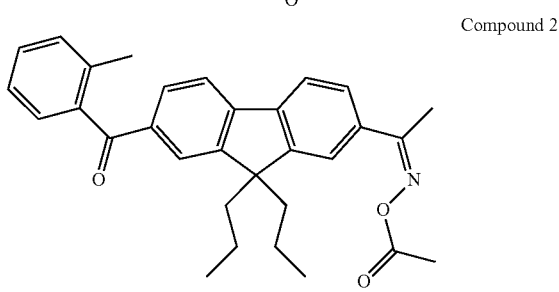

Compound 2

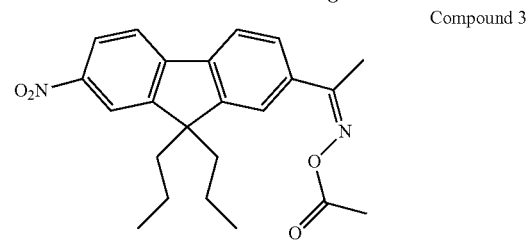

Compound 3

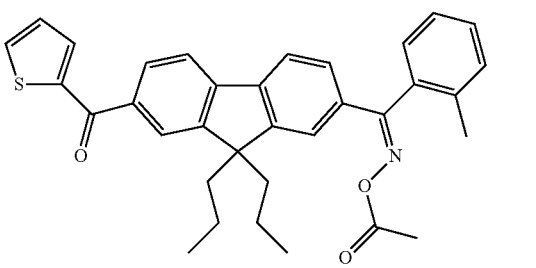

Compound 4

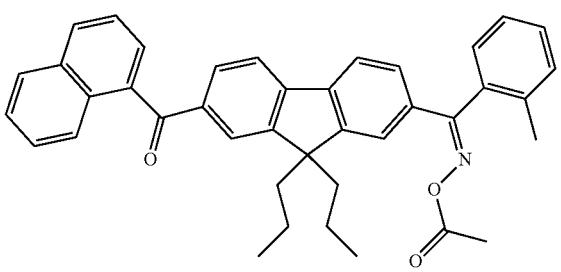

Compound 5

-continued
Compound 6
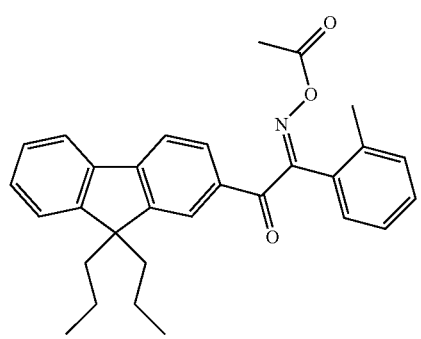
Compound 10
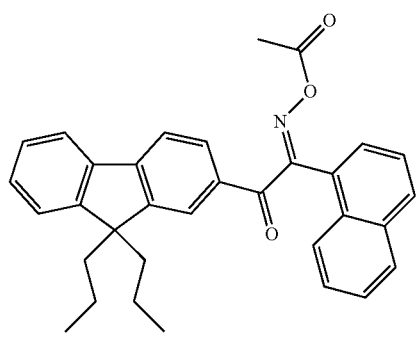
Compound 7
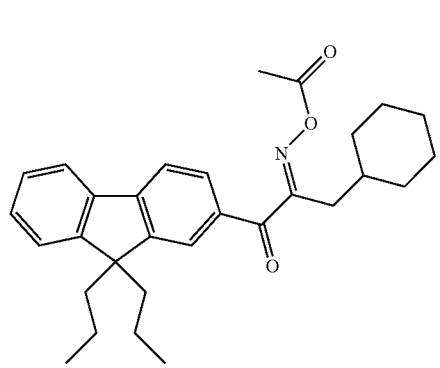
Compound 11
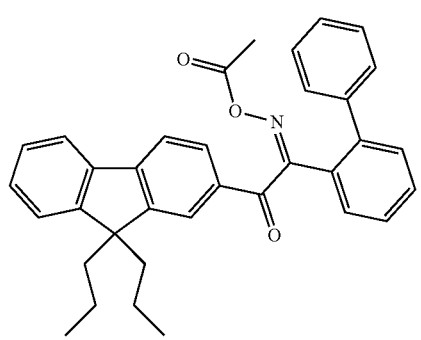
Compound 8
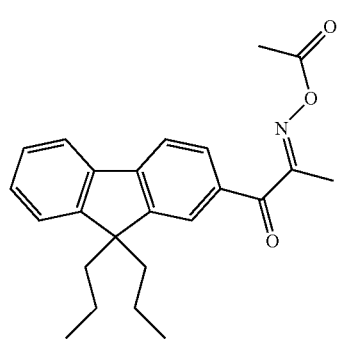
Compound 12
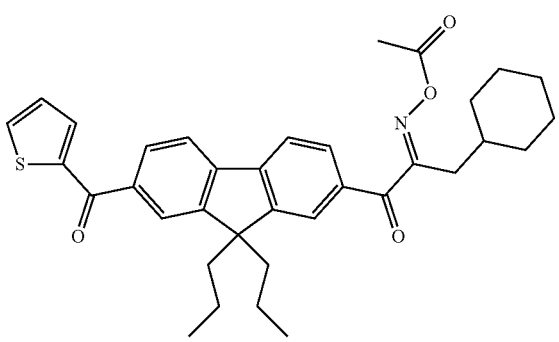
Compound 9
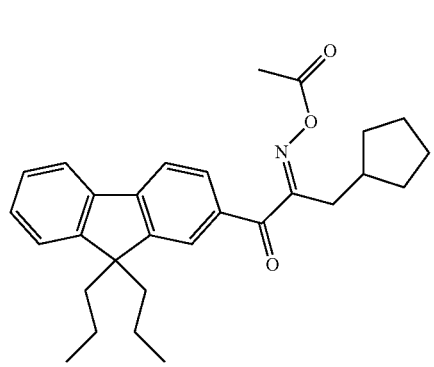
Compound 13
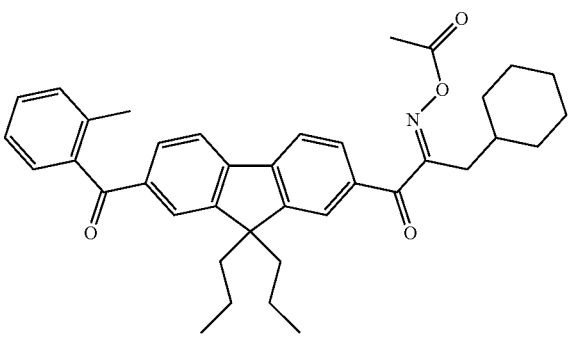

Compound 14

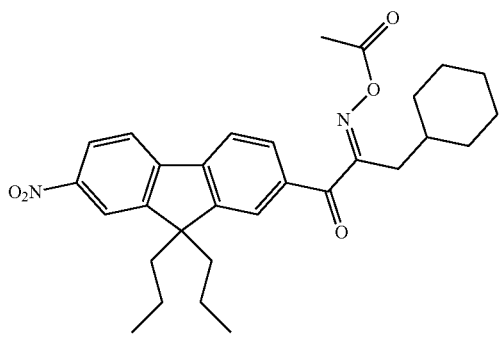

Compound 15

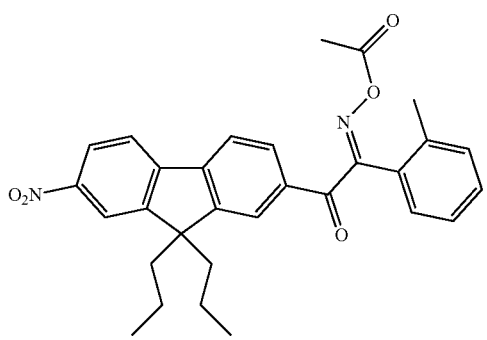

Compound 20

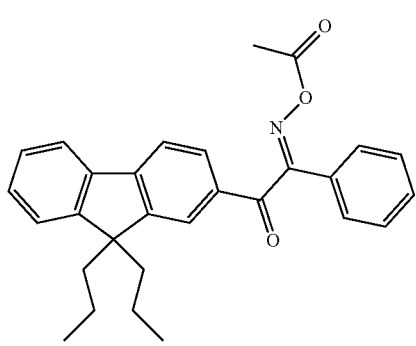

Compound 26

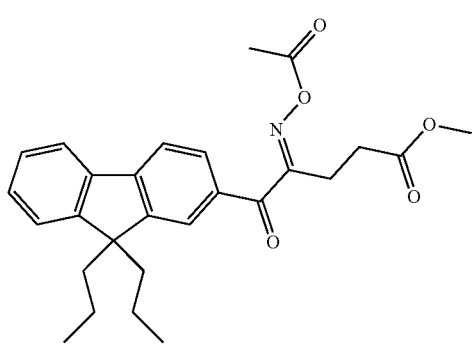

Compound 27

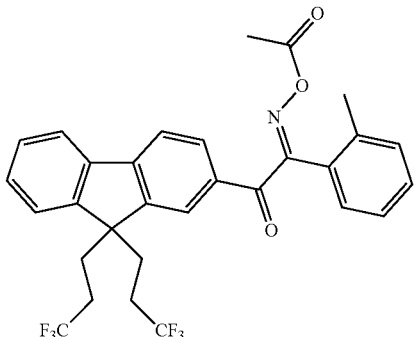

Compound 28

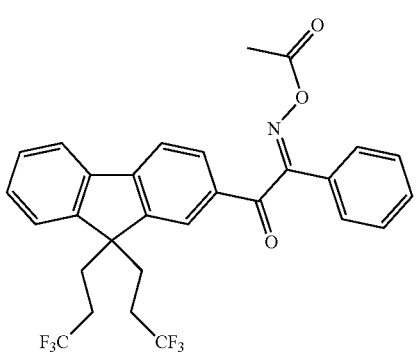

Compound 29

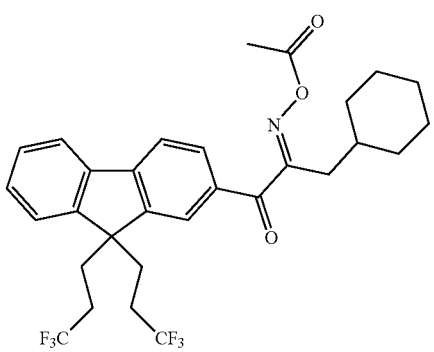

Synthesis Example 1

Synthesis of 9,9-di-n-propylfluorene

Fluorene 6.64 g, (40 mmol) was dissolved in 27 mL of THF. To the solution thus obtained, 0.12 g (1.1 mmol) of potassium tert-butoxide, 12.30 g (100 mmol) of 1-bromopropane, and 27 mL of an aqueous sodium hydroxide solution having a concentration of 50% by mass were added under a nitrogen atmosphere. The mixture thus obtained was reacted by stirring at 80° C. for 3 hours. To the mixture obtained after the reaction, 33 g of ethyl acetate and 33 g of water were added, followed by separation into the organic layer and the aqueous layer. After the organic layer thus obtained was dehydrated over anhydrous sodium sulfate, the solvent was removed from the organic layer using a rotary evaporator to obtain 8.32 g (yield: 83%) of 9,9-di-n-propylfluorene.

Synthesis Example 2

Synthesis of 2-nitro-9,9-di-n-propylfluorene

To a mixed solvent of 131 mL of acetic acid and 262 mL of acetic anhydride, 9.18 g (40 mmol) of copper(II) dinitrate trihydrate was added, and then the mixed solvent was stirred for 10 minutes. Thereafter, a solution prepared by dissolving 10.02 g (40 mmol) of 9,9-di-n-propylfluorene obtained in Synthesis Example 1 in 131 mL of acetic acid was slowly added in the mixed solvent in several portions. Next, the mixed solvent containing 9,9-di-n-propylfluorene was subjected to a nitration reaction by stirring for 3 hours. After the reaction, the reaction mixture was poured into a beaker containing ice water. The precipitate thus formed was filtered and recovered, and then the precipitate was washed with water and dried to obtain 10.76 g (yield: 91%) of 2-nitro-9,9-di-n-propylfluorene.

Synthesis Example 3

Synthesis of Compound 1

2-Nitro-9,9-dipropylfluorene (11.82 g, 40 mmol) obtained by the method of Synthesis Example 2 and 5.8 g (44 mmol) of aluminum chloride were dissolved in 40 mL of dichloromethane. While cooling a dichloromethane solution in an ice bath, 6.80 g (44 mmol) of o-toluoyl chloride was added dropwise in the dichloromethane solution at a temperature of 5° C. or lower. After the dropwise addition, the temperature of the reaction solution was raised to room temperature over one hour while stirring the reaction solution, and then the reaction was continued at room temperature for 3 hours.

The reaction solution thus obtained was added dropwise in a beaker containing 300 mL of ice water. After the mixture in the beaker was transferred to a separatory funnel, 200 mL of ethyl acetate was added to the separatory funnel and the product was extracted into the organic layer. After the organic layer was separated, the product in the aqueous layer was extracted with 100 mL of ethyl acetate. The organic layer obtained by extracting twice was washed with 300 mL of an aqueous 10% sodium carbonate solution and then washed with 300 mL of water. After washing, the organic layer was dried over anhydrous magnesium sulfate and the solvent was distilled off from the organic layer using a rotary evaporator to obtain an oily substance. The oily substance was purified by silica gel column chromatography (developing solvent, ethyl acetate:n-hexane=1:1 (mass ratio)) to obtain 16.11 g (yield: 94%) of a pale yellow solid (2-(2-methylbenzoyl)-7-nitro-9,9-di-n-propylfluorene).

After dissolving 8.56 g (20 mmol) of the thus obtained pale yellow solid and 1.5 g (21 mmol) of hydroxylamine hydrochloride in 100 mL of ethanol, an ethanol solution was refluxed for 2 hours. After reflux, ethanol was distilled off from the reaction solution and then the residue was washed with water. The residue thus washed was dissolved in ethyl acetate and then the ethyl acetate solution was dried over magnesium sulfate. After drying, ethyl acetate was removed from the ethyl acetate solution using a rotary evaporator to obtain the oxime (2-methylphenyl(7-nitro-9,9-di-n-propylfluoren-2-yl)ketone oxime) as the residue. The oxime thus obtained was dissolved in 60 mL of THF and acetyl chloride (3.45 g, 44 mmol) was added in THF, followed by a reaction under stirring. After the reaction, triethylamine (4.7 g, 46 mmol) was added dropwise to the reaction solution at room temperature. Together with the dropwise addition, sedimentation of a salt was recognized. After stirring the reaction solution to which triethylamine was added for 2 hours, 40 ml of water was added to the reaction solution. Then, the product in the reaction solution was extracted with 40 mL of ethyl acetate. The organic layer was washes twice with 40 mL of water and then washed twice with 40 mL of an aqueous saturated potassium carbonate solution. After washing, the organic layer was dried over magnesium sulfate and the solvent was removed from the organic layer using a rotary evaporator to obtain the residue. The residue was purified by silica gel column chromatography (developing solvent, ethyl acetate:n-hexane=1:1 (mass ratio)) to obtain 7.43 g (15.80 mmol, yield: 79%) of a compound 1. The measurement results of $^1$H-NMR of the compound 1 are as follows.

$^1$H-NMR (600 MHz, CDCl$_3$, ppm): 8.26 (d, 1H), 8.21 (d, 1H), 7.78-7.81 (m, 2H), 7.72 (d, 1H), 7.46 (d, 1H), 7.39 (t, 1H), 7.29-7.35 (m, 2H), 7.12 (d, 1H), 2.18 (s, 3H), 2.07 (s, 3H), 2.01 (m, 4H), 0.68 (m, 10H).

Synthesis Example 4

Synthesis of Compound 2

9,9-di-n-propylfluorene 10.02 g, (40 mmol) and 5.87 g (44 mmol) of aluminum chloride were dissolved in 40 mL of dichloromethane. While cooling the dichloromethane solution in an ice bath, 6.80 g (44 mmol) of o-toluoyl chloride was added dropwise in the dichloromethane solution at a temperature of 5° C. or lower. After the dropwise addition, the temperature of the reaction solution was raised to room temperature over one hour while stirring the reaction solution, and then the reaction was continued at room temperature for 3 hours.

Thereafter, the reaction solution was cooled to 5° C. in an ice bath. To the reaction solution, 5.87 g (44 mmol) of aluminum chloride was added and then 3.45 g (44 mmol) of acetyl chloride was added dropwise to the reaction solution while maintaining the temperature of the reaction solution at 5° C. or lower. After the dropwise addition, the temperature of the reaction solution was raised to room temperature over one hour while stirring the reaction solution, and then the reaction was continued at room temperature for 3 hours.

The reaction solution thus obtained was added dropwise in a beaker containing 300 mL of ice water. After the mixture in the beaker was transferred to a separatory funnel, 200 mL of ethyl acetate was added to the separatory funnel and the product was extracted into the organic layer. After the organic layer was separated, the product in the aqueous layer was extracted with 100 mL of ethyl acetate. The organic layer obtained by extracting twice was washed with 300 mL of an aqueous 10% sodium carbonate solution and then washed with 300 mL of water. After washing, the organic layer was dried over anhydrous magnesium sulfate and the solvent was distilled off from the organic layer using a rotary evaporator to obtain an oily substance. The oily substance was purified by silica gel column chromatography (developing solvent, ethyl acetate:n-hexane=1:1 (mass ratio)) to obtain 16.17 g (yield: 95%) of a pale yellow solid (2-acetyl-7-(2-methylbenzoyl)-9,9-di-n-propylfluorene).

In the same manner as in the synthesis method of the compound 1 from 2-(2-methylbenzoyl)-7-nitro-9,9-di-n-propylfluorene mentioned in Synthesis Example 3, except that 20 mmol of 2-(2-methylbenzoyl)-7-nitro-9,9-di-n-propylfluorene was changed to 20 mmol of 2-acetyl-7-(2-methylbenzoyl)-9,9-di-n-propylfluorene, 8.23 g (17.60 mmol, yield: 88%) of a compound 2 was obtained. The measurement results of $^1$H-NMR of the compound 2 are as follows.

$^1$H-NMR (600 MHz, CDCl$_3$, ppm): 7.91 (d, 1H), 7.77-7.68 (m, 5H), 7.41 (t, 1H), 7.35 (d, 1H), 7.32 (d, 1H), 7.27 (t, 1H), 2.42 (s, 3H), 2.37 (s, 3H), 2.28 (s, 3H), 2.01 (m, 4H), 0.65 (m, 10H).

Synthesis Example 5

Synthesis of Compound 3

In the same manner as in Synthesis Example 3, except that 3.45 g (44 mmol) of acetyl chloride was used in place of 6.80 g (44 mmol) of o-toluoyl chloride, 6.63 g (16.81 mmol, yield: 84%) of a compound 3 was obtained. The measurement results of $^1$H-NMR of the compound 3 are as follows.

$^1$H-NMR (600 MHz, CDCl$_3$, ppm): 8.2 (d, 1H), 8.23 (s, 1H), 7.79-7.83 (m, 4H), 2.48 (s, 3H), 2.27 (s, 3H), 2.06-2.12 (m, 4H), 0.51-0.68 (m, 10H).

Synthesis Example 6

Synthesis of Compound 4

In the same manner as in Synthesis Example 3, except that 6.80 g (44 mmol) of o-toluoyl chloride was changed to 6.45 g (44 mmol) of thiophene-2-carboxylic acid chloride and 3.45 g (44 mmol) of acetyl chloride was changed to 6.80 g (44 mmol) of o-toluoyl chloride in the step of acylating 9,9-di-n-propylfluorene in two stages with respect to the method mentioned in Synthesis Example 3, 7.71 g (14.39 mmol, yield: 72%) of a compound 4 was obtained from 9,9-di-n-propylfluorene. The measurement results of $^1$H-NMR of the compound 4 are as follows.

$^1$H-NMR (600 MHz, CDCl$_3$, ppm): 8.13 (d, 1H), 8.02 (s, 1H), 7.71-7.81 (m, 4H), 7.46 (d, 1H), 7.23-7.28 (m, 4H), 7.08 (t, 1H), 7.05 (d, 1H), 2.28 (s, 3H), 2.21 (s, 3H), 2.01 (m, 4H), 0.68 (m, 10H).

Synthesis Example 7

Synthesis of Compound 5

In the same manner as in Synthesis Example 3, except that 6.80 g (44 mmol) of o-toluoyl chloride was changed to 8.39 g (44 mmol) of 1-naphthoic acid chloride and 3.45 g (44 mmol) of acetyl chloride was changed to 6.80 g (44 mmol) of o-toluoyl chloride in the step of acylating 9,9-di-n-propylfluorene in two stages with respect to the method mentioned in Synthesis Example 3, 8.00 g (13.80 mmol, yield: 69%) of a compound 5 was obtained from 9,9-di-n-propylfluorene. The measurement results of $^1$H-NMR of the compound 5 are as follows.

$^1$H-NMR (600 MHz, CDCl$_3$, ppm): 8.20 (d, 1H), 8.15 (s, 1H), 7.91 (d, 1H), 7.72-7.85 (m, 6H), 7.50-7.57 (m, 3H), 7.23-7.27 (m, 4H), 7.05 (d, 1H), 2.27 (s, 3H), 2.22 (s, 3H), 2.00 (m, 4H), 0.69 (m, 10H).

Synthesis Example 8

Synthesis of Compound 6

9,9-Di-n-propylfluorene 4.10 g, (16.37 mmol) was reacted with 3.04 g (18.00 mmol) of (2-methylphenyl)acetic acid chloride in 50 ml of a dichloromethane solvent in the presence of 2.62 g of aluminum chloride under ice cooling for one hour. The organic layer was subjected to liquid separation by pouring the reaction mixture into ice water. The organic layer thus recovered was dried over anhydrous magnesium sulfate and then evaporated. The residue was purified by a silica gel column using an eluent of ethyl acetate/hexane=1/2 to obtain 5.95 g (15.55 mmol) of 2-(2-methylphenyl)acetyl-9,9-di-n-propylfluorene.

2-(2-Methylphenyl)acetyl-9,9-di-n-propylfluorene 5.95 g, (15.55 mmol) was reacted with 1.60 g (15.55 mmol) of concentrated hydrochloric acid in 25 ml of a dimethylformamide solvent in the presence of 2.42 g (23.33 mmol) of isobutyl nitrite under ice cooling for 3 hours. The reaction solution was evaporated and ethyl acetate was added to the residue, and the mixture was washed with a saturated saline solution, dried over anhydrous magnesium sulfate, and then evaporated to obtain 4.80 g (11.67 mmol) of 2-[2-methylphenyl(hydroxyimino)acetyl]-9,9-di-n-propylfluorene having the following structure.

[Chem. 25]

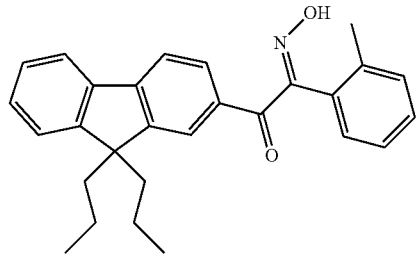

The measurement results of $^1$H-NMR of 2-[2-methylphenyl(hydroxyimino)acetyl]-9,9-di-n-propylfluorene are as follows.

$^1$H-NMR (600 MHz, CDCl$_3$, ppm): 8.60 (bs, 1H), 8.15 (d, 1H), 8.14 (s, 1H), 7.76-8.00 (m, 2H), 7.26-7.53 (m, 7H), 2.35 (s, 3H), 1.98-2.01 (m, 4H), 0.63-0.67 (m, 10H)

2-[2-Methylphenyl(hydroxyimino)acetyl]-9,9-di-n-propylfluorene (4.80 g, 11.67 mmol), 1.43 g (13.42 mmol) of acetic anhydride, 1.36 g (13.42 mmol) of triethylamine, and 45.00 ml of a dimethylformamide solvent were mixed, followed by stirring at 35° C. for 3 hours. After cooling to room temperature, ethyl acetate was added to the reaction solution, and the mixture was washed with water, dried over anhydrous magnesium sulfate, and then evaporated. The residue was purified by a silica gel column using an eluent of ethyl acetate/hexane=2/1 to obtain 4.76 g (10.50 mmol, yield: 72%) of a compound 6. The measurement results of $^1$H-NMR of the compound 6 are as follows.

$^1$H-NMR (600 MHz, CDCl$_3$, ppm): 8.25 (d, 1H), 8.22 (s, 1H), 7.83 (d, 1H), 7.81 (dd, 1H), 7.33-7.40 (m, 3H), 7.26-7.33 (m, 4H), 2.35 (s, 3H), 2.14 (s, 3H), 1.95-2.07 (m, 4H), 0.63-0.66 (m, 10H).

Synthesis Example 9

Synthesis of Compound 7

In the same manner as in Synthesis Example 8, except that 3.04 g (18.00 mmol) of (2-methylphenyl)acetic acid chloride was changed to 3.14 g (18.00 mmol) of 3-cyclohexylpropionic acidchloride, 2-[cyclohexylmethyl(hydroxyimino) acetyl]-9,9-di-n-propylfluorene having the following structure which is an intermediate, and 4.96 g (10.80 mmol, yield: 75%) of a compound 7 were obtained.

[Chem. 26]

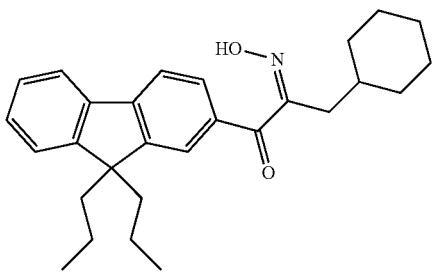

The measurement results of ¹H-NMR of 2-[cyclohexylmethyl (hydroxyimino)acetyl]-9,9-di-n-propylfluorene are as follows.

¹H-NMR (600 MHz, CDCl₃, ppm): 8.80 (bs, 1H), 7.90-7.98 (m, 2H), 7.70-7.80 (m, 2H), 7.30-7.40 (m, 3H), 2.72 (d, 2H), 1.88-2.02 (m, 4H), 1.54-1.80 (m, 6H), 0.95-1.28 (m, 5H), 0.67-0.77 (m, 10H)

The measurement results of ¹H-NMR of the compound 7 are as follows.

¹H-NMR (600 MHz, CDCl₃, ppm): 8.08-8.14 (m, 2H), 7.70-7.79 (m, 2H), 7.32-7.40 (m, 3H), 2.78 (d, 2H), 2.28 (s, 3H), 1.88-2.10 (m, 4H), 1.53-1.78 (m, 6H), 1.00-1.30 (m, 5H), 0.60-0.77 (m, 10H).

Synthesis Example 10

Synthesis of Compound 8

In the same manner as in Synthesis Example 8, except that 3.04 g (18.00 mmol) of (2-methylphenyl)acetic acid chloride was changed to 1.67 g (18.00 mmol) of propionic acid chloride, 3.94 g (10.45 mmol, yield: 69%) of a compound 8 was obtained. The measurement results of ¹H-NMR of the compound 8 are as follows.

¹H-NMR (600 MHz, CDCl₃, ppm): 8.14 (m, 2H), 7.75 (m, 2H), 7.32 (m, 3H), 2.26 (s, 3H), 2.23 (s, 3H), 1.99-2.13 (m, 4H), 0.28-0.35 (m, 10H).

Synthesis Example 11

Synthesis of Compound 9

In the same manner as in Synthesis Example 8, except that 3.04 g (18.00 mmol) of (2-methylphenyl)acetic acid chloride was changed to 2.89 g (18.00 mmol) of 3-cyclopentylpropionic acid chloride, 4.46 g (10.02 mmol, yield: 72%) of a compound 9 was obtained. The measurement results of ¹H-NMR of the compound 9 are as follows.

¹H-NMR (600 MHz, CDCl₃, ppm): 8.06-8.12 (m, 2H), 7.71-7.78 (m, 2H), 7.31-7.40 (m, 3H), 2.52 (d, 2H), 2.27 (s, 3H), 1.89-2.19 (m, 5H), 1.48-1.80 (m, 6H), 1.19-1.26 (m, 2H), 0.61-0.77 (m, 10H).

Synthesis Example 12

Synthesis of Compound 10

In the same manner as in Synthesis Example 8, except that 3.04 g (18.00 mmol) of (2-methylphenyl)acetic acid chloride was changed to 3.68 g (18.00 mmol) of (α-naphthyl)acetic acid chloride, 5.29 g (10.80 mmol, yield: 78%) of a compound 10 was obtained. The measurement results of ¹H-NMR of the compound 10 are as follows.

¹H-NMR (600 MHz, CDCl₃, ppm): 8.26 (d, 1H), 8.24 (s, 1H), 7.82 (d, 1H), 7.82 (dd, 1H), 7.30-7.70 (m, 10H), 2.14 (s, 3H), 1.94-2.05 (m, 4H), 0.62-0.66 (m, 10H).

Synthesis Example 13

Synthesis of Compound 11

In the same manner as in Synthesis Example 8, except that 3.04 g (18.00 mmol) of (2-methylphenyl)acetic acid chloride was changed to 4.15 g (18.00 mmol) of 1,1'-biphenyl-2-acetic acid chloride, 5.36 g (10.40 mmol, yield: 73%) of a compound 11 was obtained. The measurement results of ¹H-NMR of the compound 11 are as follows.

¹H-NMR (600 MHz, CDCl₃, ppm): 8.22 (d, 1H), 8.19 (s, 1H), 7.84 (d, 1H), 7.83 (dd, 1H), 7.20-7.45 (m, 12H), 2.15 (s, 3H), 1.94-2.07 (m, 4H), 0.63-0.66 (m, 10H).

Synthesis Example 14

Synthesis of Compound 12

In the same manner as in Synthesis Example 9, except that 4.10 g (16.37 mmol) of 9,9-di-n-propylfluorene was changed to 5.90 g (16.37 mmol) of 2-(thiophen-2-yl)-9,9-di-n-propylfluorene, 5.78 g (10.15 mmol, yield: 69%) of a compound 12 was obtained.

2-(Thiophen-2-yl)-9,9-di-n-propylfluorene was obtained in the same manner as in Synthesis Example 6. The measurement results of ¹H-NMR of the compound 12 are as follows.

¹H-NMR (600 MHz, CDCl₃, ppm): 8.20 (d, 1H), 8.18 (s, 1H), 7.70-7.88 (m, 4H), 7.33-7.45 (m, 2H), 7.12 (t, 1H), 2.78 (d, 2H), 2.28 (s, 3H), 1.88-2.11 (m, 4H), 1.54-1.77 (m, 6H), 0.99-1.30 (m, 5H), 0.59-0.78 (m, 10H).

Synthesis Example 15

Synthesis of Compound 13

In the same manner as in Synthesis Example 9, except that 4.10 g (16.37 mmol) of 9,9-di-n-propylfluorene was changed to 6.03 g (16.37 mmol) of 2-(2-methylbenzoyl)-9,9-di-n-propylfluorene, 5.84 g (10.10 mmol, yield: 71%) of a compound 13 was obtained.

2-(2-Methylbenzoyl)-9,9-di-n-propylfluorene was obtained in the same manner as in Synthesis Example 4. The measurement results of ¹H-NMR of the compound 13 are as follows.

¹H-NMR (600 MHz, CDCl₃, ppm): 8.18 (d, 1H), 8.15 (s, 1H), 7.65-7.80 (m, 4H), 7.30-7.45 (m, 4H), 2.77 (d, 2H), 2.28 (s, 3H), 1.87-2.09 (m, 4H), 1.55-1.78 (m, 6H), 1.00-1.31 (m, 5H), 0.60-0.77 (m, 10H).

Synthesis Example 16

Synthesis of Compound 14

In the same manner as in Synthesis Example 9, except that 4.10 g (16.37 mmol) of 9,9-di-n-propylfluorene was changed to 4.84 g (16.37 mmol) of 2-nitro-9,9-di-n-propylfluorene, 5.50 g (10.90 mmol, yield: 79%) of a compound 14 was obtained.

2-Nitro-9,9-di-n-propylfluorene was obtained in the same manner as in Synthesis Example 2. The measurement results of ¹H-NMR of the compound 14 are as follows.

$^1$H-NMR (600 MHz, CDCl$_3$, ppm): 8.31 (d, 1H), 8.26 (s, 1H), 7.99-8.11 (m, 2H), 7.42-7.55 (m, 2H), 2.78 (d, 2H), 2.28 (s, 3H), 1.88-2.10 (m, 4H), 1.54-1.78 (m, 6H), 1.00-1.31 (m, 5H), 0.60-0.77 (m, 10H).

Synthesis Example 17

Synthesis of Compound 15

In the same manner as in Synthesis Example 8, except that 4.10 g (16.37 mmol) of 9,9-di-n-propylfluorene was changed to 4.84 g (16.37 mmol) of 2-nitro-9,9-di-n-propylfluoren, 5.33 g (10.70 mmol, yield: 77.6%) of a compound 15 was obtained.

2-Nitro-9,9-di-n-propylfluorene was obtained in the same manner as in Synthesis Example 2. The measurement results of $^1$H-NMR of the compound 14 are as follows.

$^1$H-NMR (600 MHz, CDCl$_3$, ppm): 8.41 (dd, 1H), 8.35 (d, 1H), 7.91-8.09 (m, 2H), 7.25-7.41 (m, 6H), 2.34 (s, 3H), 2.15 (s, 3H), 1.91-2.09 (m, 4H), 0.62-0.68 (m, 10H).

Synthesis Example 18

Synthesis of Compound 20

9,9-Di-n-propylfluorene 4.10 g, (16.37 mmol) was reacted with 2.78 g (18.00 mmol) of phenylacetic acid chloride in 50 ml of a dichloromethane solvent in the presence of 2.62 g of aluminum chloride under ice cooling for one hour. The organic layer was subjected to liquid separation by pouring the reaction mixture into ice water. The organic layer thus recovered was dried over anhydrous magnesium sulfate and then evaporated. The residue was purified by a silica gel column using an eluent of ethyl acetate/hexane=1/2 to obtain 2-phenylacetyl-9,9-di-n-propylfluorene. 2-Phenylacetyl-9,9-di-n-propylfluorene 5.73 g, (15.55 mmol) was reacted with 1.60 g (15.55 mmol) of concentrated hydrochloric acid in 25 ml of a dimethylformamide solvent in the presence of 2.42 g (23.33 mmol) of isobutyl nitrite under ice cooling for 3 hours. The reaction solution was evaporated and ethyl acetate was added to the residue, and the mixture was washed with a saturated saline solution, dried over anhydrous magnesium sulfate, and then evaporated to obtain 2-[phenyl(hydroxyimino)acetyl]-9,9-di-n-propylfluorene having the following structure.

[Chem. 27]

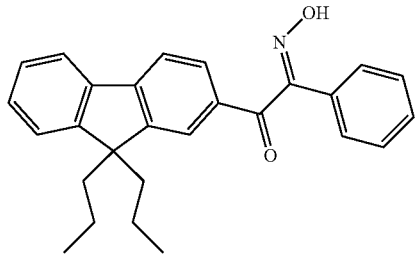

The measurement results of $^1$H-NMR of 2-[phenyl(hydroxyimino)acetyl]-9,9-di-n-propylfluorene are as follows.

$^1$H-NMR (600 MHz, CDCl$_3$, ppm): 8.05 (s, 1H), 7.76-7.92 (m, 2H), 7.75 (m, 2H), 7.61 (m, 2H), 7.30-7.41 (m, 5H), 1.92-2.05 (m, 4H), 0.58-0.70 (m, 10H).

2-[Phenyl(hydroxyimino)acetyl]-9,9-di-n-propylfluorene 4.64 g, (11.67 mmol), 1.43 g (13.42 mmol) of acetic anhydride, 1.36 g (13.42 mmol) of triethylamine, and 45.00 ml of a dimethylformamide solvent were mixed, followed by stirring at 35° C. for 3 hours. After cooling to room temperature, ethyl acetate was added to the reaction solution, and the mixture was washed with water, dried over anhydrous magnesium sulfate, and then evaporated. The residue was purified by a silica gel column using an eluent of ethyl acetate/hexane=2/1 to obtain 4.44 g (10.10 mmol, yield: 69%) of a compound 20. The measurement results of $^1$H-NMR of the compound 20 are as follows.

$^1$H-NMR (600 MHz, CDCl$_3$, ppm): 7.97 (s, 1H), 7.87 (dd, 1H), 7.74-7.79 (m, 4H), 7.72-7.80 (m, 1H), 7.35-7.52 (m, 5H), 1.95-2.03 (m, 4H), 1.94 (s, 3H), 0.58-0.65 (m, 10H).

Synthesis Example 19

Synthesis of Compound 26

9,9-Di-n-propylfluorene 4.10 g, (16.37 mmol) was reacted with 2.05 g (18.00 mmol) of glutaric anhydride in 50 ml of a dichloromethane solvent in the presence of 2.62 g of aluminum chloride under ice cooling for one hour. The organic layer was subjected to liquid separation by pouring the reaction mixture into ice water. The organic layer thus recovered was dried over anhydrous magnesium sulfate and then evaporated. The residue was purified by a silica gel column using an eluent of ethyl acetate/hexane=1/2 to obtain 5-oxo-5-(9,9-di-n-propylfluoren-2-yl)pentanoic acid.

5-Oxo-5-(9,9-di-n-propylfluoren-2-yl)pentanoic acid was esterified with a sulfuric acid catalyst in methanol to obtain methyl 5-oxo-5-(9,9-di-n-propylfluoren-2-yl)pentanoate. Methyl 5-oxo-5-(9,9-di-n-propylfluoren-2-yl)pentanoate 5.89 g, (15.55 mmol) was reacted with 1.60 g (15.55 mmol) of concentrated hydrochloric acid in 25 ml of a dimethylformamide solvent in the presence of 2.42 g (23.33 mmol) of isobutyl nitrite under ice cooling for 3 hours. The reaction solution was evaporated and ethyl acetate was added to the residue, and the mixture was washed with a saturated saline solution, dried over anhydrous magnesium sulfate, and then evaporated to obtain 2-[2-methoxycarbonylethyl(hydroxyimino)acetyl]-9,9-di-n-propylfluorene having the following structure.

[Chem. 28]

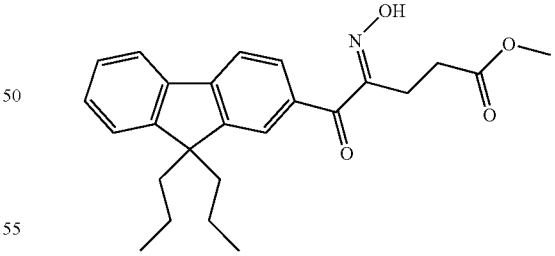

The measurement results of $^1$H-NMR of 2-[2-methoxycarbonylethyl(hydroxyimino)acetyl]-9,9-di-n-propylfluorene are as follows.

$^1$H-NMR (600 MHz, CDCl$_3$, ppm): 7.95-8.01 (m, 2H), 7.75-7.84 (m, 2H), 7.30-7.41 (m, 3H), 3.60 (s, 3H), 2.92 (t, 2H), 2.60 (t, 2H), 1.84-2.10 (m, 4H), 0.59-0.74 (m, 10H)

2-[2-Methoxycarbonylethyl(hydroxyimino)acetyl]-9,9-di-n-propylfluorene 4.76 g, (11.67 mmol), 1.43 g (13.42 mmol) of acetic anhydride, 1.36 g (13.42 mmol) of triethylamine, and 45.00 ml of a dimethylformamide solvent were mixed, followed by stirring at 35° C. for 3 hours. After cooling to room temperature, ethyl acetate was added to the reaction solution, and the mixture was washed with water, dried over anhydrous magnesium sulfate and then evaporated. The residue was purified by a silica gel column using an eluent of ethyl acetate/hexane=2/1 to obtain 4.73 g (10.30 mmol, yield: 70.6%) of a compound 26. The measurement results of $^1$H-NMR of the compound 26 are as follows.

$^1$H-NMR (600 MHz, CDCl$_3$, ppm): 7.91-8.01 (m, 2H), 7.76-7.83 (m, 2H), 7.32-7.40 (m, 3H), 3.61 (s, 3H), 2.93 (t, 2H), 2.63 (t, 2H), 2.19 (s, 3H), 1.85-2.10 (m, 4H), 0.59-0.73 (m, 10H)

Synthesis Example 20

Synthesis of 9,9-di-3,3,3-trifluoro-n-propylfluorene

Fluorene (6.64 g, 40 mmol) was dissolved in 27 mL of THF. After replacing the atmosphere in a reaction vessel with a nitrogen gas, the solution thus obtained was cooled to −20° C. After adding dropwise 15.8 g of n-butyllithium (1.6 M hexane solution) in a reaction vessel, the temperature of the reaction solution was returned to room temperature. Then, the reaction solution was stirred for one hour. The reaction solution was cooled to −78° C. and 8.96 g (80 mmol) of 1-iodo-3,3,3-trifluoropropane was gradually added. The mixture thus obtained was reacted by stirring for one hour after heating to room temperature. After the reaction, 90% acetic acid was added to the mixture, and then a saturated saline solution and hexane were added. The mixed solution thus obtained was separated into the organic layer and the aqueous layer. After the organic layer thus obtained was dehydrated over anhydrous sodium sulfate, the solvent was removed from the organic layer using a rotary evaporator to obtain 6.45 g (yield: 45%) of 9,9-di-3,3,3-trifluoro-n-propylfluorene.

Synthesis Example 21

Synthesis of Compound 27

9,9-Di-3,3,3-trifluoro-n-propylfluorene 5.87 g, (16.37 mmol) was reacted with 3.04 g (18.00 mmol) of (2-methylphenyl)acetic acid chloride in 50 ml of a dichloromethane solvent in the presence of 2.62 g of aluminum chloride under ice cooling for one hour. The organic layer was subjected to liquid separation by pouring the reaction mixture into ice water. The organic layer thus recovered was dried over anhydrous magnesium sulfate and then evaporated. The residue was purified by a silica gel column using an eluent of ethyl acetate/hexane=1/2 to obtain 2-(2-methylphenyl) acetyl-9,9-di-3,3,3-trifluoro-n-propylfluorene. 2-(2-Methylphenyl)acetyl-9,9-di-3,3,3-trifluoro-n-propylfluorene 7.63 g, (15.55 mmol) was reacted with 1.60 g (15.55 mmol) of concentrated hydrochloric acid in 25 ml of a dimethylformamide solvent in the presence of 2.42 g (23.33 mmol) of isobutyl nitrite under ice cooling for 3 hours. After the reaction solution was evaporated and ethyl acetate was added to the residue, the mixture was washed with a saturated saline solution, dried over anhydrous magnesium sulfate, and then evaporated to obtain 2-[2-methylphenyl (hydroxyimino)acetyl]-9,9-di-3,3,3-trifluoro-n-propylfluorene having the following structure.

[Chem. 29]

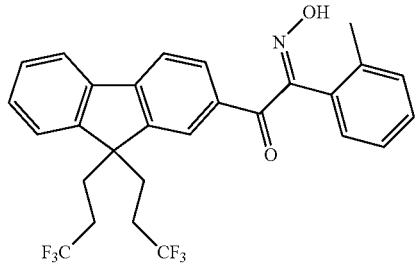

The measurement results of $^1$H-NMR of 2-[2-methylphenyl(hydroxyimino)acetyl]-9,9-di-3,3,3-trifluoro-n-propylfluorene are as follows.

$^1$H-NMR (600 MHz, CDCl$_3$, ppm): 8.65 (bs, 1H), 8.14 (d, 1H), 8.13 (s, 1H), 7.75-7.80 (m, 2H), 7.25-7.52 (m, 7H), 2.34 (s, 3H), 2.16-2.36 (m, 4H), 1.14-1.40 (m, 4H)

2-[2-Methylphenyl(hydroxyimino)acetyl]-9,9-di-3,3,3-trifluoro-n-propylfluorene 6.06 g, (11.67 mmol), 1.43 g (13.42 mmol) of acetic anhydride, 1.36 g (13.42 mmol) of triethylamine, and 45.00 ml of a dimethylformamide solvent were mixed, followed by stirring at 35° C. for 3 hours. After cooling to room temperature, ethyl acetate was added to the reaction solution, and the mixture was washed with water, dried over anhydrous magnesium sulfate, and then evaporated. The residue was purified by a silica gel column using an eluent of ethyl acetate/hexane=2/1 to obtain 5.78 g (10.30 mmol, yield: 70.6%) of a compound 27. The measurement results of $^1$H-NMR of the compound 27 are as follows.

$^1$H-NMR (600 MHz, CDCl$_3$, ppm): 7.97 (s, 1H), 7.87 (dd, 1H), 7.74-7.79 (m, 4H), 7.72-7.80 (m, 1H), 7.35-7.52 (m, 5H), 1.95-2.03 (m, 4H), 1.94 (s, 3H), 0.58-0.65 (m, 10H).

Synthesis Example 22

Synthesis of Compound 28

In the same manner as in Synthesis Example 21, except that 3.04 g (18.00 mmol) of (2-methylphenyl)acetic acid chloride was changed to 2.78 g (18.00 mmol) of phenylacetic acid chloride, 5.69 g (10.40 mmol, yield: 73%) of a compound 28 was obtained. The measurement results of $^1$H-NMR of the compound 28 are as follows.

$^1$H-NMR (600 MHz, CDCl$_3$, ppm): 7.95 (s, 1H), 7.85 (dd, 1H), 7.72-7.79 (m, 4H), 7.34-7.53 (m, 6H), 2.11-2.34 (m, 4H), 1.96 (s, 3H), 1.16-1.40 (m, 4H).

Synthesis Example 23

Synthesis of Compound 29

In the same manner as in Synthesis Example 21, except that 3.04 g (18.00 mmol) of (2-methylphenyl)acetic acid chloride was changed to 3.14 g (18.00 mmol) of 3-cyclohexylpropionic acid chloride, 5.90 g (10.40 mmol, yield: 73%) of a compound 29 was obtained. The measurement results of $^1$H-NMR of the compound 29 are as follows.

$^1$H-NMR (600 MHz, CDCl$_3$, ppm): 8.08-8.15 (m, 2H), 7.71-7.77 (m, 2H), 7.32-7.41 (m, 3H), 2.77 (d, 2H), 2.11-2.35 (m, 7H), 1.54-1.78 (m, 6H), 1.00-1.41 (m, 9H).

In Examples mentioned below, the above-mentioned compounds 1 to 15, compound 26, compound 27, and compound 29 were used as a photopolymerization initiator.

In Comparative Examples, comparative compounds 1 to 3 mentioned below were used as a photopolymerization initiator.

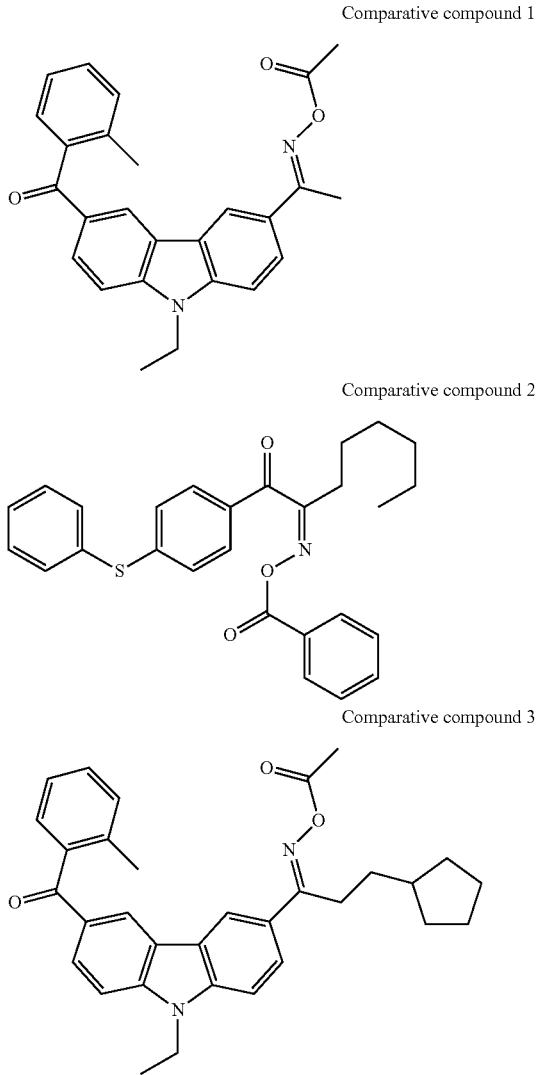

Comparative compound 1

Comparative compound 2

Comparative compound 3

Examples 1 to 26 and Comparative Examples 1 to 3

After diluting 40 parts by mass of dipentaerythritol hexaacrylate (manufactured by Nippon Kayaku Co., Ltd.), 58.5 parts by mass of a solution of an alkali-soluble resin, and 1.5 parts by mass of photopolymerization initiators mentioned in Table 1 and Table 2 with a mixed solvent of diethylene glycol methyl ethyl ether and propylene glycol monomethyl ether acetate to a solid component concentration of 15% by mass, these components were uniformly mixed to obtain photosensitive compositions of Examples 1 to 26 and Comparative Examples 1 to 3. A mass ratio of each solvent in the mixed solvent was 60/40 (diethylene glycol methyl ethyl ether/propylene glycol monomethyl ether acetate).

When the photopolymerization initiator is composed of two types of compounds, 0.45 part by mass of the compound mentioned in the upper column and 1.05 parts by mass of the compound mentioned in the lower column in Table 1 and Table 2 were used.

In Examples 1 to 26 and Comparative Examples 1 to 3, resins composed of the following units I to III were used as an alkali-soluble resin. In the following formulas, numeral placed at the lower right part of each unit means the content (% by mass) of each unit in the alkali-soluble resin. A mass average molecular weight of the alkali-soluble resin below was 7,000. The alkali-soluble resin was used as a diethylene glycol methyl ethyl ether solution having a solid component concentration of 30% by mass.

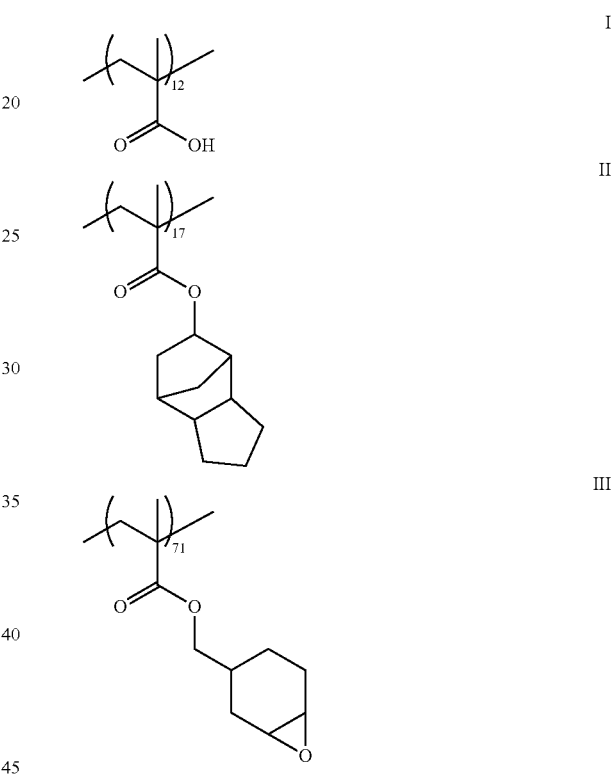

[Evaluation of Sensitivity]

Evaluation of sensitivity was carried out by the following procedure. First, each of photosensitive compositions of Examples 1 to 26 and Comparative Examples 1 to 3 was applied on a glass substrate (10 cm×10 cm) using a spin coater and then pre-baked at 90° C. for 120 seconds to form a coating film having a film thickness of 1.0 μm on a surface of the glass substrate. Then, the coating film was irradiated with ultraviolet rays via a negative mask with a pattern having a width of 10 μm formed thereon by using a mirror projection aligner (product name: TME-150RTO, manufactured by Topcon Corporation) with an exposure gap of 50 μm. The light exposure was set at three levels of 30, 60, and 1,200 mJ/cm$^2$. After the exposure, the coating film was developed with an aqueous 0.04% by mass KOH solution at 26° C. for 30 seconds and then post-baked at 230° C. for 30 minutes to form a line pattern at each light exposure. A line width of a pattern at each light exposure was measured by an optical microscope, and then a light exposure, at which a line width of 10 μm can be obtained, was calculated from line width at each light exposure and the light exposure, by approximation calculation using a least squares method. The thus calculated data of sensitivity (mJ/cm$^2$) at the developing time of 30 seconds are shown in Table 1 and Table 2. Data of sensitivity shown in Table 1 and Table 2 indicate the light exposure required to form a pattern (10 μm) having a predetermined line width. The smaller this numerical value, the more sensitivity of the photosensitive composition is higher.

[Evaluation of Line Pattern]

Each of the photosensitive compositions of Examples 1 to 26 and Comparative Examples 1 to 3 was applied on a glass substrate (100 mm×100 mm) using a spin coater and then pre-baked at 70° C. for 120 seconds to form a coating film. Then, the coating film was irradiated with ultraviolet rays via a negative mask with a line pattern having a width of 10 μm formed thereon by using a mirror projection aligner (product name: TME-150RTO, manufactured by Topcon Corporation) with an exposure gap of 50 μm. The light exposure was set at three levels of 50, 100, and 2,000 mJ/cm$^2$. After the exposure, the coating film was developed with an aqueous 0.04% by mass KOH solution at 26° C. for 50 seconds and then post-baked at 230° C. for 30 minutes to form a line pattern having a film thickness of 3.5 μm.

(Evaluation of Pattern Straightness)

Using an optical microscope, pattern straightness was evaluated by observing the line pattern thus formed. The pattern straightness was evaluated as "good" if there were no irregularities on the line edges, and as "poor" if there were irregularities.

(Evaluation of Pattern Detachment)

Using an optical microscope, the presence or absence of pattern detachment was recognized by observing the line pattern thus formed. The results of confirmation of the presence or absence of pattern detachment are shown in Table 1 and Table 2.

(Taper Angle)

With respect to a line pattern formed at a light exposure of 50 mJ/cm$^2$, a taper angle was evaluated. Regarding the taper angle, a joining angle between a pattern and a substrate was measured by a scanning electron microscope. This taper angle corresponds to an angle θ in FIGS. 1(*a*) and 1(*b*). The taper angle thus measured are shown in Table 1 and Table 2. The more the taper angle is closer to 90°, the more a shape of a pattern cross-section is closer to a desired rectangular shape. When the taper angle is an acute angle and is an angle which is considerably smaller than 90°, no undercut occurs in the pattern, but the shape of pattern cross-section is not a desired rectangular shape. When the taper angle is an obtuse angle, undercut occurs in the pattern.

(Film Thinning)

With respect to a line pattern at a light exposure of 50 mJ/cm$^2$, film thinning was evaluated. Specifically, the film thickness of a coating film before the development and the height of a cross-section of a line pattern after the development were measured by a scanning electron microscope, film thinning was determined by subtracting the height of a cross-section of a line pattern after the development from the film thickness of a coating film before the development.

(Transmittance)

In the same manner as in the method mentioned in the evaluation of a line pattern, except that the light exposure was set at 50 mJ/cm$^2$ and post-baking was performed at 230° C. for 60 minute, a line pattern was formed. With respect to the line pattern thus formed, a transmittance of light having a wavelength of 350 nm and 400 nm.

Evaluation criteria of the transmittance of light having a wavelength of 350 nm are as follows.

A: 95% or more
B: 90% or more and less than 94%
C: 80% or more and less than 90%
D: Less than 80%

[Foreign Materials]

Each of the photosensitive compositions of Examples 1 to 26 and Comparative Examples 1 to 3 was applied on a glass substrate (680 mm×880 mm) and then dried at 90° C. for 60 seconds to form a coating film having a film thickness of 1.5 μm. The coating film thus formed was exposed at a light exposure of 90 mJ/cm$^2$ by irradiation with ultraviolet rays via a mask, developed with an aqueous 0.04% by mass KOH solution at 26° C. for 30 seconds, and then post-baked at 230° C. for 30 minutes to obtain a black pattern having a predetermined shape. The shape of the pattern is a matrix shape in which 6 μm-width vertical and horizontal line, which intersect each other, are formed at intervals of 150 μm in a vertical direction and intervals of 50 μm in a horizontal direction.

The number of foreign materials having a size of 100 μm or more in the pattern thus formed was measured by Appearance Inspection System manufactured by TAKANO Co., Ltd. and then evaluation of foreign materials was performed by the following criteria. The evaluation results of foreign materials are shown in Table 1 and Table 2.

⊙: Number of foreign materials having a size of 100 μm or more in pattern is 0.
○: Number of foreign materials having a size of 100 μm or more in pattern is 1 or 2.
Δ: Number of foreign materials having a size of 100 μm or more in pattern is 3 to 5.
x: Number of foreign materials having a size of 100 μm or more in pattern is 6 or more.

TABLE 1

| | | | Evaluation of line pattern | | | | | Transmittance | | |
|---|---|---|---|---|---|---|---|---|---|---|
| | Type of photopolymerization initiator | Sensitivity (mJ/cm$^2$) | Upper column: Straightness Lower column: Pattern detachment Light exposure (mJ/cm$^2$) | | | Taper angle (°) | Film thinning (μm) | Upper column: (T %, 350 nm) Lower column: Evaluation | (T %) 400 nm | Foreign materials |
| | | | 50 | 100 | 200 | | | | | |
| Example 1 | Compound 1 | 20 | Good | Good | Good | 85 | 0.07 | 88 | 96 | ○ |
| | | | Not occurred | Not occurred | Not occurred | | | Δ | | |
| Example 2 | Compound 2 | 50 | Good | Good | Good | 82 | 0.11 | 88 | 98 | ○ |
| | | | Not occurred | Not occurred | Not occurred | | | Δ | | |
| Example 3 | Compound 3 | 25 | Good | Good | Good | 84 | 0.11 | 89 | 97 | ○ |
| | | | Not occurred | Not occurred | Not occurred | | | Δ | | |

TABLE 1-continued

| | | | Evaluation of line pattern | | | | | Transmittance | | |
|---|---|---|---|---|---|---|---|---|---|---|
| | Type of photopolymerization initiator | Sensitivity (mJ/cm²) | Upper column: Straightness Lower column: Pattern detachment Light exposure (mJ/cm²) | | | Taper angle (°) | Film thinning (μm) | Upper column: (T %, 350 nm) Lower column: Evaluation | (T %) 400 nm | Foreign materials |
| | | | 50 | 100 | 200 | | | | | |
| Example 4 | Compound 4 | 30 | Good Not occurred | Good Not occurred | Good Not occurred | 84 | 0.09 | 87 Δ | 96 | ○ |
| Example 5 | Compound 5 | 35 | Good Not occurred | Good Not occurred | Good Not occurred | 84 | 0.1 | 87 Δ | 96 | ○ |
| Example 6 | Compound 6 | 39 | Good Not occurred | Good Not occurred | Good Not occurred | 84 | 0.09 | 95 ◎ | 99 | ◎ |
| Example 7 | Compound 7 | 38 | Good Not occurred | Good Not occurred | Good Not occurred | 84 | 0.06 | 97 ◎ | 99 | ◎ |
| Example 8 | Compound 8 | 55 | Poor Not occurred | Good Not occurred | Good Not occurred | 78 | 0.08 | 95 ◎ | 99 | ◎ |
| Example 9 | Compound 9 | 45 | Good Not occurred | Good Not occurred | Good Not occurred | 83 | 0.07 | 97 ◎ | 99 | ◎ |
| Example 10 | Compound 10 | 41 | Good Not occurred | Good Not occurred | Good Not occurred | 83 | 0.08 | 95 ◎ | 99 | ◎ |
| Example 11 | Compound 11 | 42 | Good Not occurred | Good Not occurred | Good Not occurred | 83 | 0.09 | 95 ◎ | 99 | ◎ |
| Example 12 | Compound 12 | 20 | Good Not occurred | Good Not occurred | Good Not occurred | 87 | 0.05 | 90 ○ | 99 | ◎ |
| Example 13 | Compound 13 | 30 | Good Not occurred | Good Not occurred | Good Not occurred | 85 | 0.08 | 91 ○ | 99 | ◎ |
| Example 14 | Compound 14 | 12 | Good Not occurred | Good Not occurred | Good Not occurred | 88 | 0.05 | 90 ○ | 99 | ◎ |
| Example 15 | Compound 26 | 52 | Good Not occurred | Good Not occurred | Good Not occurred | 79 | 0.08 | 95 ◎ | 99 | ◎ |

TABLE 2

| | | | Evaluation of line pattern | | | | | Transmittance | | |
|---|---|---|---|---|---|---|---|---|---|---|
| | Type of photopolymerization initiator | Sensitivity (mJ/cm²) | Upper column: Straightness Lower column: Pattern detachment Light exposure (mJ/cm²) | | | Taper angle (°) | Film thinning (μm) | Upper column: (T %, 350 nm) Lower column: Evaluation | (T %) 400 nm | Foreign materials |
| | | | 50 | 100 | 200 | | | | | |
| Example 16 | Compound 27 | 38 | Good Not occurred | Good Not occurred | Good Not occurred | 84 | 0.09 | 95 ◎ | 99 | ◎ |
| Example 17 | Compound 29 | 36 | Good Not occurred | Good Not occurred | Good Not occurred | 85 | 0.09 | 97 ◎ | 99 | ◎ |
| Example 18 | Compound 15 | 12 | Good Not occurred | Good Not occurred | Good Not occurred | 87 | 0.06 | 90 ○ | 99 | ◎ |
| Example 19 | Compound 1/ Compound 6 | 32 | Good Not occurred | Good Not occurred | Good Not occurred | 85 | 0.08 | 93 ○ | 99 | ◎ |
| Example 20 | Compound 1/ Compound 7 | 31 | Good Not occurred | Good Not occurred | Good Not occurred | 84 | 0.08 | 94 ○ | 99 | ◎ |
| Example 21 | Compound 3/ Compound 6 | 34 | Good Not occurred | Good Not occurred | Good Not occurred | 85 | 0.07 | 92 ○ | 99 | ◎ |
| Example 22 | Compound 3/ Compound 7 | 35 | Good Not occurred | Good Not occurred | Good Not occurred | 85 | 0.06 | 94 ○ | 99 | ◎ |
| Example 23 | Compound 14/ Compound 6 | 30 | Good Not occurred | Good Not occurred | Good Not occurred | 87 | 0.06 | 94 ○ | 99 | ◎ |
| Example 24 | Compound 14/ Compound 7 | 30 | Good Not occurred | Good Not occurred | Good Not occurred | 86 | 0.06 | 94 ○ | 99 | ◎ |
| Example 25 | Compound 15/ Compound 6 | 31 | Good Not occurred | Good Not occurred | Good Not occurred | 86 | 0.07 | 94 ○ | 99 | ◎ |
| Example 26 | Compound 15/ Compound 7 | 30 | Good Not occurred | Good Not occurred | Good Not occurred | 86 | 0.06 | 94 ○ | 99 | ◎ |
| Comparative Example 1 | Comparative compound 1 | 75 | Good Not occurred | Good Not occurred | Good Not occurred | 73 | 0.57 | 78 X | 97 | Δ |
| Comparative Example 2 | Comparative compound 2 | 250 | Poor Occurred | Poor Not occurred | Good Not occurred | 61 | 0.91 | 98 ◎ | 99 | ○ |
| Comparative Example 3 | Comparative compound 3 | 60 | Good Not occurred | Good Not occurred | Good Not occurred | 77 | 0.31 | 79 X | 97 | X |

As is apparent from Table 1 and Table 2, the photosensitive compositions of Examples 1 to 26, each including a photopolymerizable compound, and a photopolymerization initiator containing a compound having a structure represented by the formula (1) as a photopolymerization initiator, are excellent in sensitivity. As is also apparent from Table 1 and Table 2, use of the photosensitive composition of Examples 1 to 26 enables formation of a line pattern, which is excellent in straightness and is free from detachment, and also has a cross-sectional shape of a desired rectangular shape without causing film thinning and deterioration in transparency due to heating.

Meanwhile, it is apparent that the photosensitive compositions of Comparative Examples 1 to 3, each containing a photopolymerization initiator having a structure not included the formula (1), are inferior in sensitivity. When a line pattern is formed using the photosensitive compositions of Comparative Examples 1 to 3, irregularities on edges of the line pattern and pattern detachment occur depending on light exposure, and also small taper angle and large film thinning occur, and thus it is not easy to form a line pattern with a cross-section having a desired rectangular shape.

Examples 27 to 52, and Comparative Examples 4 to 6

In Examples 27 to 52 and Comparative Examples 4 to 6, a resin A and dipentaerythritol hexaacrylate (manufactured by Nippon Kayaku Co., Ltd.) were used as a photopolymerizable compound. The resin A used was synthesized in accordance with the following formulation.

First, a 500 ml four-necked flask was charged with 235 g of a bisphenol fluorene type epoxy resin (epoxy equivalent: 235), 110 mg of tetramethylammonium chloride, 100 mg of 2,6-di-tert-butyl-4-methylphenol, and 72.0 g of acrylic acid, and then dissolved with heating at 90 to 100° C. while blowing air at a rate of 25 ml/min. Then, the temperature was gradually raised while the solution is in a cloudy state and heating to 120° C., leading to complete dissolution. In this case, the solution gradually became transparent and viscous, but stirring was continued. During stirring, an acid value was measured and stirring with heating was continued until the acid value reaches below 1.0 mgKOH/g. Twelve hours were required until the acid value reached a target value. The solution was cooled to room temperature to obtain a bisphenolfluorene type epoxy acrylate represented by the following structural formula (a4), which is colorless and transparent in a solid state.

Then, 307.0 g of the thus obtained bisphenolfluorene type epoxy acrylate was dissolved by adding 600 g of 3-methoxybutyl acetate, and mixed with 80.5 g of benzophenonetetracarboxlic anhydride and 1 g of tetramethylammonium bromide and the mixture was reacted by gradually raising the temperature at 110 to 115° C. for 4 hours. After confirming a disappearance of an anhydride group, the reaction mixture was mixed with 38.0 g of 1,2,3,6-tetrahydrophthalic anhydride, followed by a reaction at 90° C. for 6 hours to obtain a resin A. A disappearance of an anhydride group was confirmed by IR spectrum. This resin A corresponds to a compound represented by aforementioned formula (a1).

After diluting 30 parts by mass of a resin A, 15 parts by mass of types of dipentaerythritol hexaacrylate (manufactured by Nippon Kayaku Co., Ltd.), 5 parts by mass of photopolymerization initiators mentioned in Table 3 and Table 4, and 50 parts by mass of a carbon dispersion (CF Black, manufactured by Nanotech Mikuni Co., Ltd.) with a mixed solvent of 3-methoxybutyl acetate, cyclohexanone, and propylene glycol monomethyl ether acetate to a solid component concentration of 15% by mass, these components were uniformly mixed to obtain photosensitive compositions of Examples 27 to 52 and Comparative Examples 4 to 6. A mass ratio of each solvent in the mixed solvent was 60/20/20 (3-methoxybutyl acetate/cyclohexanone/propylene glycol monomethyl ether acetate).

When the photopolymerization initiator is composed of two types of compounds, two types of compounds were used in each amount of 2.5 parts by mass.

[Evaluation of Sensitivity]

valuation of sensitivity was carried out by the following procedure. First, each of photosensitive compositions of Examples 27 to 52 and Comparative Examples 4 to 6 was applied on a glass substrate (10 cm×10 cm) using a spin coater and then pre-baked at 90° C. for 120 seconds to form a coating film having a film thickness of 1.0 µm on a surface of the glass substrate. Then, the coating film was irradiated with ultraviolet rays via a negative mask with a pattern having a width of 10 µm formed thereon by using a mirror projection aligner (product name: TME-150RTO, manufactured by Topcon Corporation) with an exposure gap of 50 µm. The light exposure was set at three levels of 30, 60, and 1,200 mJ/cm$^2$. After the exposure, the coating film was developed with an aqueous 0.04% by mass KOH solution at 26° C. for 30 seconds and then post-baked at 230° C. for 30 minutes to form a pattern at each light exposure. A line width of a pattern at each light exposure was measured by an optical microscope, and then a light exposure, at which a line width of 10 µm can be obtained, was calculated from line width at each light exposure and the light exposure, by approximation calculation using a least squares method. The

[Chem. 32]

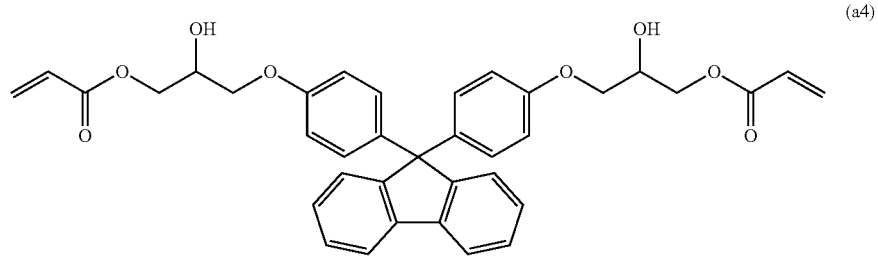

(a4)

thus calculated data of sensitivity (mJ/cm$^2$) at the developing time of 30 seconds are shown in Table 3 and Table 4. Data of sensitivity shown in Table 3 and Table 4 indicate the light exposure required to form a pattern (10 µm) having a predetermined line width. The smaller this numerical value, the more sensitivity of the photosensitive composition is higher.

[Evaluation of OD Value]

Each of the photosensitive compositions of Examples 27 to 52 and Comparative Examples 4 to 6 was applied on a 6-inch glass substrate (1737 glass, manufactured by Dow Corning Corp.) and then dried at 90° C. for 60 seconds to form a coating film. Then, this coating film was irradiated with ghi lines at a light exposure of 60 mJ/cm². Post-baking was performed on a hot plate at 230° C. for 20 minutes to form a light shielding film. The film thickness of the thus formed light shielding film was at three levels of 0.8 µm, 1.0 µm, and 1.2 µm. With respect to this light shielding film, an OD value in each film thickness was measured by using D200-II (manufactured by Macbeth) and then an OD value per 1 µm was calculated by an approximate curve. All of the calculated OD value of the light shielding film formed by using the photosensitive compositions of Examples 27 to 52 and Comparative Examples 4 to 6 was 4.5/µm.

[Pattern Straightness, and Pattern Detachment]

Pattern straightness and pattern detachment of a line pattern formed by using the photosensitive compositions of Examples 27 to 52 and Comparative Examples 4 to 6 were evaluated in the same manner as in Example 1, except that the light exposure was changed at four levels of 20, 40, 60, and 120 mJ/cm². The evaluation results of pattern straightness and pattern detachment are shown in Table 3 and Table 4.

[Taper Angle]

A taper angle of a cross-section of a line pattern formed at a light exposure of 40 mJ/cm² was measured in the same manner as in Example 1. Based on the thus measured taper angle, a cross-sectional shape of the line pattern was judged in accordance with the following criteria. The measurement results of the taper angle and judgment of the cross-sectional shape of the line pattern are shown in Table 3 and Table 4.

A: Taper angle is 70° or more and 85° or less.
B: Taper angle is more than 85° and 90° or less.
C: Taper angle is more than 90° and 100° or less.
D: Taper angle is more than 100°.

[Foreign Materials]

The content of foreign materials in a pattern formed by using the photosensitive compositions of Examples 27 to 52 and Comparative Examples 4 to 6 was evaluated in the same manner as in the photosensitive compositions of Examples 1 to 26 and Comparative Examples 1 to 3. The evaluation results of the foreign material are shown in Table 3 and Table 4.

[Water Resistance]

Each of the photosensitive compositions of Examples 27 to 52 and Comparative Examples 4 to 6 was applied on a glass substrate (100 mm×100 mm) in a film thickness of 1.2 µm. Then, the coating film thus formed was pre-baked at 90° C. for 60 seconds. After the entire surface of the coating film thus pre-baked was subjected to exposure at a light exposure of 100 mJ/cm², post-baking was performed at 230° C. for 210 minutes to obtain a black film. The black film was subjected to cross cutting to make cuts formed at intervals of 1 mm in vertical and horizontal directions, and then immersed in water under the conditions under 2 atoms at water temperature of 120° C. for 12 hours.

After immersion, the glass substrate including the black film was dried and subjected to a tape test in accordance with ASTM D3359-09e2, and then water resistance of the black film was evaluated from a detached state of squares of the black film formed by cross cutting after the tape test. Evaluation criteria of water resistance are as follows. The evaluation results of water resistance are shown in Table 3 and Table 4.

5B: None of squares have detached.
4B: Number of detached squares accounts for less than 5% of total number of squares.
3B: Number of detached squares accounts for 5% or more and less than 15% of the total number of squares.
2B: Number of detached squares accounts for 15% or more and less than 35% of the total number of squares.
1B: Number of detached squares accounts for 35% or more and less than 65% of the total number of squares.
0B: Number of detached squares accounts for 65% or more of the total number of squares.

TABLE 3

| | Type of photopolymerization initiator | Sensitivity (mJ/cm²) | Evaluation of line pattern Upper Lower column: Pattern detachment Light exposure (mJ/cm²) | | | Taper angle (°) | Judgment of cross-sectional shape | Foreign materials | Evaluation of water resistance |
|---|---|---|---|---|---|---|---|---|---|
| | | | 40 | 60 | 120 | | | | |
| Example 27 | Compound 1 | 20 | Good<br>Not occurred | Good<br>Not occurred | Good<br>Not occurred | 83 | ◎ | ○ | 3B |
| Example 28 | Compound 2 | 65 | Good<br>Not occurred | Good<br>Not occurred | Good<br>Not occurred | 90 | ○ | ○ | 3B |
| Example 29 | Compound 3 | 50 | Good<br>Not occurred | Good<br>Not occurred | Good<br>Not occurred | 84 | ◎ | ○ | 3B |
| Example 30 | Compound 4 | 35 | Good<br>Not occurred | Good<br>Not occurred | Good<br>Not occurred | 86 | ○ | ○ | 3B |
| Example 31 | Compound 5 | 40 | Good<br>Not occurred | Good<br>Not occurred | Good<br>Not occurred | 87 | ○ | ○ | 3B |
| Example 32 | Compound 6 | 41 | Good<br>Not occurred | Good<br>Not occurred | Good<br>Not occurred | 86 | ○ | ◎ | 5B |
| Example 33 | Compound 7 | 43 | Good<br>Not occurred | Good<br>Not occurred | Good<br>Not occurred | 85 | ○ | ◎ | 5B |
| Example 34 | Compound 8 | 60 | Good<br>Not occurred | Good<br>Not occurred | Good<br>Not occurred | 89 | ○ | ◎ | 4B |
| Example 35 | Compound 9 | 50 | Good<br>Not occurred | Good<br>Not occurred | Good<br>Not occurred | 88 | ○ | ◎ | 5B |
| Example 36 | Compound 10 | 42 | Good<br>Not occurred | Good<br>Not occurred | Good<br>Not occurred | 84 | ◎ | ◎ | 5B |
| Example 37 | Compound 11 | 43 | Good<br>Not occurred | Good<br>Not occurred | Good<br>Not occurred | 85 | ○ | ◎ | 5B |

TABLE 3-continued

| | Type of photopolymerization initiator | Sensitivity (mJ/cm²) | Evaluation of line pattern Upper Lower column: Pattern detachment Light exposure (mJ/cm²) | | | Taper angle (°) | Judgment of cross-sectional shape | Foreign materials | Evaluation of water resistance |
|---|---|---|---|---|---|---|---|---|---|
| | | | 40 | 60 | 120 | | | | |
| Example 38 | Compound 12 | 20 | Good Not occurred | Good Not occurred | Good Not occurred | 82 | ◎ | ◎ | 4B |
| Example 39 | Compound 13 | 30 | Good Not occurred | Good Not occurred | Good Not occurred | 84 | ◎ | ◎ | 4B |
| Example 40 | Compound 14 | 15 | Good Not occurred | Good Not occurred | Good Not occurred | 80 | ◎ | ◎ | 4B |
| Example 41 | Compound 26 | 57 | Good Not occurred | Good Not occurred | Good Not occurred | 89 | ○ | ◎ | 4B |
| Comparative Example 4 | Comparative compound 1 | 75 | Poor Not occurred | Good Not occurred | Good Not occurred | 103 | X | X | 2B |
| Comparative Example 5 | Comparative compound 2 | 400 | Poor Occurred | Poor Occurred | Good Not occurred | Pattern detachment | X | X | 5B |
| Comparative Example 6 | Comparative compound 3 | 70 | Good Not occurred | Good Not occurred | Good Not occurred | 95 | Δ | X | 2B |

TABLE 4

| | Type of photopolymerization initiator | Sensitivity (mJ/cm²) | Evaluation of line pattern Upper Lower column: Pattern detachment Light exposure (mJ/cm²) | | | Taper angle (°) | Judgment of cross-sectional shape | Foreign materials | Evaluation of water resistance |
|---|---|---|---|---|---|---|---|---|---|
| | | | 40 | 60 | 120 | | | | |
| Example 42 | Compound 27 | 38 | Good Not occurred | Good Not occurred | Good Not occurred | 87 | ○ | ◎ | 5B |
| Example 43 | Compound 29 | 39 | Good Not occurred | Good Not occurred | Good Not occurred | 86 | ○ | ◎ | 5B |
| Example 44 | Compound 15 | 14 | Good Not occurred | Good Not occurred | Good Not occurred | 81 | ◎ | ◎ | 5B |
| Example 45 | Compound 1/ Compound 6 | 30 | Good Not occurred | Good Not occurred | Good Not occurred | 83 | ◎ | ◎ | 5B |
| Example 46 | Compound 1/ Compound 7 | 31 | Good Not occurred | Good Not occurred | Good Not occurred | 82 | ◎ | ◎ | 5B |
| Example 47 | Compound 3/ Compound 6 | 35 | Good Not occurred | Good Not occurred | Good Not occurred | 84 | ◎ | ◎ | 5B |
| Example 48 | Compound 3/ Compound 7 | 36 | Good Not occurred | Good Not occurred | Good Not occurred | 84 | ◎ | ◎ | 5B |
| Example 49 | Compound 14/ Compound 6 | 27 | Good Not occurred | Good Not occurred | Good Not occurred | 82 | ◎ | ◎ | 5B |
| Example 50 | Compound 14/ Compound 7 | 28 | Good Not occurred | Good Not occurred | Good Not occurred | 84 | ◎ | ◎ | 5B |
| Example 51 | Compound 15/ Compound 6 | 27 | Good Not occurred | Good Not occurred | Good Not occurred | 83 | ◎ | ◎ | 5B |
| Example 52 | Compound 15/ Compound 7 | 28 | Good Not occurred | Good Not occurred | Good Not occurred | 82 | ◎ | ◎ | 5B |
| Comparative Example 4 | Comparative compound 1 | 75 | Poor Not occurred | Good Not occurred | Good Not occurred | 103 | X | X | 2B |
| Comparative Example 5 | Comparative compound 2 | 400 | Poor Occurred | Poor Occurred | Good Not occurred | Pattern detachment | X | X | 5B |
| Comparative Example 6 | Comparative compound 3 | 70 | Good Not occurred | Good Not occurred | Good Not occurred | 95 | Δ | X | 2B |

As is apparent from Table 3 and Table 4, the photosensitive compositions of Examples 27 to 52, each including a photopolymerizable compound, and a photopolymerization initiator containing a compound having a structure represented by the formula (1) as a photopolymerization initiator, are excellent in sensitivity even if a light shielding agent is contained as a coloring agent. As is also apparent from Table 3 and Table 4, use of the photosensitive composition of Examples 27 to 52 enables formation of a line pattern, which is excellent in straightness and is free from detachment, and has a cross-sectional shape of a desired rectangular shape, and also has less content of foreign materials and excellent water resistance.

Meanwhile, it is apparent that the photosensitive compositions of Comparative Examples 4 to 6, each containing a photopolymerization initiator having a structure not included the formula (1), are inferior in sensitivity. When a line pattern is formed using the photosensitive compositions of Comparative Examples 4 to 6, irregularities on edges of the line pattern and pattern detachment occur depending on light exposure, and also a taper angle is an obtuse angle and undercut occurs in the line pattern. When a pattern is formed using the photosensitive compositions of Comparative Examples 4 to 6, a pattern having large content of foreign materials and poor water resistance is likely to be formed.

EXPLANATION OF REFERENCE NUMERALS

1: Cross-section in width direction in pattern having no undercut existing therein
2: Cross-section in width direction in pattern having an undercut existing therein

The invention claimed is:

1. A photosensitive composition comprising (A) a photopolymerizable compound and (B) a photopolymerization initiator, wherein the photopolymerization initiator (B) comprises a compound represented by the following formula (1):

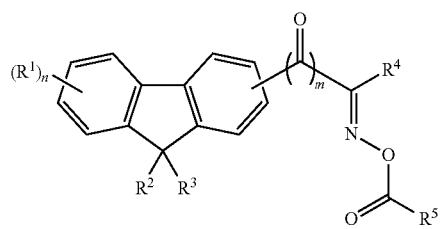

(1)

wherein $R^1$ is a hydrogen atom; $R^2$ and $R^3$ each are a chain alkyl group which may have a substituent, a cyclic organic group which may have a substituent, or a hydrogen atom; $R^2$ and $R^3$ may be bonded to one another to form a ring; $R^4$ is a group represented by the following formula (R4-2); $R^5$ is a hydrogen atom, an alkyl group having 1 to 11 carbon atoms which may have a substituent, or an aryl group which may have a substituent; n is 4; and m is 1

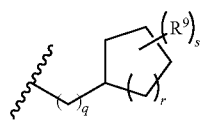

(R4-2)

wherein q is an integer of 1 to 8; r is an integer of 1 to 5; s is an integer of 0 to (r+3); and $R^9$ is an organic group.

2. The photosensitive composition according to claim 1, further comprising (C) a coloring agent.

3. The photosensitive composition according to claim 2, wherein the coloring agent (C) is a light shielding agent.

4. The photosensitive composition according to claim 1, wherein the photopolymerizable compound (A) comprises a compound represented by the following formula (a1):

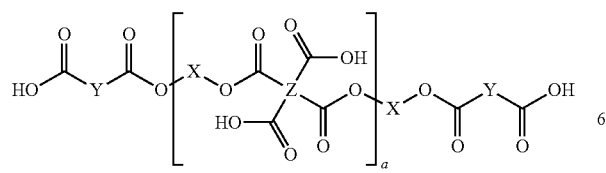

(a1)

wherein Y represents a residue in which an anhydride group (—CO—O—CO—) is removed from dicarboxylic anhydride, Z represents a residue in which two anhydride groups are removed from tetracarboxylic dianhydride, a represents an integer of 0 to 20, X represents a group represented by the following formula (a2):

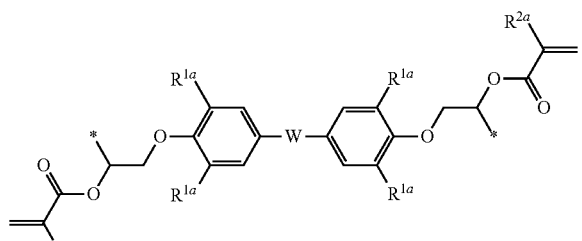

(a2)

wherein $R^{1a}$ each independently represents a hydrogen atom, a hydrocarbon group having 1 to 6 carbon atoms, or a halogen atom, $R^{2a}$ each independently represents a hydrogen atom or methyl group, and W represents a single bond or a group represented by a structural formula (a3) below, and wherein in the formula (a2) and the structural formula (a3), "*" means the end of a bond of a divalent group.

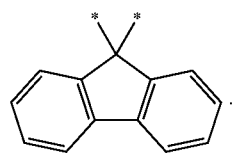

(a3)

5. The photosensitive composition according to claim 1, wherein in the formula (R4-2), q is an integer of 1 to 3; r is 1 or 2; and s is 0.

6. The photosensitive composition according to claim 1, wherein the compound represented by the formula (1) is the compound 7, 9 or 29

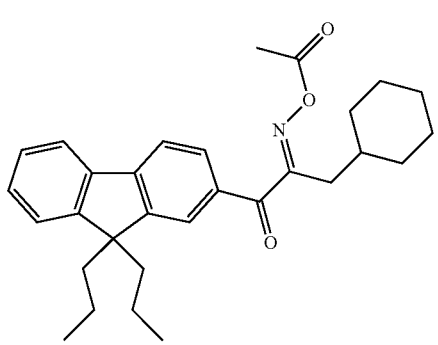

Compound 7

-continued
Compound 9
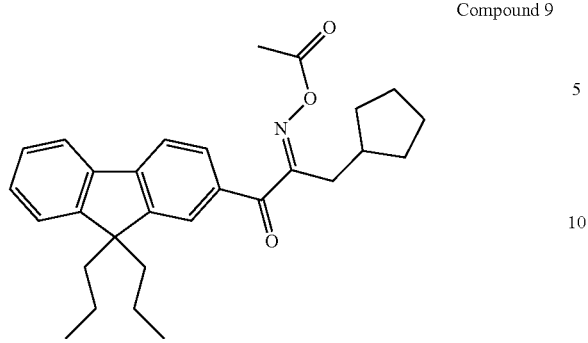
Compound 29
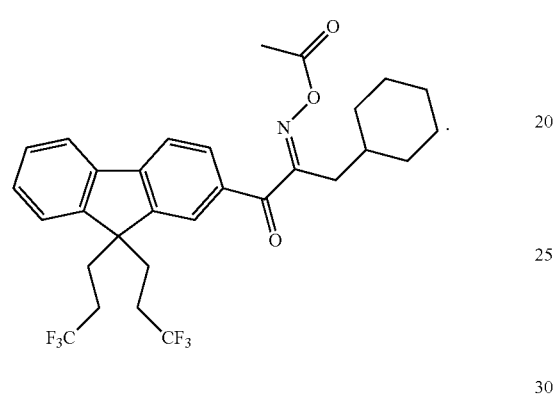
* * * * *